United States Patent
Suzuki et al.

(10) Patent No.: US 11,109,593 B2
(45) Date of Patent: Sep. 7, 2021

(54) ISOXAZOLIN-5-ONE DERIVATIVE AND HERBICIDE CONTAINING SAME AS ACTIVE INGREDIENT

(71) Applicant: HOKKO CHEMICAL INDUSTRY CO., LTD., Tokyo (JP)

(72) Inventors: Jun Suzuki, Kanagawa (JP); Keiyo Nakai, Kanagawa (JP); Kohei Koyama, Kanagawa (JP); Yutaro Tanaka, Kanagawa (JP); Tsunehiro Kido, Kanagawa (JP)

(73) Assignee: HOKKO CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/479,099

(22) PCT Filed: Jan. 19, 2018

(86) PCT No.: PCT/JP2018/001687
§ 371 (c)(1),
(2) Date: Jul. 18, 2019

(87) PCT Pub. No.: WO2018/135649
PCT Pub. Date: Jul. 26, 2018

(65) Prior Publication Data
US 2020/0267985 A1 Aug. 27, 2020

(30) Foreign Application Priority Data
Jan. 20, 2017 (JP) .............................. JP2017-008553

(51) Int. Cl.
*A01N 43/80* (2006.01)
*C07D 261/12* (2006.01)
*C07D 413/12* (2006.01)

(52) U.S. Cl.
CPC ........... *A01N 43/80* (2013.01); *C07D 261/12* (2013.01); *C07D 413/12* (2013.01)

(58) Field of Classification Search
None
See application file for complete search history.

(56) References Cited

U.S. PATENT DOCUMENTS

| | | |
|---|---|---|
| 4,000,155 A | 12/1976 | Beck et al. |
| 4,797,148 A | 1/1989 | Hagen et al. |
| 5,489,570 A | 2/1996 | Geach et al. |
| 6,323,155 B1 | 11/2001 | Musil et al. |
| 2002/0045551 A1 | 4/2002 | Musil et al. |
| 2004/0204320 A1 | 10/2004 | Seitz et al. |
| 2008/0274892 A1 | 11/2008 | Hino et al. |
| 2010/0016164 A1 | 1/2010 | Hino et al. |
| 2012/0029187 A1 | 2/2012 | Kai et al. |
| 2014/0329679 A1 | 11/2014 | De Fraine et al. |

FOREIGN PATENT DOCUMENTS

| | | |
|---|---|---|
| DE | 3541722 | 5/1987 |
| EP | 1 852 425 | 11/2007 |
| EP | 2 336 104 | 6/2011 |
| JP | 7-149742 | 6/1995 |
| JP | 8-504781 | 5/1996 |
| JP | 2005-526824 | 9/2005 |
| JP | 2010-209061 | 9/2010 |
| JP | 2015-500261 | 1/2015 |
| WO | 2004/011429 | 2/2004 |
| WO | 2006/090792 | 8/2006 |
| WO | 2008/059948 | 5/2008 |
| WO | 2008/102908 | 8/2008 |
| WO | 2010/026989 | 3/2010 |
| WO | 2010/119906 | 10/2010 |
| WO | 2014/175206 | 10/2014 |
| WO | 2015/004282 | 1/2015 |

(Continued)

OTHER PUBLICATIONS

Snyder, L. B.; et al. "Discovery of isoxazolinone antibacterial agents. Nitrogen as a replacement for the stereogenic center found in oxazolidinone antibacterials" Bioorganic & Medicinal Chemistry Letters, 2004, 14, 4735-4739. (Year: 2004).*

International Search Report, dated Apr. 10, 2018 in corresponding International Patent Application No. PCT/JP2018/001687, with English language translation.

Song et al., "Synthesis and Herbicidal Activity of Novel 4-Acyl-2,5-disubstituted-3-hydroxypryrazoles and 4-Arylcarbonyl-3-substituteddisoxazol-5-ones", Journal of Heterocyclic Chemistry, 50: 1381-1385 (2013).

(Continued)

*Primary Examiner* — Erin E Hirt
(74) *Attorney, Agent, or Firm* — Wenderoth, Lind & Ponack, L.L.P.

(57) ABSTRACT

An isoxazolin-5-one derivative represented by the following (1):

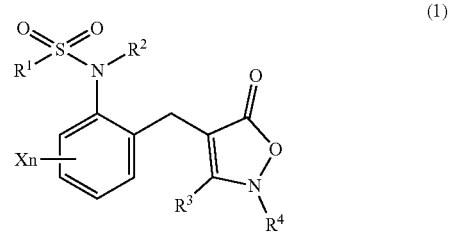

wherein $R^1$ represents a C1-C6 haloalkyl group, and $R^2$ to $R^4$ and X each represents a certain substituent or the like; and n represents an integer of 1 to 4, wherein X's may be different from each other when n represents an integer of 2 to 4, and an herbicide containing the isoxazolin-5-one derivative as an active ingredient are provided.

11 Claims, No Drawings

(56) References Cited

FOREIGN PATENT DOCUMENTS

| WO | 2015/097071 | 7/2015 |
| WO | 2016/056565 | 4/2016 |

OTHER PUBLICATIONS

Sato et al., Synthesis of 3-Hydroxyisoxazoles from β-Ketoesters, Agric. Biol. Chem., 50(7): 1831-1837 (1986).

Extended European Search Report dated May 26, 2020 in European Patent Application No. 18741643.3.

Office Action dated Jan. 12, 2021 in corresponding Indian Patent Application No. 201917029244.

Office Action dated Mar. 18, 2021 in corresponding Australian Patent Application No. 2018210807, 3 pages.

\* cited by examiner

ISOXAZOLIN-5-ONE DERIVATIVE AND HERBICIDE CONTAINING SAME AS ACTIVE INGREDIENT

TECHNICAL FIELD

The present invention provides isoxazolin-5-one derivatives and herbicides which contain the isoxazolin-5-one derivatives as active ingredients and which have a particularly excellent control effect on a harmful weed in an agricultural or horticultural field or in a non-crop land.

BACKGROUND ART

Use of herbicides is indispensable for protecting useful crops such as rice, wheat, corn, soybeans, cotton plant and beets from weeds and for increasing the yield. Recently, a selective herbicide which does not damage crops but which can selectively kill weeds only is desired in cultivated land where both such a useful crop and weeds grow. Moreover, an agent which exhibits a high herbicidal effect with a possible low agent amount is required in view of the prevention of environmental pollution, a decrease in the economic costs in transport and spraying and the like.

Here, although isoxazolin-5-one derivatives exhibiting a similar herbicidal activity to that of the invention are reported in Patent Literatures 1 and 2 and Non Patent Literature 1, the compounds of the invention in which the 4-position of the isoxazolin-5-one ring is substituted with a 2-(haloalkylsulfonylamino)benzyl group are not reported at all. It is known that heterocyclic compounds having a haloalkylsulfonylamino group at the 2-position of a benzyl group have a herbicidal activity (Patent Literatures 3 to 12). However, there is no report showing that compounds in which the heterocyclic moiety is isoxazolin-5-one, as in the invention, exhibit a herbicidal activity.

BACKGROUND ART LITERATURE

Patent Literature

Patent Literature 1: U.S. Pat. No. 4,000,155
Patent Literature 2: German Published Patent No. 3541722
Patent Literature 3: WO2004/011429
Patent Literature 4: WO2006/090792
Patent Literature 5: WO2008/059948
Patent Literature 6: WO2008/102908
Patent Literature 7: WO2010/026989
Patent Literature 8: WO2010/119906
Patent Literature 9: WO2014/175206
Patent Literature 10: WO2016/056565
Patent Literature 11: WO2015/004282
Patent Literature 12: WO2015/097071

Non Patent Literature

Non Patent Literature 1: Journal of Heterocyclic Chemistry, Vol. 50, 2013, P. 1381-1385

SUMMARY OF INVENTION

Technical Problem

A problem to be solved by the invention is to provide an herbicide having an excellent herbicidal activity and crop selectivity.

Solution to Problem

As a result of intensive studies to solve the problem, the present inventors have found that isoxazolin-5-one derivatives represented by the following formula (1) below exhibit an excellent herbicidal activity and thus have completed the invention.

Accordingly, the first invention of the present application relates to isoxazolin-5-one derivatives represented by the following formula (1) (sometimes referred to as "the compounds of the invention" in this description).

The second invention of the application relates to herbicides characterized by containing an isoxazolin-5-one derivative represented by the following formula (1) as an active ingredient.

That is, the inventors have found that the following aspects can solve the problem.

[1]

An isoxazolin-5-one derivative represented by the following formula (1) below:

wherein in the formula (1), $R^1$ represents a C1-C6 haloalkyl group;
$R^2$ represents a hydrogen atom, a C1-C6 alkyl group, a C1-C6 haloalkyl group, a C2-C6 alkenyl group, a C2-C6 alkynyl group, a C1-C6 alkoxy C1-C6 alkyl group, a C1-C6 haloalkoxy C1-C6 alkyl group, a C1-C6 alkoxy C1-C6 alkoxy C1-C6 alkyl group, a C1-C6 alkylthio C1-C6 alkyl group, a C1-C6 alkylcarbonyl C1-C6 alkyl group, a C7-C11 aralkyl group which may be substituted (the group may be monosubstituted or polysubstituted with a halogen atom, a C1-C6 alkyl group or a C1-C6 alkoxy group), a phenoxy C1-C6 alkyl group, a C7-C11 aralkyloxy C1-C6 alkyl group, a phenylcarbonyl C1-C6 alkyl group, a C1-C6 alkylcarbonyl group, a C1-C6 haloalkylcarbonyl group, a C2-C6 alkenylcarbonyl group, a C2-C6 alkynylcarbonyl group, a C3-C6 cycloalkylcarbonyl group, a C3-C6 cycloalkyl C1-C6 alkylcarbonyl group, a C1-C6 alkoxy C1-C6 alkylcarbonyl group, a C1-C6 haloalkoxy C1-C6 alkylcarbonyl group, a C1-C6 alkoxy C1-C6 alkoxy C1-C6 alkylcarbonyl group, a C1-C6 alkylthio C1-C6 alkylcarbonyl group, a C1-C6 haloalkylthio C1-C6 alkylcarbonyl group, a benzoyl group which may be substituted (the group may be monosubstituted or polysubstituted with a halogen atom or a C1-C6 alkyl group), a C7-C11 aralkylcarbonyl group which may be substituted (the group may be monosubstituted or polysubstituted with a halogen atom or a C1-C6 alkyl group), a heterocyclic carbonyl group which may be substituted (the group may be monosubstituted or polysubstituted with a halogen atom or a C1-C6 alkyl group), a heterocyclic C1-C6 alkylcarbonyl group which may be substituted (the group may be monosubstituted or polysubstituted with a halogen atom or a C1-C6 alkyl group), a C1-C6 alkoxycarbonyl group, a C1-C6 haloalkoxycarbonyl group, a C2-C6 alkenyloxycarbonyl group, a C2-C6 alkynyloxycarbonyl group, a C3-C6 cycloalkyloxycarbonyl group, a C3-C6 cycloalkyl C1-C6 alkoxycarbonyl group, a C1-C6 alkoxy C1-C6 alkoxycarbonyl group, a C1-C6 haloalkoxy C1-C6 alkoxycarbonyl group, a C1-C6 alkoxy C1-C6 alkoxy C1-C6 alkoxycarbonyl group, a C1-C6 alkylthio C1-C6 alkoxycarbonyl group, a C1-C6 haloalkylthio C1-C6 alkoxycarbonyl group, a phenoxycarbonyl group which may be substituted (the group may be monosubstituted or polysubstituted with a halogen atom or a C1-C6 alkyl group), a C7-C11 aralkyloxycarbonyl group which may be substituted (the group may be monosubstituted or polysubstituted with a halogen atom or a C1-C6 alkyl group), a phenoxy C1-C6 alkoxycarbonyl group which may be substituted (the group may be monosubstituted or polysubstituted with a halogen atom or a C1-C6 alkyl group), a heterocyclic oxycarbonyl group which may be substituted (the group may be monosubstituted or polysubstituted with a halogen atom or a C1-C6 alkyl group), a heterocyclic C1-C6 alkoxycarbonyl group which may be substituted (the group may be monosubstituted or polysubstituted with a halogen atom or a C1-C6 alkyl group), a C1-C6 alkylthiocarbonyl group, a C1-C6 haloalkylthiocarbonyl group, a C1-C6 alkylaminocarbonyl group, a C1-C6 haloalkylaminocarbonyl group, a di-C1-C6 alkylaminocarbonyl group wherein the di-C1-C6 alkyl groups may be same or different, a C1-C6 alkylsulfonyl group, a C1-C6 haloalkylsulfonyl group, a C2-C6 alkenylsulfonyl group, a C2-C6 alkynylsulfonyl group, a C3-C6 cycloalkylsulfonyl group, a C3-C6 cycloalkyl C1-C6 alkylsulfonyl group, a C1-C6 alkoxy C1-C6 alkylsulfonyl group, a phenylsulfonyl group which may be substituted (the group may be monosubstituted or polysubstituted with a halogen atom or a C1-C6 alkyl group), a C7-C11 aralkylsulfonyl group which may be substituted (the group may be monosubstituted or polysubstituted with a halogen atom or a C1-C6 alkyl group), a C1-C6 alkylaminosulfonyl group or a di-C1-C6 alkylaminosulfonyl group wherein the di-C1-C6 alkyl groups may be same or different;

$R^3$ represents a hydrogen atom, a halogen atom, a C1-C6 alkyl group, a C1-C6 haloalkyl group, a C3-C6 cycloalkyl group, a phenyl group which may be substituted (the group may be monosubstituted or polysubstituted with a halogen atom or a C1-C6 alkyl group), an amino group, a C1-C6 alkylamino group or a di-C1-C6 alkylamino group wherein the di-C1-C6 alkyl groups may be same or different;

$R^4$ represents a hydrogen atom, a C1-C15 alkyl group, a C1-C15 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 cycloalkyl C1-C6 alkyl group, a C1-C6 alkoxy C1-C6 alkyl group, a C1-C6 haloalkoxy C1-C6 alkyl group, a C1-C6 alkoxy C1-C6 alkoxy C1-C6 alkyl group, a C1-C6 alkylthio C1-C6 alkyl group, a C1-C6 haloalkylthio C1-C6 alkyl group, a C1-C6 alkylsulfinyl C1-C6 alkyl group, a C1-C6 alkylsulfonyl C1-C6 alkyl group, a C1-C6 alkylamino C1-C6 alkyl group, a di-C1-C6 alkylamino C1-C6 alkyl group wherein the di-C1-C6 alkyl groups may be same or different, a C1-C6 alkylcarbonyl C1-C6 alkyl group, a phenyl group which may be substituted (the group may be monosubstituted or polysubstituted with a halogen atom, a C1-C6 alkyl group or a C1-C6 alkoxy group), a C7-C11 aralkyl group which may be substituted (the group may be monosubstituted or polysubstituted with a halogen atom, cyano, nitro, a C1-C6 alkyl group, a C1-C6 haloalkyl group, a C1-C6 alkoxy group, a C1-C6 haloalkoxy group, a C1-C6 alkylthio group or a C1-C6 haloalkylthio group), an indanyl group which may be substituted (the group may be monosubstituted or polysubstituted with a halogen atom, a C1-C6 alkyl group or a C1-C6 alkoxy group), a tetrahydronaphthyl group which may be substituted (the group may be monosubstituted or polysubstituted with a halogen atom, a C1-C6 alkyl group or a C1-C6 alkoxy group), a heterocyclic C1-C6 alkyl group which may be substituted (the group may be monosubstituted or polysubstituted with a halogen atom, a C1-C6 alkyl group or a C1-C6 alkoxy group), a phenoxy C1-C6 alkyl group which may be substituted (the group may be monosubstituted or polysubstituted with a halogen atom, a C1-C6 alkyl group or a C1-C6 alkoxy group), a C7-C11 aralkyloxy C1-C6 alkyl group which may be substituted (the group may be monosubstituted or polysubstituted with a halogen atom, a C1-C6 alkyl group or a C1-C6 alkoxy group), a phenylcarbonyl C1-C6 alkyl group which may be substituted (the group may be monosubstituted or polysubstituted with a halogen atom, a C1-C6 alkyl group or a C1-C6 alkoxy group), a C1-C6 alkylcarbonyl group, a benzoyl group which may be substituted (the group may be monosubstituted or polysubstituted with a halogen atom, a C1-C6 alkyl group or a C1-C6 alkoxy group), a C7-C11 aralkylcarbonyl group which may be substituted (the group may be monosubstituted or polysubstituted with a halogen atom, a C1-C6 alkyl group or a C1-C6 alkoxy group), a C1-C6 alkoxycarbonyl group, a C1-C6 alkylaminocarbonyl group, a di-C1-C6 alkylaminocarbonyl group wherein the di-C1-C6 alkyl groups may be same or different, a C1-C6 alkylsulfonyl group, a C1-C6 haloalkylsulfonyl group, a phenylsulfonyl group which may be substituted (the group may be monosubstituted or polysubstituted with a halogen atom, a C1-C6 alkyl group or a C1-C6 alkoxy group) or a C7-C11 aralkylsulfonyl group which may be substituted (the group may be monosubstituted or polysubstituted with a halogen atom, a C1-C6 alkyl group or a C1-C6 alkoxy group);

X represents a hydrogen atom, a halogen atom, a C1-C6 alkyl group or a C1-C6 alkoxy group; and n represents an integer of 1 to 4, wherein X's may be different from each other when n represents an integer of 2 to 4.

[2] The isoxazolin-5-one derivative according to [1], wherein $R^1$ in the formula (1) is a C1-C6 fluoroalkyl group.

[3] The isoxazolin-5-one derivative according to [1] or [2], wherein $R^1$ in the formula (1) is a trifluoromethyl group.

[4] The isoxazolin-5-one derivative according to any one of [1] to [3],
wherein in the formula (1),
$R^1$ is a trifluoromethyl group;
$R^2$ is a hydrogen atom, a C1-C6 alkyl group, a C1-C6 alkoxy C1-C6 alkyl group, a C7-C11 aralkyl group which may be substituted (the group may be monosubstituted or polysubstituted with a halogen atom, a C1-C6 alkyl group or a C1-C6 alkoxy group), a C1-C6 alkylcarbonyl group, a C1-C6 haloalkylcarbonyl group, a C3-C6 cycloalkylcarbonyl group, a C1-C6 alkoxy C1-C6 alkylcarbonyl group, a benzoyl group which may be substituted (the group may be monosubstituted or polysubstituted with a halogen atom or a C1-C6 alkyl group), a C7-C11 aralkylcarbonyl group which may be substituted (the group may be monosubstituted or polysubstituted with a halogen atom or a C1-C6 alkyl group), a heterocyclic carbonyl group which may be substituted (the group may be monosubstituted or polysubstituted with a halogen atom or a C1-C6 alkyl group), a heterocyclic C1-C6 alkylcarbonyl group which may be substituted (the group may be monosubstituted or polysubstituted with a halogen atom or a C1-C6 alkyl group), a C1-C6 alkoxycarbonyl group, a C2-C6 alkenyloxycarbonyl group, a C1-C6 alkoxy C1-C6 alkoxycarbonyl group, a phenoxycarbonyl group which may be substituted (the group may be monosubstituted or polysubstituted with a halogen atom or a C1-C6 alkyl group), a C7-C11 aralkyloxycarbonyl group which may be substituted (the group may be monosubstituted or polysubstituted with a halogen atom or a C1-C6 alkyl group), a heterocyclic C1-C6 alkoxycarbonyl group which may be substituted (the group may be monosubstituted or polysubstituted with a halogen atom or a C1-C6 alkyl group), a C1-C6 alkylaminocarbonyl group, a di-C1-C6 alkylaminocarbonyl group wherein the di-C1-C6 alkyl groups may be same or different, a C1-C6 alkylsulfonyl group, a C1-C6 haloalkylsulfonyl group, a C3-C6 cycloalkylsulfonyl group, a phenylsulfonyl group which may be substituted (the group may be monosubstituted or polysubstituted with a halogen atom or a C1-C6 alkyl group) or a C7-C11 aralkylsulfonyl group which may be substituted (the group may be monosubstituted or polysubstituted with a halogen atom or a C1-C6 alkyl group);

$R^3$ is a hydrogen atom, a C1-C6 alkyl group which may be substituted with a fluorine atom or a C3-C6 cycloalkyl group;

$R^4$ is a hydrogen atom, a C1-C15 alkyl group, a C1-C15 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 alkylthio C1-C6 alkyl group, a phenyl group which may be substituted (the group may be monosubstituted or polysubstituted with a halogen atom, a C1-C6 alkyl group or a C1-C6 alkoxy group), a C7-C11 aralkyl group which may be substituted (the group may be monosubstituted or polysubstituted with a halogen atom, cyano, nitro, a C1-C6 alkyl group, a C1-C6 haloalkyl group, a C1-C6 alkoxy group, a C1-C6 haloalkoxy group, a C1-C6 alkylthio group or a C1-C6 haloalkylthio group), an indanyl group which may be substituted (the group may be monosubstituted or polysubstituted with a halogen atom, a C1-C6 alkyl group or a C1-C6 alkoxy group), a tetrahydronaphthyl group which may be substituted (the group may be monosubstituted or polysubstituted with a halogen atom, a C1-C6 alkyl group or a C1-C6 alkoxy group), a heterocyclic C1-C6 alkyl group which may be substituted (the group may be monosubstituted or polysubstituted with a halogen atom, a C1-C6 alkyl group or a C1-C6 alkoxy group), a phenoxy C1-C6 alkyl group which may be substituted (the group may be monosubstituted or polysubstituted with a halogen atom, a C1-C6 alkyl group or a C1-C6 alkoxy group), a C7-C11 aralkyloxy C1-C6 alkyl group which may be substituted (the group may be monosubstituted or polysubstituted with a halogen atom, a C1-C6 alkyl group or a C1-C6 alkoxy group), a C1-C6 alkylcarbonyl group, a di-C1-C6 alkylaminocarbonyl group wherein the di-C1-C6 alkyl groups may be same or different, a C1-C6 alkylsulfonyl group or a phenylsulfonyl group which may be substituted (the group may be monosubstituted or polysubstituted with a halogen atom, a C1-C6 alkyl group or a C1-C6 alkoxy group);

X is a hydrogen atom or a halogen atom; and n is an integer of 1 to 4 wherein X's may be different from each other when n represents an integer of 2 to 4.

[5] A herbicide containing the isoxazolin-5-one derivative according to any one of [1] to [4] as an active ingredient.

Effects of Invention

The novel isoxazolin-5-one derivatives of the invention represented by the formula (1) above exhibit an excellent herbicide effect.

DESCRIPTION OF EMBODIMENTS

The isoxazolin-5-one derivatives related to the compounds of the invention, the production methods thereof and the herbicides containing the compounds as active ingredients are explained specifically.

The carbon atom number described in each of a group below does not include the carbon in the cyano group when the group has a cyano group. Moreover, the carbonyl carbon in a group containing carbonyl, such as a C1-C6 alkylcarbonyl group or a (C1-C6) alkoxycarbonyl group, is not included, either.

In the isoxazolin-5-one derivatives represented by the formula (1) of the invention, examples of the halogen atom or the halogen atom as a substituent include elements of fluorine, chlorine, bromine or iodine. The number of the halogen atom(s) as a substituent may be one, or two or more, and when the number is two or more, the halogen atoms may be the same or different from each other. The position of substitution with the halogen atom may be any position.

Examples of the C1-C6 haloalkyl group represented by $R^1$, $R^2$ or $R^3$ or the C1-C6 haloalkyl group as a substituent include monochloromethyl group, monofluoromethyl group, difluoromethyl group, trifluoromethyl group, 2,2,2-trifluoroethyl group, 2-chloroethyl group, trichloromethyl group, 1-fluoroethyl group, 2-fluoroethyl group, 6-fluorohexyl group and the like. The number of the C1-C6 haloalkyl group(s) as a substituent may be one, two or more, and when the number is two or more, the C1-C6 haloalkyl groups may be the same or different from each other. The position of substitution with the C1-C6 haloalkyl group may be any position.

Examples of the C1-C6 alkyl group represented by $R^2$, $R^3$ or X or the C1-C6 alkyl group as a substituent include methyl group, ethyl group, n-propyl group, isopropyl group, n-butyl group, isobutyl group, sec-butyl group, tert-butyl group, n-pentyl group, neopentyl group, 2-pentyl group, 3-pentyl group, tert-pentyl group, n-hexyl group, isohexyl group, 2-hexyl group, 3-hexyl group and the like. The number of the C1-C6 alkyl group(s) as a substituent may be one, two or more, and when the number is two or more, the C1-C6 alkyl groups may be the same or different from each other. The position of substitution with the C1-C6 alkyl group may be any position.

Examples of the C2-C6 alkenyl group represented by $R^2$ or $R^4$ include vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, 5-hexenyl group and the like.

Examples of the C2-C6 alkynyl group represented by $R^2$ or $R^4$ include ethynyl group, 1-propynyl group, propargyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, 1,1-dimethyl-2-butynyl group and the like.

Examples of the C1-C6 alkoxy C1-C6 alkyl group represented by $R^2$ or $R^4$ include methoxymethyl group, ethoxymethyl group, n-propoxymethyl group, isopropoxymethyl group, n-butoxymethyl group, sec-butoxymethyl group, tert-butoxymethyl group, 1-pentyloxymethyl group, 1-hexyloxymethyl group, 2-methoxyethyl group, 2-ethoxyethyl group, 2-isopropoxyethyl group, 2-isobutoxyethyl group, 3-methoxypropyl group, 2-methoxypropyl group, 2-methoxy-1-methylethyl group, 2-methoxy-1-ethylethyl group, 2-ethoxy-1-methylethyl group, 2-ethoxy-propyl group, 3-methoxy-1-methylpropyl group and the like.

Examples of the C1-C6 haloalkoxy C1-C6 alkyl group represented by $R^2$ or $R^4$ include trifluoromethoxymethyl group, 2,2,2-trifluoroethoxymethyl group, 2-(2,2,2-trifluoroethoxy)ethyl group and the like.

Examples of the C1-C6 alkoxy C1-C6 alkoxy C1-C6 alkyl group represented by $R^2$ or $R^4$ include methoxyethoxymethyl group, ethoxyethoxymethyl group, methoxyethoxyethyl group, ethoxyethoxyethyl group and the like.

Examples of the C1-C6 alkylthio C1-C6 alkyl group represented by $R^2$ or $R^4$ include methylthiomethyl group, ethylthiomethyl group, n-propylthiomethyl group, isopropylthiomethyl group, n-butylthiomethyl group, sec-butylthiomethyl group, tert-butylthiomethyl group, 1-pentylthioethyl group, 1-hexylthiomethyl group, 2-methylthioethyl group, 2-ethylthioethyl group, 2-isopropylthioethyl group, 2-isobutylthioethyl group, 3-methylthiopropyl group, 2-methylthiopropyl group, 2-methylthio-1-methylethyl group, 2-methylthio-1-methylpropyl group and the like.

Examples of the C1-C6 alkylcarbonyl C1-C6 alkyl group represented by $R^2$ or $R^4$ include 2-oxopropyl group, 2-oxobutyl group, 3-oxobutyl group and the like.

Examples of the C7-C11 aralkyl group moiety of the C7-C11 aralkyl group which may be substituted and is represented by $R^2$ or $R^4$ include benzyl group, 1-phenethyl group, 2-phenethyl group, 1-phenylpropyl group, 2-phenylpropyl group, 3-phenylpropyl group, 1-phenyl-2-methylpropyl group, 1-phenylbutyl group, 1-phenylpentyl group, 1-phenylhexyl group, 2-phenyl-1-methylethyl group and the like.

Examples of the phenoxy C1-C6 alkyl group moiety of the phenoxy C1-C6 alkyl group which may be substituted and is represented by $R^2$ or $R^4$ include 2-phenoxyethyl group, 2-phenoxypropyl group, 3-phenoxypropyl group, 2-phenoxybutyl group, 3-phenoxybutyl group, 4-phenoxybutyl group and the like.

Examples of the C7-C11 aralkyloxy C1-C6 alkyl group moiety of the C7-C11 aralkyloxy C1-C6 alkyl group which may be substituted and is represented by $R^2$ or $R^4$ include benzyloxymethyl group, 1-phenethyloxymethyl group, 2-phenethyloxymethyl group, 1-phenylpropoxymethyl group, 2-phenylpropoxymethyl group, 3-phenylpropoxymethyl group, benzyloxyethyl group and the like.

Examples of the phenylcarbonyl C1-C6 alkyl group moiety of the phenylcarbonyl C1-C6 alkyl group which may be substituted and is represented by $R^2$ or $R^4$ include phenacyl group, 1-phenyl-1-oxopropyl group, 1-phenyl-2-oxopropyl group and the like.

Examples of the C1-C6 alkylcarbonyl group represented by $R^2$ or $R^4$ include acetyl group, ethylcarbonyl group, n-propylcarbonyl group, isopropylcarbonyl group, n-butylcarbonyl group, isobutylcarbonyl group, sec-butylcarbonyl group, tert-butylcarbonyl group, 1-pentylcarbonyl group, 1-hexylcarbonyl group and the like.

Examples of the C1-C6 haloalkylcarbonyl group represented by $R^2$ include monofluoromethylcarbonyl group, difluoromethylcarbonyl group, trifluoromethylcarbonyl group, 2,2,2-trifluoroethylcarbonyl group, 2-chloroethylcarbonyl group, trichloromethylcarbonyl group, 1-fluoroethylcarbonyl group, 2-fluoroethylcarbonyl group, 6-fluorohexylcarbonyl group and the like.

Examples of the C2-C6 alkenylcarbonyl group represented by $R^2$ include acryloyl group, methacryloyl group and the like.

Examples of the C2-C6 alkynylcarbonyl group represented by $R^2$ include propiolyl group, methylpropiolyl group and the like.

Examples of the C3-C6 cycloalkylcarbonyl group represented by $R^2$ include cyclopropanecarbonyl group, 1-methylcyclopropanecarbonyl group, 2-methylcyclopropanecarbonyl group, 2,2-dimethylcyclopropanecarbonyl group, cyclobutanecarbonyl group, cyclopentanecarbonyl group, cyclohexanecarbonyl group and the like.

Examples of the C3-C6 cycloalkyl C1-C6 alkylcarbonyl group represented by $R^2$ include cyclopropylmethylcarbonyl group, cyclopropylethylcarbonyl group, 1-methylcyclopropylmethylcarbonyl group, 2-methylcyclopropylmethylcarbonyl group, 2,2-dimethylcyclopropylmethylcarbonyl group, cyclobutylmethylcarbonyl group, cyclopentylmethylcarbonyl group, cyclohexylmethylcarbonyl group and the like.

Examples of the C1-C6 alkoxy C1-C6 alkylcarbonyl group represented by $R^2$ include methoxymethylcarbonyl group, ethoxymethylcarbonyl group, n-propoxymethylcarbonyl group, isopropoxymethylcarbonyl group, n-butoxymethylcarbonyl group, sec-butoxymethylcarbonyl group, tert-butoxymethylcarbonyl group, 1-pentyloxymethylcarbonyl group, 2-methoxyethylcarbonyl group, 1-hexyloxymethylcarbonyl group, 2-methoxyethylcarbonyl group, 2-ethoxyethylcarbonyl group, 2-isopropoxyethylcarbonyl group, 2-isobutoxyethylcarbonyl group, 3-methoxypropylcarbonyl group, 2-methoxypropylcarbonyl group, 2-methoxy-1-methylethylcarbonyl group and the like.

Examples of the C1-C6 haloalkoxy C1-C6 alkylcarbonyl group represented by $R^2$ include trifluoromethoxymethylcarbonyl group, 2,2,2-trifluoroethoxymethylcarbonyl group, 2-(2,2,2-trifluoroethoxy)ethylcarbonyl group and the like.

Examples of the C1-C6 alkoxy C1-C6 alkoxy C1-C6 alkylcarbonyl group represented by $R^2$ include methoxyethoxymethylcarbonyl group, ethoxyethoxymethylcarbonyl group, methoxyethoxyethylcarbonyl group, ethoxyethoxyethylcarbonyl group and the like.

Examples of the C1-C6 alkylthio C1-C6 alkylcarbonyl group represented by $R^2$ include methylthiomethylcarbonyl group, ethylthiomethylcarbonyl group, n-propylthiomethylcarbonyl group, isopropylthiomethylcarbonyl group, n-butylthiomethylcarbonyl group, sec-butylthiomethylcarbonyl group, tert-butylthiomethylcarbonyl group, 1-pentylthiomethylcarbonyl group, 1-hexylthiomethylcarbonyl group, 2-methylthioethylcarbonyl group, 2-ethylthioethylcarbonyl group, 2-isopropylthioethylcarbonyl group, 2-isobutylthioethylcarbonyl group, 3-methylthiopropylcarbonyl group, 2-methylthiopropylcarbonyl group, 2-methylthio-1-methylethylcarbonyl group, 2-methylthio-1-methylpropylcarbonyl group and the like.

Examples of the C1-C6 haloalkylthio C1-C6 alkylcarbonyl group represented by $R^2$ include monofluoromethylthiomethylcarbonyl group, difluoromethylthiomethylcarbonyl group, trifluoromethylthiomethylcarbonyl group, 2,2,2-trifluoroethylthiomethylcarbonyl group, 2-chloroethylthiomethylcarbonyl group, trichloromethylthiomethylcarbonyl group, 1-fluoroethylthiomethylcarbonyl group, 2-fluoroethylthiomethylcarbonyl group, 6-fluorohexylthiomethylcarbonyl group and the like.

Examples of the C7-C11 aralkylcarbonyl group moiety of the C7-C11 aralkylcarbonyl group which may be substituted and is represented by $R^2$ or $R^4$ include benzylcarbonyl group, 1-phenethylcarbonyl group, 2-phenethylcarbonyl group, 1-phenylpropylcarbonyl group, 2-phenylpropylcarbonyl group, 3-phenylpropylcarbonyl group, 1-phenyl-2- methylpropylcarbonyl group, 1-phenylbutylcarbonyl group, 1-phenylpentylcarbonyl group and the like.

Examples of the heterocyclic carbonyl group moiety of the heterocyclic carbonyl group which may be substituted and is represented by $R^2$ include 2-pyridylcarbonyl group, 3-pyridylcarbonyl group, 4-pyridylcarbonyl group, 2-thienylcarbonyl group, 3-thienylcarbonyl group, 2-tetrahydrofurylcarbonyl group, 3-tetrahydrofurylcarbonyl group and the like.

Examples of the heterocyclic C1-C6 alkylcarbonyl group moiety of the heterocyclic C1-C6 alkylcarbonyl group which may be substituted and is represented by $R^2$ include 2-pyridylmethylcarbonyl group, 3-pyridylmethylcarbonyl group, 4-pyridylmethylcarbonyl group, 2-thienylmethylcarbonyl group, 3-thienylmethylcarbonyl group, 2-tetrahydrofurfurylcarbonyl group, 3-tetrahydrofurfurylcarbonyl group and the like.

Examples of the C1-C6 alkoxycarbonyl group represented by $R^2$ or $R^4$ include methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentyloxycarbonyl group, neopentyloxycarbonyl group, 2-pentyloxycarbonyl group, 3-pentyloxycarbonyl group, n-hexyloxycarbonyl group and the like.

Examples of the C1-C6 haloalkoxycarbonyl group represented by $R^2$ include trifluoromethoxycarbonyl group, 2,2,2-trifluoroethoxycarbonyl group and the like.

Examples of the C2-C6 alkenyloxycarbonyl group represented by $R^2$ include vinyloxycarbonyl group, 1-propenyloxycarbonyl group, 2-propenyloxycarbonyl group, 1-butenyloxycarbonyl group, 2-butenyloxycarbonyl group, 3-butenyloxycarbonyl group and the like.

Examples of the C2-C6 alkynyloxycarbonyl group represented by $R^2$ include ethynyloxycarbonyl group, 1-propynyloxycarbonyl group, propargyloxycarbonyl group, 1-butynyloxycarbonyl group, 2-butynyloxycarbonyl group, 3-butynyloxycarbonyl group, 1-methyl-2-propynyloxycarbonyl group, 2-methyl-3-butynyloxycarbonyl group and the like.

Examples of the C3-C6 cycloalkyloxycarbonyl group represented by $R^2$ include cyclopropyloxycarbonyl group, 1-methylcyclopropyloxycarbonyl group, 2-methylcyclopropyloxycarbonyl group, 2,2-dimethylcyclopropyloxycarbonyl group, cyclobutyloxycarbonyl group, cyclopentyloxycarbonyl group, cyclohexyloxycarbonyl group and the like.

Examples of the C3-C6 cycloalkyl C1-C6 alkoxycarbonyl group represented by $R^2$ include cyclopropylmethoxycarbonyl group, 1-methylcyclopropylmethoxycarbonyl group, 2-methylcyclopropylmethoxycarbonyl group, 2,2-dimethylcyclopropylmethoxycarbonyl group, cyclobutylmethoxycarbonyl group, cyclopentylmethoxycarbonyl group, cyclohexylmethoxycarbonyl group and the like.

Examples of the C1-C6 alkoxy C1-C6 alkoxycarbonyl group represented by $R^2$ include methoxymethoxycarbonyl group, ethoxymethoxycarbonyl group, n-propoxymethoxycarbonyl group, isopropoxymethoxycarbonyl group, n-butoxymethoxycarbonyl group, sec-butoxymethoxycarbonyl group, tert-butoxymethoxycarbonyl group, 1-pentyloxymethoxycarbonyl group, 1-hexyloxymethoxycarbonyl group, 2-methoxyethoxycarbonyl group, 2-ethoxyethoxycarbonyl group, 2-isopropoxyethoxycarbonyl group, 2-isobutoxyethoxycarbonyl group, 3-methoxypropoxycarbonyl group, 2-methoxypropoxycarbonyl group, 2-methoxy-1-methylethoxycarbonyl group and the like.

Examples of the C1-C6 haloalkoxy C1-C6 alkoxycarbonyl group represented by $R^2$ include trifluoromethoxymethoxycarbonyl group, 2,2,2-trifluoroethoxymethoxycarbonyl group, 2-(2,2,2-trifluoroethoxy)ethoxycarbonyl group and the like.

Examples of the C1-C6 alkoxy C1-C6 alkoxy C1-C6 alkoxycarbonyl group represented by $R^2$ include methoxyethoxymethoxycarbonyl group, ethoxyethoxymethoxycarbonyl group, methoxyethoxyethoxycarbonyl group, ethoxyethoxyethoxycarbonyl group and the like.

Examples of the C1-C6 alkylthio C1-C6 alkoxycarbonyl group represented by $R^2$ include methylthiomethoxycarbonyl group, ethylthiomethoxycarbonyl group, n-propylthiomethoxycarbonyl group, isopropylthiomethoxycarbonyl group, n-butylthiomethoxycarbonyl group, sec-butylthiomethoxycarbonyl group, tert-butylthiomethoxycarbonyl group, 1-pentylthiomethoxycarbonyl group, 1-hexylthiomethoxycarbonyl group, 2-methylthioethoxycarbonyl group, 2-ethylthioethoxycarbonyl group, 2-isopropylthioethoxycarbonyl group, 2-isobutylthioethoxycarbonyl group, 3-methylthiopropoxycarbonyl group, 2-methylthiopropoxycarbonyl group, 2-methylthio-1-methylethoxycarbonyl group, 2-methylthio-1-methylpropoxycarbonyl group and the like.

Examples of the C1-C6 haloalkylthio C1-C6 alkoxycarbonyl group represented by $R^2$ include monofluoromethylthiomethoxycarbonyl group, difluoromethylthiomethoxycarbonyl group, trifluoromethylthiomethoxycarbonyl group, 2,2,2-trifluoroethylthiomethoxycarbonyl group, 2-chloroethylthiomethoxycarbonyl group, trichloromethylthiomethoxycarbonyl group, 1-fluoroethylthiomethoxycarbonyl group, 2-fluoroethylthiomethoxycarbonyl group, 6-fluorohexylthiomethoxycarbonyl group, 2-(2,2,2-trifluoroethylthio)ethoxycarbonyl group and the like.

Examples of the C7-C11 aralkyloxycarbonyl group moiety of the C7-C11 aralkyloxycarbonyl group which may be substituted and is represented by $R^2$ include benzyloxycarbonyl group, 1-phenethyloxycarbonyl group, 2-phenethyloxycarbonyl group, 1-phenylpropoxycarbonyl group, 2-phenylpropoxycarbonyl group, 3-phenylpropoxycarbonyl group, 1-phenyl-2-methylpropoxycarbonyl group, 1-phenylbutoxycarbonyl group, 1-phenylpentyloxycarbonyl group and the like.

Examples of the phenoxy C1-C6 alkoxycarbonyl group moiety of the phenoxy C1-C6 alkoxycarbonyl group which may be substituted and is represented by $R^2$ include 2-phenoxyethoxycarbonyl group, 2-phenoxypropoxycarbonyl group, 3-phenoxypropoxycarbonyl group, 2-phenoxybutoxycarbonyl group, 3-phenoxybutoxycarbonyl group, 4-phenoxybutoxycarbonyl group and the like.

Examples of the heterocyclic oxycarbonyl group moiety of the heterocyclic oxycarbonyl group which may be substituted and is represented by $R^2$ include 2-pyridyloxycarbonyl group, 3-pyridyloxycarbonyl group, 4-pyridyloxycarbonyl group, 2-thienyloxycarbonyl group, 3-thienyloxycarbonyl group, 2-tetrahydrofuryloxycarbonyl group, 3-tetrahydrofuryloxycarbonyl group and the like.

Examples of the heterocyclic C1-C6 alkoxycarbonyl group moiety of the heterocyclic C1-C6 alkoxycarbonyl group which may be substituted and is represented by $R^2$ include 2-pyridylmethyloxycarbonyl group, 3-pyridylmethyloxycarbonyl group, 4-pyridylmethyloxycarbonyl group, 2-thienylmethyloxycarbonyl group, 3-thienylmethyloxycarbonyl group, 2-tetrahydrofurfuryloxycarbonyl group, 3-tetrahydrofurfuryloxycarbonyl group and the like.

Examples of the C1-C6 alkylthiocarbonyl group represented by $R^2$ include methylthiocarbonyl group, ethylthiocarbonyl group, n-propylthiocarbonyl group, isopropylthiocarbonyl group, n-butylthiocarbonyl group, isobutylthiocarbonyl group, sec-butylthiocarbonyl group, tert-butylthiocarbonyl group and the like.

Examples of the C1-C6 haloalkylthiocarbonyl group represented by $R^2$ include trifluoromethylthiocarbonyl group, 2,2,2-trifluoroethylthiocarbonyl group and the like.

Examples of the C1-C6 alkylaminocarbonyl group represented by $R^2$ or $R^4$ include methylaminocarbonyl group, ethylaminocarbonyl group, n-propylaminocarbonyl group, isopropylaminocarbonyl group, n-butylaminocarbonyl group, isobutylaminocarbonyl group, sec-butylaminocarbonyl group, tert-butylaminocarbonyl group and the like.

Examples of the C1-C6 haloalkylaminocarbonyl group represented by $R^2$ include trifluoromethylaminocarbonyl group, 2,2,2-trifluoroethylaminocarbonyl group and the like.

Examples of the di-C1-C6 alkylaminocarbonyl group wherein the di-C1-C6 alkyl groups may be same or different and the di-C1-C6 alkylaminocarbonyl group is represented by $R^2$ or $R^4$ include dimethylaminocarbonyl group, methylethylaminocarbonyl group, diethylaminocarbonyl group, di-n-propylaminocarbonyl group, methyl n-propylaminocarbonyl group, ethyl n-propylaminocarbonyl group, diisopropylaminocarbonyl group, di-n-butylaminocarbonyl group, diisobutylaminocarbonyl group, di-sec-butylaminocarbonyl group, di-tert-butylaminocarbonyl group and the like.

Examples of the C1-C6 alkylsulfonyl group represented by $R^2$ or $R^4$ include methanesulfonyl group, ethanesulfonyl group, n-propanesulfonyl group, isopropanesulfonyl group, n-butanesulfonyl group, isobutanesulfonyl group, sec-butanesulfonyl group, tert-butanesulfonyl group, n-pentanesulfonyl group and the like.

Examples of the C1-C6 haloalkylsulfonyl group represented by $R^2$ or $R^4$ include monofluoromethylsulfonyl group, difluoromethylsulfonyl group, trifluoromethylsulfonyl group, monochloromethylsulfonyl group, trichloromethylsulfonyl group, 2,2,2-trifluoroethylsulfonyl group and the like.

Examples of the C2-C6 alkenylsulfonyl group represented by $R^2$ include vinylsulfonyl group, 1-propenylsulfonyl group, 2-propenylsulfonyl group, 1-butenylsulfonyl group, 2-butenylsulfonyl group, 3-butenylsulfonyl group and the like.

Examples of the C2-C6 alkynylsulfonyl group represented by $R^2$ include ethynylsulfonyl group, 1-propynylsulfonyl group, propargylsulfonyl group, 1-butynylsulfonyl group, 2-butynylsulfonyl group, 3-butynylsulfonyl group, 1-methyl-2-propynylsulfonyl group, 2-methyl-3-butynylsulfonyl group and the like.

Examples of the C3-C6 cycloalkylsulfonyl group represented by $R^2$ include cyclopropanesulfonyl group, 1-methylcyclopropanesulfonyl group, 2-methylcyclopropanesulfonyl group, 2,2-dimethylpropanesulfonyl group, cyclobutanesulfonyl group, cyclopentanesulfonyl group, cyclohexanesulfonyl group and the like.

Examples of the C3-C6 cycloalkyl C1-C6 alkylsulfonyl group represented by $R^2$ include cyclopropylmethylsulfonyl group, 1-methylcyclopropylmethylsulfonyl group, 2-methylcyclopropylmethylsulfonyl group, 2,2-dimethylpropylmethylsulfonyl group, cyclobutylmethylsulfonyl group, cyclopentylmethylsulfonyl group, cyclohexylmethylsulfonyl group and the like.

Examples of the C1-C6 alkoxy C1-C6 alkylsulfonyl group represented by $R^2$ include methoxymethylsulfonyl group, ethoxymethylsulfonyl group, n-propoxymethylsulfonyl group, isopropoxymethylsulfonyl group, n-butoxymethylsulfonyl group, sec-butoxymethylsulfonyl group, tert-butoxymethylsulfonyl group, 1-pentyloxymethylsulfonyl group, 1-hexyloxymethylsulfonyl group, 2-methoxyethylsulfonyl group, 2-ethoxyethylsulfonyl group, 2-isopropoxyethylsulfonyl group, 2-isobutoxyethylsulfonyl group, 3-methoxypropylsulfonyl group, 2-methoxypropylsulfonyl group, 2-methoxy-1-methylethylsulfonyl group and the like.

Examples of the C7-C11 aralkylsulfonyl group moiety of the C7-C11 aralkylsulfonyl group which may be substituted and is represented by $R^2$ or $R^4$ include benzylsulfonyl group, 1-phenethylsulfonyl group, 2-phenethylsulfonyl group, 1-phenylpropylsulfonyl group, 2-phenylpropylsulfonyl group, 3-phenylpropylsulfonyl group, 1-phenyl-2-methylpropylsulfonyl group, 1-phenylbutylsulfonyl group, 1-phenylpentylsulfonyl group and the like.

Examples of the C1-C6 alkylaminosulfonyl group represented by $R^2$ include methylaminosulfonyl group, ethylaminosulfonyl group, n-propylaminosulfonyl group, isopropylaminosulfonyl group, n-butylaminosulfonyl group, isobutylaminosulfonyl group, sec-butylaminosulfonyl group, tert-butylaminosulfonyl group and the like.

Examples of the di-C1-C6 alkylaminosulfonyl group wherein the di-C1-C6 alkyl groups may be same or different and the di-C1-C6 alkylaminosulfonyl group is represented by $R^2$ include dimethylaminosulfonyl group, methylethylaminosulfonyl group, diethylaminosulfonyl group, di-n-propylaminosulfonyl group, methyl n-propylaminosulfonyl group, ethyl n-propylaminosulfonyl group, diisopropylaminosulfonyl group, di-n-butylaminosulfonyl group, diisobutylaminosulfonyl group, di-sec-butylaminosulfonyl group, di-tert-butylaminosulfonyl group and the like.

Examples of the C3-C6 cycloalkyl group represented by $R^3$ or $R^4$ include cyclopropyl group, 1-methylcyclopropyl group, 2-methylcyclopropyl group, 2,2-dimethylpropyl group, cyclobutyl group, cyclopentyl group, cyclohexyl group and the like.

Examples of the C1-C6 alkylamino group represented by $R^3$ include methylamino group, ethylamino group, n-propylamino group, isopropylamino group, n-butylamino group, isobutylamino group, sec-butylamino group, tert-butylamino group and the like.

Examples of the di-C1-C6 alkylamino group wherein the di-C1-C6 alkyl groups may be same or different and the di-C1-C6 alkylamino group is represented by $R^3$ include dimethylamino group, methylethylamino group, diethylamino group, di-n-propylamino group, methyl n-propylamino group, ethyl n-propylamino group, diisopropylamino group, di-n-butylamino group, diisobutylamino group, di-sec-butylamino group, di-tert-butylamino group and the like.

Examples of the C1-C15 alkyl group represented by $R^4$ include methyl group, ethyl group, n-propyl group, isopropyl group, 1,1-dimethylpropyl group, 1,2-dimethylpropyl group, 1-ethylpropyl group, n-butyl group, isobutyl group, sec-butyl group, tert-butyl group, 2-methylbutyl group, 3-methylbutyl group, 1-ethylbutyl group, 2-ethylbutyl group, 1,1-dimethylbutyl group, 1,2-dimethylbutyl group, 2,2-dimethylbutyl group, 2,3-dimethylbutyl group, 3,3-dimethylbutyl group, 2-ethyl-2-methylbutyl group, n-pentyl group, neopentyl group, 2-pentyl group, tert-pentyl group, 1-methylpentyl group, 2-methylpentyl group, 3-methylpentyl group, 4-methylpentyl group, 1-ethylpentyl group, 2-ethylpentyl group, n-hexyl group, 1-methylhexyl group, 2-methylhexyl group, 1-ethylhexyl group, 2-ethylhexyl group, n-heptyl group, n-octyl group, n-nonyl group, n-decyl group, n-undecyl group, n-dodecyl group, n-tridecyl group, n-tetradecyl group, n-pentadecyl group and the like.

Examples of the C1-C15 haloalkyl group represented by $R^4$ include monofluoromethyl group, difluoromethyl group, trifluoromethyl group, 2,2,2-trifluoroethyl group, 2-chloroethyl group, trichloromethyl group, 1-fluoroethyl group, 2-fluoroethyl group, 3,3,3-trifluoropropyl group, 4,4,4-trifluorobutyl group, 5,5,5-trifluoropentyl group, 6-fluorohexyl group, 6,6,6-trifluorohexyl group, 7,7,7-trifluoroheptyl group and the like.

Examples of the C2-C6 haloalkenyl group represented by $R^4$ include bromovinyl group, chlorovinyl group, 3,3-dichloro-2-propenyl group, 3,3,3-trifluoro-1-propenyl group, 4,4-difluoro-3-butenyl group, 3,4,4-trifluoro-3-butenyl group and the like.

Examples of the C2-C6 haloalkynyl group represented by $R^4$ include fluoroethynyl group, 3-fluoro-2-propynyl group, 3-chloro-2-propynyl group, 3-chloro-1-propynyl group, 5-chloro-4-pentynyl group, 3,3,3-trifluoro-1-propynyl group, 3,3-difluoro-1-propynyl group, 4,4,4-trifluoro-2-butynyl group and the like.

Examples of the C3-C6 cycloalkyl C1-C6 alkyl group represented by $R^4$ include cyclopropylmethyl group, cyclopropylethyl group, 1-methylcyclopropylmethyl group, 2-methylcyclopropylmethyl group, 2,2-dimethylcyclopropylmethyl group, cyclobutylmethyl group, cyclopentylmethyl group, cyclohexylmethyl group and the like.

Examples of the C1-C6 haloalkylthio C1-C6 alkyl group represented by $R^4$ include monofluoromethylthiomethyl group, difluoromethylthiomethyl group, trifluoromethylthiomethyl group, 2,2,2-trifluoroethylthiomethyl group, 2-(2,2,2-trifluoroethylthio)ethyl group, 2-chloroethylthiomethyl group, trichloromethylthiomethyl group, 1-fluoroethylthiomethyl group, 2-fluoroethylthiomethyl group, 6-fluorohexylthiomethyl group and the like.

Examples of the C1-C6 alkylsulfinyl C1-C6 alkyl group represented by $R^4$ include methylsulfinylmethyl group, ethylsulfinylmethyl group, n-propylsulfinylmethyl group, isopropylsulfinylmethyl group, n-butylsulfinylmethyl group, isobutylsulfinylmethyl group, sec-butylsulfinylmethyl group, tert-butylsulfinylmethyl group, methylsulfinylethyl group, ethylsulfinylethyl group, n-propyl sulfinylethyl group, isopropyl sulfinylethyl group, methylsulfinylpropyl group and the like.

Examples of the C1-C6 alkylsulfonyl C1-C6 alkyl group represented by $R^4$ include methylsulfonylmethyl group, ethylsulfonylmethyl group, n-propylsulfonylmethyl group, isopropylsulfonylmethyl group, n-butylsulfonylmethyl group, isobutylsulfonylmethyl group, sec-butylsulfonylmethyl group, tert-butylsulfonylmethyl group, methylsulfonylethyl group, ethylsulfonylethyl group, n-propylsulfonylethyl group, isopropyl sulfonylethyl group, methylsulfonylpropyl group and the like.

Examples of the C1-C6 alkylamino C1-C6 alkyl group represented by $R^4$ include methylaminomethyl group, methylaminoethyl group, ethylaminoethyl group, n-propylaminoethyl group, isopropylaminoethyl group, n-butylaminoethyl group, isobutylaminoethyl group, sec-butylaminoethyl group, tert-butylaminoethyl group and the like.

Examples of the di-C1-C6 alkylamino C1-C6 alkyl group wherein the di-C1-C6 alkyl groups may be same or different and the di-C1-C6 alkylamino C1-C6 alkyl group is represented by $R^4$ include dimethylaminomethyl group, dimethylaminoethyl group, methylethylaminoethyl group, diethylaminoethyl group, di-n-propylaminoethyl group, methyl n-propylaminoethyl group, ethyl n-propylaminoethyl group, diisopropylaminoethyl group, di-n-butylaminoethyl group, diisobutylaminoethyl group, di-sec-butylaminoethyl group, di-tert-butylaminoethyl group and the like.

Examples of the indanyl group moiety of the indanyl group which may be substituted and is represented by $R^4$ include 1-indanyl group, 2-indanyl group and the like.

Examples of the tetrahydronaphthyl group moiety of the tetrahydronaphthyl group which may be substituted and is represented by $R^4$ include 1-(1,2,3,4-tetrahydronaphthyl) group, 2-(1,2,3,4-tetrahydronaphthyl) group and the like.

Examples of the heterocyclic C1-C6 alkyl group moiety of the heterocyclic C1-C6 alkyl group which may be substituted and is represented by $R^4$ include (2-oxiranyl)methyl group, (3-oxetanyl)methyl group, (2-methyl-2-oxiranyl)methyl group, (3-methyl-3-oxetanyl)methyl group, (2-tetrahydrofuryl)methyl group, (3-tetrahydrofuryl)methyl group, (2-thienyl)methyl group, (3-thienyl)methyl group, (2-pyridyl)methyl group, (3-pyridyl)methyl group, (4-pyridyl)methyl group, 1-(2-thienyl)ethyl group, 2-(2-thienyl)ethyl group, 1-(3-thienyl)ethyl group, 2-(3-thienyl) ethyl group, 1-(2-pyridyl)ethyl group, 2-(2-pyridyl)ethyl group, 1-(3-pyridyl)ethyl group, 2-(3-pyridyl)ethyl group, 1-(4-pyridyl)ethyl group, 2-(4-pyridyl)ethyl group and the like.

Examples of the C1-C6 alkoxy group represented by X or the C1-C6 alkoxy group as a substituent include methoxy group, ethoxy group, n-propoxy group, isopropoxy group, n-butoxy group, isobutoxy group, sec-butoxy group, tert-butoxy group and the like. The number of the C1-C6 alkoxy group(s) as a substituent may be one, two or more, and when the number is two or more, the C1-C6 alkoxy groups may be the same or different from each other. The position of substitution with the C1-C6 alkoxy group may be any position.

Examples of the C1-C6 haloalkoxy group as a substituent include monofluoromethoxy group, difluoromethoxy group, trifluoromethoxy group, 2,2,2-trifluoroethoxy group, 2-chloroethoxy group, trichloromethoxy group, 1-fluoroethoxy group, 2-fluoroethoxy group and the like. The number of the C1-C6 haloalkoxy group(s) as a substituent may be one, two or more, and when the number is two or more, the C1-C6 haloalkoxy groups may be the same or different from each other. The position of substitution with the C1-C6 haloalkoxy group may be any position.

Examples of the C1-C6 alkylthio group as a substituent include methylthio group, ethylthio group, n-propylthio group, isopropylthio group, n-butylthio group, isobutylthio group, sec-butylthio group, tert-butylthio group and the like. The number of the C1-C6 alkylthio group(s) as a substituent may be one, or two or more, and when the number is two or more, the C1-C6 alkylthio groups may be the same or different from each other. The position of substitution with the C1-C6 alkylthio group may be any position.

Examples of the C1-C6 haloalkylthio group as a substituent include trifluoromethylthio group, 2,2,2-trifluoroethylthio group and the like.

The number of the C1-C6 haloalkylthio group(s) as a substituent may be one, or two or more, and when the number is two or more, the C1-C6 haloalkylthio groups may be the same or different from each other. The position of substitution with the C1-C6 haloalkylthio group may be any position.

In the isoxazolin-5-one derivatives represented by the formula (1), although the combination of $R^1$ to $R^4$, X and n is not particularly limited, for example, an embodiment is as follows.

In the formula (1) above, $R^1$ is a trifluoromethyl group; $R^2$ is a hydrogen atom, a C1-C6 alkyl group, a C1-C6 alkoxy C1-C6 alkyl group, a C7-C11 aralkyl group which may be substituted (the group may be monosubstituted or polysubstituted with a halogen atom, a C1-C6 alkyl group or a C1-C6 alkoxy group), a C1-C6 alkylcarbonyl group, a C1-C6 haloalkylcarbonyl group, a C3-C6 cycloalkylcarbonyl group, a C1-C6 alkoxy C1-C6 alkylcarbonyl group, a benzoyl group which may be substituted (the group may be monosubstituted or polysubstituted with a halogen atom or a C1-C6 alkyl group), a C7-C11 aralkylcarbonyl group which may be substituted (the group may be monosubstituted or polysubstituted with a halogen atom or a C1-C6 alkyl group), a heterocyclic carbonyl group which may be substituted (the group may be monosubstituted or polysubstituted with a halogen atom or a C1-C6 alkyl group), a heterocyclic C1-C6 alkylcarbonyl group which may be substituted (the group may be monosubstituted or polysubstituted with a halogen atom or a C1-C6 alkyl group), a C1-C6 alkoxycarbonyl group, a C2-C6 alkenyloxycarbonyl group, a C1-C6 alkoxy C1-C6 alkoxycarbonyl group, a phenoxycarbonyl group which may be substituted (the group may be monosubstituted or polysubstituted with a halogen atom or a C1-C6 alkyl group), a C7-C11 aralkyloxycarbonyl group which may be substituted (the group may be monosubstituted or polysubstituted with a halogen atom or a C1-C6 alkyl group), a heterocyclic C1-C6 alkoxycarbonyl group which may be substituted (the group may be monosubstituted or polysubstituted with a halogen atom or a C1-C6 alkyl group), a C1-C6 alkylaminocarbonyl group, a di-C1-C6 alkylaminocarbonyl group wherein the di-C1-C6 alkyl groups may be same or different, a C1-C6 alkylsulfonyl group, a C1-C6 haloalkylsulfonyl group, a C3-C6 cycloalkylsulfonyl group, a phenylsulfonyl group which may be substituted (the group may be monosubstituted or polysubstituted with a halogen atom or a C1-C6 alkyl group) or a C7-C11 aralkylsulfonyl group which may be substituted (the group may be monosubstituted or polysubstituted with a halogen atom or a C1-C6 alkyl group); $R^3$ is a hydrogen atom, a C1-C6 alkyl group which may be substituted with a fluorine atom or a C3-C6 cycloalkyl group; $R^4$ is a hydrogen atom, a C1-C15 alkyl group, a C1-C15 haloalkyl group, a C2-C6 alkenyl group, a C2-C6 alkynyl group, a C3-C6 cycloalkyl group, a C3-C6 cycloalkyl C1-C6 alkyl group, a C1-C6 alkoxy C1-C6 alkyl group, a C1-C6 alkylthio C1-C6 alkyl group, a phenyl group which may be substituted (the group may be monosubstituted or polysubstituted with a halogen atom, a C1-C6 alkyl group or a C1-C6 alkoxy group), a C7-C11 aralkyl group which may be substituted (the group may be monosubstituted or polysubstituted with a halogen atom, cyano, nitro, a C1-C6 alkyl group, a C1-C6 haloalkyl group, a C1-C6 alkoxy group, a C1-C6 haloalkoxy group, a C1-C6 alkylthio group or a C1-C6 haloalkylthio group), an indanyl group which may be substituted (the group may be monosubstituted or polysubstituted with a halogen atom, a C1-C6 alkyl group or a C1-C6 alkoxy group), a tetrahydronaphthyl group which may be substituted (the group may be monosubstituted or polysubstituted with a halogen atom, a C1-C6 alkyl group or a C1-C6 alkoxy group), a heterocyclic C1-C6 alkyl group which may be substituted (the group may be monosubstituted or polysubstituted with a halogen atom, a C1-C6 alkyl group or a C1-C6 alkoxy group), a phenoxy C1-C6 alkyl group which may be substituted (the group may be monosubstituted or polysubstituted with a halogen atom, a C1-C6 alkyl group or a C1-C6 alkoxy group), a C7-C11 aralkyloxy C1-C6 alkyl group which may be substituted (the group may be monosubstituted or polysubstituted with a halogen atom, a C1-C6 alkyl group or a C1-C6 alkoxy group), a C1-C6 alkylcarbonyl group, a di-C1-C6 alkylaminocarbonyl group wherein the di-C1-C6 alkyl groups may be same or different, a C1-C6 alkylsulfonyl group or a phenylsulfonyl group which may be substituted (the group may be monosubstituted or polysubstituted with a halogen atom, a C1-C6 alkyl group or a C1-C6 alkoxy group); X is a hydrogen atom or a halogen atom; and n is an integer of 1 to 4 (wherein X's may be different from each other when n represents an integer of 2 to 4.)

Representative examples of the isoxazolin-5-one derivatives represented by the formula (1) are shown together in Table 1 below, but the isoxazolin-5-one derivatives are not limited to these compounds. These compounds include compounds including optical isomers, an E-form and a Z-form. The compound numbers are referred to in the following paragraphs.

The symbols below in the tables stand for the corresponding groups as follows: "H" stands for hydrogen atom; "Me" stands for methyl group; "Et" stands for ethyl group; "n-Pr" stands for normal propyl group; "i-Pr" stands for isopropyl group; "c-Pr" stands for cyclopropyl group; "n-Bu" stands for normal butyl group; "s-Bu" stands for sec-butyl group; "i-Bu" stands for isobutyl group; "t-Bu" stands for tert-butyl group; "c-Bu" stands for cyclobutyl group; "n-Pen" stands for normal pentyl group; "c-Pen" stands for cyclopentyl group; "n-Hex" stands for normal hexyl group; "c-Hex" stands for cyclohexyl group; "Ph" stands for phenyl group; "Bz" stands for benzoyl group; and "Np" stands for naphthyl group.

TABLE 1

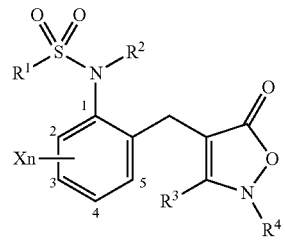

| No. | $R^1$ | $R^2$ | $R^3$ | $R^4$ | Xn |
|---|---|---|---|---|---|
| 1-1 | $CH_2Cl$ | H | Me | i-Pr | H |
| 1-2 | $CH_2Cl$ | H | Me | s-Bu | H |
| 1-3 | $CH_2Cl$ | COMe | Me | s-Bu | H |
| 1-4 | $CH_2Cl$ | $CO_2Me$ | Me | s-Bu | H |
| 1-5 | $CH_2Cl$ | $CO_2Et$ | Me | s-Bu | H |
| 1-6 | $CH_2Cl$ | $SO_2Me$ | Me | s-Bu | H |
| 1-7 | $CH_2Cl$ | $SO_2CH_2Cl$ | Me | s-Bu | H |
| 1-8 | $CH_2Cl$ | $SO_2CF_3$ | Me | s-Bu | H |

TABLE 1-continued

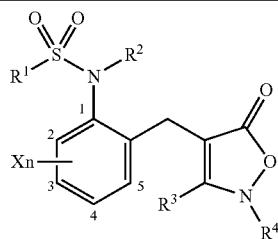

| No. | R¹ | R² | R³ | R⁴ | Xn |
|---|---|---|---|---|---|
| 1-9 | CH₂Cl | H | Me | i-Bu | H |
| 1-10 | CCl₃ | H | Me | i-Pr | H |
| 1-11 | CCl₃ | H | Me | s-Bu | H |
| 1-12 | CCl₃ | H | Me | i-Bu | H |
| 1-13 | CH₂F | H | Me | i-Pr | H |
| 1-14 | CH₂F | H | Me | s-Bu | H |
| 1-15 | CH₂F | H | Me | i-Bu | H |
| 1-16 | CF₂H | H | Me | i-Pr | H |
| 1-17 | CF₂H | H | Me | s-Bu | Hz |
| 1-18 | CF₂H | COMe | Me | s-Bu | H |
| 1-19 | CF₂H | CO₂Me | Me | s-Bu | H |
| 1-20 | CF₂H | CO₂Et | Me | s-Bu | H |
| 1-21 | CF₂H | SO₂Me | Me | s-Bu | H |
| 1-22 | CF₂H | SO₂CHF₂ | Me | s-Bu | H |
| 1-23 | CF₂H | SO₂CF₃ | Me | s-Bu | H |
| 1-24 | CF₂H | H | Me | i-Bu | H |
| 1-25 | CF₂H | H | Me | CH(Me)CH₂OMe | H |
| 1-26 | CF₃ | H | Me | i-Pr | 4-F |
| 1-27 | CF₃ | H | Me | s-Bu | 4-F |
| 1-28 | CF₃ | H | Me | i-Bu | 4-F |
| 1-29 | CF₃ | SO₂CF₃ | Me | i-Bu | 4-F |
| 1-30 | CF₃ | H | Me | CH(Me)CH₂OMe | 4-F |
| 1-31 | CF₃ | H | Me | CH₂Ph | 4-F |
| 1-32 | CF₃ | SO₂CF₃ | Me | CH₂Ph | 4-F |
| 1-33 | CF₃ | H | Me | i-Pr | 2-Cl |
| 1-34 | CF₃ | H | Me | s-Bu | 2-Cl |
| 1-35 | CF₃ | H | Me | i-Bu | 2-Cl |
| 1-36 | CF₃ | H | Me | CH(Me)CH₂OMe | 2-Cl |
| 1-37 | CF₃ | H | Me | i-Pr | 3-Cl |
| 1-38 | CF₃ | H | Me | s-Bu | 3-Cl |
| 1-39 | CF₃ | H | Me | i-Bu | 3-Cl |
| 1-40 | CF₃ | H | Me | CH(Me)CH₂OMe | 3-Cl |
| 1-41 | CF₃ | H | Me | i-Pr | 4-Cl |
| 1-42 | CF₃ | H | Me | s-Bu | 4-Cl |
| 1-43 | CF₃ | H | Me | i-Bu | 4-Cl |
| 1-44 | CF₃ | H | Me | CH(Me)CH₂OMe | 4-Cl |
| 1-45 | CF₃ | H | Me | CH₂Ph | 4-Cl |
| 1-46 | CF₃ | H | Me | i-Pr | 5-Cl |
| 1-47 | CF₃ | SO₂CF₃ | Me | i-Pr | 5-Cl |
| 1-48 | CF₃ | H | Me | s-Bu | 5-Cl |
| 1-49 | CF₃ | H | Me | i-Bu | 5-Cl |
| 1-50 | CF₃ | H | Me | CH(Me)CH₂OMe | 5-Cl |
| 1-51 | CF₃ | H | Me | s-Bu | 3,4-Cl₂ |
| 1-52 | CF₃ | H | Me | s-Bu | 4-Br |
| 1-53 | CF₃ | H | Me | s-Bu | 4-I |
| 1-54 | CF₃ | H | Me | s-Bu | 4-Me |
| 1-55 | CF₃ | H | Me | CH(Me)CH₂OMe | 4-Me |
| 1-56 | CF₃ | H | Me | s-Bu | 4-MeO |
| 1-57 | CF₃ | H | Me | CH(Me)CH₂OMe | 4-MeO |
| 1-58 | CF₃ | H | H | s-Bu | H |
| 1-59 | CF₃ | H | F | s-Bu | H |
| 1-60 | CF₃ | H | Cl | s-Bu | H |
| 1-61 | CF₃ | H | Br | s-Bu | H |
| 1-62 | CF₃ | H | I | s-Bu | H |
| 1-63 | CF₃ | H | Et | i-Pr | H |
| 1-64 | CF₃ | H | Et | s-Bu | H |
| 1-65 | CF₃ | H | Et | i-Bu | H |
| 1-66 | CF₃ | H | Et | CH(Me)CH₂OMe | H |
| 1-67 | CF₃ | H | n-Pr | s-Bu | H |
| 1-68 | CF₃ | H | i-Pr | i-Pr | H |
| 1-69 | CF₃ | SO₂CF₃ | i-Pr | i-Pr | H |
| 1-70 | CF₃ | H | i-Pr | s-Bu | H |
| 1-71 | CF₃ | H | i-Pr | i-Bu | H |
| 1-72 | CF₃ | H | i-Pr | CH(Me)CH₂OMe | H |
| 1-73 | CF₃ | H | n-Bu | s-Bu | H |
| 1-74 | CF₃ | H | i-Bu | s-Bu | H |

TABLE 1-continued

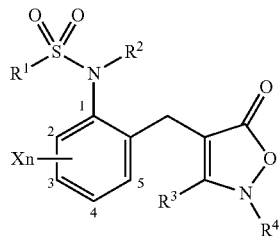

| No. | R¹ | R² | R³ | R⁴ | Xn |
|---|---|---|---|---|---|
| 1-75 | $CF_3$ | H | s-Bu | s-Bu | H |
| 1-76 | $CF_3$ | H | t-Bu | s-Bu | H |
| 1-77 | $CF_3$ | H | $CF_2H$ | s-Bu | H |
| 1-78 | $CF_3$ | H | $CF_3$ | Me | H |
| 1-79 | $CF_3$ | H | $CF_3$ | i-Pr | H |
| 1-80 | $CF_3$ | H | $CF_3$ | s-Bu | H |
| 1-81 | $CF_3$ | H | $CF_3$ | i-Bu | H |
| 1-82 | $CF_3$ | H | $CF_3$ | $CH(Me)CH_2OMe$ | H |
| 1-83 | $CF_3$ | H | c-Pr | i-Pr | H |
| 1-84 | $CF_3$ | $SO_2CF_3$ | c-Pr | i-Pr | H |
| 1-85 | $CF_3$ | H | c-Pr | s-Bu | H |
| 1-86 | $CF_3$ | H | c-Pr | i-Bu | H |
| 1-87 | $CF_3$ | H | c-Pr | $CH(Me)CH_2OMe$ | H |
| 1-88 | $CF_3$ | H | c-Bu | s-Bu | H |
| 1-89 | $CF_3$ | H | c-Hex | s-Bu | H |
| 1-90 | $CF_3$ | H | Ph | s-Bu | H |
| 1-91 | $CF_3$ | H | 4-ClPh | s-Bu | H |
| 1-92 | $CF_3$ | H | 4-MePh | s-Bu | H |
| 1-93 | $CF_3$ | H | $NH_2$ | s-Bu | H |
| 1-94 | $CF_3$ | H | NHMe | s-Bu | H |
| 1-95 | $CF_3$ | H | $NMe_2$ | s-Bu | H |
| 1-96 | $CF_3$ | H | Me | H | H |
| 1-97 | $CF_3$ | H | Me | Me | H |
| 1-98 | $CF_3$ | H | Me | Et | H |
| 1-99 | $CF_3$ | H | Me | n-Pr | H |
| 1-100 | $CF_3$ | H | Me | i-Pr | H |
| 1-101 | $CF_3$ | H | Me | t-Bu | H |
| 1-102 | $CF_3$ | H | Me | s-Bu | H |
| 1-103 | $CF_3$ | H | Me | $CH(Et)CH_2CH_3$ | H |
| 1-104 | $CF_3$ | H | Me | $C(Me)_2CH_2CH_3$ | H |
| 1-105 | $CF_3$ | H | Me | i-Bu | H |
| 1-106 | $CF_3$ | H | Me | $CH_2C(Me)_2CH_3$ | H |
| 1-107 | $CF_3$ | H | Me | $CH(Me)CH(Me)CH_3$ | H |
| 1-108 | $CF_3$ | H | Me | n-Bu | H |
| 1-109 | $CF_3$ | H | Me | $CH(Me)CH_2CH_2CH_3$ | H |
| 1-110 | $CF_3$ | H | Me | $CH(Et)CH_2CH_2CH_3$ | H |
| 1-111 | $CF_3$ | H | Me | $C(Me)_2CH_2CH_2CH_3$ | H |
| 1-112 | $CF_3$ | H | Me | $CH_2CH(Me)CH_2CH_3$ | H |
| 1-113 | $CF_3$ | H | Me | $CH_2CH(Et)CH_2CH_3$ | H |
| 1-114 | $CF_3$ | H | Me | $CH_2C(Me)_2CH_2CH_3$ | H |
| 1-115 | $CF_3$ | H | Me | $CH_2CH_2CH(Me)CH_3$ | H |
| 1-116 | $CF_3$ | H | Me | $CH_2CH_2C(Me)_2CH_3$ | H |
| 1-117 | $CF_3$ | H | Me | $CH(Me)CH(Me)CH_2CH_3$ | H |
| 1-118 | $CF_3$ | H | Me | $CH_2CH(Me)CH(Me)CH_3$ | H |
| 1-119 | $CF_3$ | H | Me | n-Pen | H |
| 1-120 | $CF_3$ | H | Me | $CH(Me)CH_2CH_2CH_2CH_3$ | H |
| 1-121 | $CF_3$ | H | Me | $CH(Et)CH_2CH_2CH_2CH_3$ | H |
| 1-122 | $CF_3$ | H | Me | $CH_2CH(Me)CH_2CH_2CH_3$ | H |
| 1-123 | $CF_3$ | H | Me | $CH_2CH(Et)CH_2CH_2CH_3$ | H |
| 1-124 | $CF_3$ | H | Me | $CH_2CH_2CH(Me)CH_2CH_3$ | H |
| 1-125 | $CF_3$ | H | Me | $CH_2CH_2CH_2CH(Me)CH_3$ | H |
| 1-126 | $CF_3$ | H | Me | n-Hex | H |
| 1-127 | $CF_3$ | H | Me | $CH(Me)CH_2CH_2CH_2CH_2CH_3$ | H |
| 1-128 | $CF_3$ | H | Me | $CH(Et)CH_2CH_2CH_2CH_2CH_3$ | H |
| 1-129 | $CF_3$ | H | Me | $CH_2CH(Me)CH_2CH_2CH_2CH_3$ | H |
| 1-130 | $CF_3$ | H | Me | $CH_2CH(Et)CH_2CH_2CH_2CH_3$ | H |
| 1-131 | $CF_3$ | H | Me | $(CH_2)_7CH_3$ | H |
| 1-132 | $CF_3$ | H | Me | $(CH_2)_{13}CH_3$ | H |
| 1-133 | $CF_3$ | H | Me | $CH_2CH_2Cl$ | H |
| 1-134 | $CF_3$ | H | Me | $CH_2CF_3$ | H |
| 1-135 | $CF_3$ | H | Me | $CH_2CH=CH_2$ | H |
| 1-136 | $CF_3$ | H | Me | $CH(Me)CH=CH_2$ | H |
| 1-137 | $CF_3$ | H | Me | $CH_2C(Me)=CH_2$ | H |
| 1-138 | $CF_3$ | H | Me | $CH_2C\equiv CH$ | H |
| 1-139 | $CF_3$ | H | Me | c-Pr | H |
| 1-140 | $CF_3$ | H | Me | c-Bu | H |

TABLE 1-continued

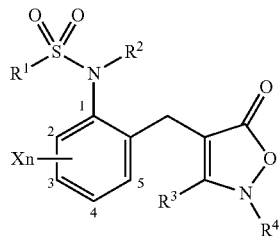

| No. | R¹ | R² | R³ | R⁴ | Xn |
|---|---|---|---|---|---|
| 1-141 | CF₃ | H | Me | c-Pen | H |
| 1-142 | CF₃ | H | Me | c-Hex | H |
| 1-143 | CF₃ | H | Me | CH₂c-Pr | H |
| 1-144 | CF₃ | H | Me | CH(Me)c-Pr | H |
| 1-145 | CF₃ | H | Me | CH₂(1-Me-c-Pr) | H |
| 1-146 | CF₃ | H | Me | CH₂c-Hex | H |
| 1-147 | CF₃ | H | Me | CH₂OMe | H |
| 1-148 | CF₃ | H | Me | CH₂CH₂OMe | H |
| 1-149 | CF₃ | H | Me | CH(Me)CH₂OMe | H |
| 1-150 | CF₃ | H | Me | CH(Et)CH₂OMe | H |
| 1-151 | CF₃ | H | Me | CH₂CH(Me)OMe | H |
| 1-152 | CF₃ | H | Me | CH₂CH₂OEt | H |
| 1-153 | CF₃ | H | Me | CH(Me)CH₂OEt | H |
| 1-154 | CF₃ | H | Me | CH₂CH(Me)OEt | H |
| 1-155 | CF₃ | H | Me | CH₂CH₂Oi-Pr | H |
| 1-156 | CF₃ | H | Me | CH₂CH₂Oi-Bu | H |
| 1-157 | CF₃ | H | Me | CH₂CH₂CH₂OMe | H |
| 1-158 | CF₃ | H | Me | CH(Me)CH₂CH₂OMe | H |
| 1-159 | CF₃ | H | Me | CH₂CH₂OCH₂CF₃ | H |
| 1-160 | CF₃ | H | Me | CH₂CH₂OCH₂CH₂OMe | H |
| 1-161 | CF₃ | H | Me | CH₂SMe | H |
| 1-162 | CF₃ | H | Me | CH₂CH₂SMe | H |
| 1-163 | CF₃ | H | Me | CH(Me)CH₂SMe | H |
| 1-164 | CF₃ | H | Me | CH₂CH(Me)SMe | H |
| 1-165 | CF₃ | H | Me | CH₂CH₂SEt | H |
| 1-166 | CF₃ | H | Me | CH₂CH₂Si-Pr | H |
| 1-167 | CF₃ | H | Me | CH₂CH₂CH₂SMe | H |
| 1-168 | CF₃ | H | Me | CH₂CH₂SCH₂CF₃ | H |
| 1-169 | CF₃ | H | Me | CH₂CH₂SOMe | H |
| 1-170 | CF₃ | H | Me | CH₂CH₂SO₂Me | H |
| 1-171 | CF₃ | H | Me | CH₂CH₂NHMe | H |
| 1-172 | CF₃ | H | Me | CH₂CH₂NMe₂ | H |
| 1-173 | CF₃ | H | Me | CH₂COMe | H |
| 1-174 | CF₃ | H | Me | Ph | H |
| 1-175 | CF₃ | H | Me | 2-ClPh | H |
| 1-176 | CF₃ | H | Me | 3-ClPh | H |
| 1-177 | CF₃ | H | Me | 4-ClPh | H |
| 1-178 | CF₃ | H | Me | 4-MePh | H |
| 1-179 | CF₃ | H | Me | 4-MeOPh | H |
| 1-180 | CF₃ | H | Me | CH₂Ph | H |
| 1-181 | CF₃ | H | Me | CH₂(2-FPh) | H |
| 1-182 | CF₃ | H | Me | CH₂(3-FPh) | H |
| 1-183 | CF₃ | H | Me | CH₂(4-FPh) | H |
| 1-184 | CF₃ | H | Me | CH₂(2-ClPh) | H |
| 1-185 | CF₃ | H | Me | CH₂(3-ClPh) | H |
| 1-186 | CF₃ | H | Me | CH₂(4-ClPh) | H |
| 1-187 | CF₃ | H | Me | CH₂(4-BrPh) | H |
| 1-188 | CF₃ | H | Me | CH₂(4-IPh) | H |
| 1-189 | CF₃ | H | Me | CH₂(4-CNPh) | H |
| 1-190 | CF₃ | H | Me | CH₂(4-NO₂Ph) | H |
| 1-191 | CF₃ | H | Me | CH₂(4-MePh) | H |
| 1-192 | CF₃ | H | Me | CH₂(4-t-BuPh) | H |
| 1-193 | CF₃ | H | Me | CH₂(3-CF₃Ph) | H |
| 1-194 | CF₃ | H | Me | CH₂(4-CF₃Ph) | H |
| 1-195 | CF₃ | H | Me | CH₂(4-MeOPh) | H |
| 1-196 | CF₃ | H | Me | CH₂(4-CF₃OPh) | H |
| 1-197 | CF₃ | H | Me | CH₂(4-MeSPh) | H |
| 1-198 | CF₃ | H | Me | CH₂(4-CF₃SPh) | H |
| 1-199 | CF₃ | H | Me | CH₂(2,4-F₂Ph) | H |
| 1-200 | CF₃ | H | Me | CH₂(3,4-F₂Ph) | H |
| 1-201 | CF₃ | H | Me | CH₂(2-Cl-4-FPh) | H |
| 1-202 | CF₃ | H | Me | CH₂(3-Cl-4-FPh) | H |
| 1-203 | CF₃ | H | Me | CH(Me)Ph | H |
| 1-204 | CF₃ | H | Me | CH(Me)(4-FPh) | H |
| 1-205 | CF₃ | H | Me | CH(Me)(2-ClPh) | H |
| 1-206 | CF₃ | H | Me | CH(Me)(3-ClPh) | H |

TABLE 1-continued

| No. | R¹ | R² | R³ | R⁴ | Xn |
|---|---|---|---|---|---|
| 1-207 | $CF_3$ | H | Me | CH(Me)(4-ClPh) | H |
| 1-208 | $CF_3$ | H | Me | CH(Me)(4-MePh) | H |
| 1-209 | $CF_3$ | H | Me | CH(Me)(4-$CF_3$OPh) | H |
| 1-210 | $CF_3$ | H | Me | CH(Me)(2,4-$F_2$Ph) | H |
| 1-211 | $CF_3$ | H | Me | CH(Et)Ph | H |
| 1-212 | $CF_3$ | H | Me | CH(n-Pr)Ph | H |
| 1-213 | $CF_3$ | H | Me | CH(i-Pr)Ph | H |
| 1-214 | $CF_3$ | H | Me | CH(n-Bu)Ph | H |
| 1-215 | $CF_3$ | H | Me | CH(n-Pen)Ph | H |
| 1-216 | $CF_3$ | H | Me | $CH_2CH_2$Ph | H |
| 1-217 | $CF_3$ | H | Me | $CH_2CH_2$(4-FPh) | H |
| 1-218 | $CF_3$ | H | Me | CH(Me)$CH_2$Ph | H |
| 1-219 | $CF_3$ | H | Me | $CH_2$CH(Me)Ph | H |
| 1-220 | $CF_3$ | H | Me | $CH_2CF_2$Ph | H |
| 1-221 | $CF_3$ | H | Me | $CH_2CH_2CH_2$Ph | H |
| 1-222 | $CF_3$ | H | Me | 1-indanyl | H |
| 1-223 | $CF_3$ | H | Me | 2-indanyl | H |
| 1-224 | $CF_3$ | H | Me | 1-(1,2,3,4-tetrahydro-Np) | H |
| 1-225 | $CF_3$ | H | Me | 2-(1,2,3,4-tetrahydro-Np) | H |
| 1-226 | $CF_3$ | H | Me | $CH_2$(2-oxiranyl) | H |
| 1-227 | $CF_3$ | H | Me | $CH_2$(3-oxetanyl) | H |
| 1-228 | $CF_3$ | H | Me | $CH_2$(2-Me-2-oxiranyl) | H |
| 1-229 | $CF_3$ | H | Me | $CH_2$(3-Me-3-oxetanyl) | H |
| 1-230 | $CF_3$ | H | Me | $CH_2$(2-tetrahydrofuryl) | H |
| 1-231 | $CF_3$ | H | Me | $CH_2$(2-thienyl) | H |
| 1-232 | $CF_3$ | H | Me | $CH_2$(3-thienyl) | H |
| 1-233 | $CF_3$ | H | Me | $CH_2$(2-pyridyl) | H |
| 1-234 | $CF_3$ | H | Me | CH(Me)(2-thienyl) | H |
| 1-235 | $CF_3$ | H | Me | CH(Me)(3-thienyl) | H |
| 1-236 | $CF_3$ | H | Me | CH(Me)(2-pyridyl) | H |
| 1-237 | $CF_3$ | H | Me | $CH_2CH_2$OPh | H |
| 1-238 | $CF_3$ | H | Me | $CH_2CH_2OCH_2$Ph | H |
| 1-239 | $CF_3$ | H | Me | $CH_2$COPh | H |
| 1-240 | $CF_3$ | H | Me | COMe | H |
| 1-241 | $CF_3$ | H | Me | COEt | H |
| 1-242 | $CF_3$ | H | Me | COi-Pr | H |
| 1-243 | $CF_3$ | H | Me | Bz | H |
| 1-244 | $CF_3$ | H | Me | $COCH_2$Ph | H |
| 1-245 | $CF_3$ | H | Me | $CO_2$Me | H |
| 1-246 | $CF_3$ | H | Me | $CO_2$Et | H |
| 1-247 | $CF_3$ | H | Me | CONHEt | H |
| 1-248 | $CF_3$ | H | Me | $CONEt_2$ | H |
| 1-249 | $CF_3$ | H | Me | $SO_2$Me | H |
| 1-250 | $CF_3$ | H | Me | $SO_2$Et | H |
| 1-251 | $CF_3$ | H | Me | $SO_2$i-Pr | H |
| 1-252 | $CF_3$ | H | Me | $SO_2CF_3$ | H |
| 1-253 | $CF_3$ | H | Me | $SO_2$Ph | H |
| 1-254 | $CF_3$ | H | Me | $SO_2$(4-MePh) | H |
| 1-255 | $CF_3$ | H | Me | $SO_2CH_2$Ph | H |
| 1-256 | $CF_3$ | Me | Me | Me | H |
| 1-257 | $CF_3$ | Me | Me | i-Pr | H |
| 1-258 | $CF_3$ | Me | Me | s-Bu | H |
| 1-259 | $CF_3$ | Me | Me | i-Bu | H |
| 1-260 | $CF_3$ | Me | Me | $CH_2$Ph | H |
| 1-261 | $CF_3$ | Et | Me | i-Pr | H |
| 1-262 | $CF_3$ | Et | Me | s-Bu | H |
| 1-263 | $CF_3$ | Et | Me | i-Bu | H |
| 1-264 | $CF_3$ | Et | Me | $CH_2$CH(Et)$CH_2CH_3$ | H |
| 1-265 | $CF_3$ | $CH_2CF_3$ | Me | s-Bu | H |
| 1-266 | $CF_3$ | $CH_2$CH=$CH_2$ | Me | s-Bu | H |
| 1-267 | $CF_3$ | $CH_2$C≡CH | Me | s-Bu | H |
| 1-268 | $CF_3$ | $CH_2$OMe | Me | i-Pr | H |
| 1-269 | $CF_3$ | $CH_2$OMe | Me | s-Bu | H |
| 1-270 | $CF_3$ | $CH_2$OMe | Me | i-Bu | H |
| 1-271 | $CF_3$ | $CH_2$OMe | Me | $CH_2$CH(Me)$CH_2CH_3$ | H |
| 1-272 | $CF_3$ | $CH_2OCH_2CF_3$ | Me | s-Bu | H |

TABLE 1-continued

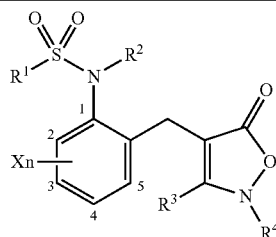

| No. | R¹ | R² | R³ | R⁴ | Xn |
|---|---|---|---|---|---|
| 1-273 | CF₃ | CH₂OCH₂CH₂OMe | Me | s-Bu | H |
| 1-274 | CF₃ | CH₂SMe | Me | s-Bu | H |
| 1-275 | CF₃ | CH₂COMe | Me | s-Bu | H |
| 1-276 | CF₃ | CH₂Ph | Me | i-Pr | H |
| 1-277 | CF₃ | CH₂Ph | Me | s-Bu | H |
| 1-278 | CF₃ | CH₂Ph | Me | i-Bu | H |
| 1-279 | CF₃ | CH₂Ph | Me | CH₂CH(Me)CH₂CH₃ | H |
| 1-280 | CF₃ | CH₂(4-ClPh) | Me | s-Bu | H |
| 1-281 | CF₃ | CH₂(4-MePh) | Me | s-Bu | H |
| 1-282 | CF₃ | CH₂(4-MeOPh) | Me | H | H |
| 1-283 | CF₃ | CH₂(4-MeOPh) | Me | i-Pr | H |
| 1-284 | CF₃ | CH₂(4-MeOPh) | Me | s-Bu | H |
| 1-285 | CF₃ | CH₂(4-MeOPh) | Me | i-Bu | H |
| 1-286 | CF₃ | CH₂(4-MeOPh) | Me | CH(Me)CH₂OMe | H |
| 1-287 | CF₃ | CH₂(4-MeOPh) | Me | CONEt₂ | H |
| 1-288 | CF₃ | CH₂CH₂OPh | Me | s-Bu | H |
| 1-289 | CF₃ | CH₂OCH₂Ph | Me | s-Bu | H |
| 1-290 | CF₃ | CH₂COPh | Me | s-Bu | H |
| 1-291 | CF₃ | COMe | Me | Me | H |
| 1-292 | CF₃ | COMe | Me | i-Pr | H |
| 1-293 | CF₃ | COMe | Me | t-Bu | H |
| 1-294 | CF₃ | COMe | Me | s-Bu | H |
| 1-295 | CF₃ | COMe | Me | CH(Et)CH₂CH₃ | H |
| 1-296 | CF₃ | COMe | Me | C(Me)₂CH₂CH₃ | H |
| 1-297 | CF₃ | COMe | Me | i-Bu | H |
| 1-298 | CF₃ | COMe | Me | CH₂C(Me)₂CH₃ | H |
| 1-299 | CF₃ | COMe | Me | CH(Me)CH₂CH₂CH₃ | H |
| 1-300 | CF₃ | COMe | Me | CH₂CH(Me)CH₂CH₃ | H |
| 1-301 | CF₃ | COMe | Me | CH₂CH(Et)CH₂CH₃ | H |
| 1-302 | CF₃ | COMe | Me | CH₂c-Pr | H |
| 1-303 | CF₃ | COMe | Me | CH₂CH₂OMe | H |
| 1-304 | CF₃ | COMe | Me | CH(Me)CH₂OMe | H |
| 1-305 | CF₃ | COMe | Me | CH₂CH₂SMe | H |
| 1-306 | CF₃ | COMe | Me | 2-ClPh | H |
| 1-307 | CF₃ | COMe | Me | 3-ClPh | H |
| 1-308 | CF₃ | COMe | Me | 4-ClPh | H |
| 1-309 | CF₃ | COMe | Me | CH₂Ph | H |
| 1-310 | CF₃ | COMe | Me | CH(Me)Ph | H |
| 1-311 | CF₃ | COMe | Me | CH(Me)(4-FPh) | H |
| 1-312 | CF₃ | COMe | Me | 1-indanyl | H |
| 1-313 | CF₃ | COMe | Me | 1-(1,2,3,4-tetrahydro-Np) | H |
| 1-314 | CF₃ | COEt | Me | i-Pr | H |
| 1-315 | CF₃ | COEt | Me | t-Bu | H |
| 1-316 | CF₃ | COEt | Me | s-Bu | H |
| 1-317 | CF₃ | COEt | Me | i-Bu | H |
| 1-318 | CF₃ | COEt | Me | CH₂C(Me)₂CH₃ | H |
| 1-319 | CF₃ | COEt | Me | CH(Me)CH₂OMe | H |
| 1-320 | CF₃ | COEt | Me | CH₂CH₂SMe | H |
| 1-321 | CF₃ | COEt | Me | CH(Me)Ph | H |
| 1-322 | CF₃ | COn-Pr | Me | i-Pr | H |
| 1-323 | CF₃ | COn-Pr | Me | t-Bu | H |
| 1-324 | CF₃ | COn-Pr | Me | s-Bu | H |
| 1-325 | CF₃ | COn-Pr | Me | i-Bu | H |
| 1-326 | CF₃ | COn-Pr | Me | CH(Me)CH₂OMe | H |
| 1-327 | CF₃ | COn-Pr | Me | CH(Me)Ph | H |
| 1-328 | CF₃ | COi-Pr | Me | i-Pr | H |
| 1-329 | CF₃ | COi-Pr | Me | t-Bu | H |
| 1-330 | CF₃ | COi-Pr | Me | s-Bu | H |
| 1-331 | CF₃ | COi-Pr | Me | CH(Et)CH₂CH₃ | H |
| 1-332 | CF₃ | COi-Pr | Me | i-Bu | H |
| 1-333 | CF₃ | COi-Pr | Me | CH₂C(Me)₂CH₃ | H |
| 1-334 | CF₃ | COi-Pr | Me | CH(Me)CH₂CH₂CH₃ | H |
| 1-335 | CF₃ | COi-Pr | Me | CH(Me)CH₂OMe | H |
| 1-336 | CF₃ | COi-Pr | Me | CH₂CH₂SMe | H |
| 1-337 | CF₃ | COi-Pr | Me | CH(Me)Ph | H |
| 1-338 | CF₃ | COn-Bu | Me | i-Pr | H |

TABLE 1-continued

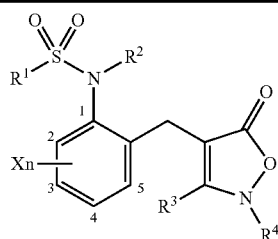

| No. | R$^1$ | R$^2$ | R$^3$ | R$^4$ | Xn |
|---|---|---|---|---|---|
| 1-339 | CF$_3$ | COn-Bu | Me | t-Bu | H |
| 1-340 | CF$_3$ | COn-Bu | Me | s-Bu | H |
| 1-341 | CF$_3$ | COn-Bu | Me | i-Bu | H |
| 1-342 | CF$_3$ | COn-Bu | Me | CH(Me)CH$_2$OMe | H |
| 1-343 | CF$_3$ | COn-Bu | Me | CH(Me)Ph | H |
| 1-344 | CF$_3$ | COs-Bu | Me | i-Pr | H |
| 1-345 | CF$_3$ | COs-Bu | Me | t-Bu | H |
| 1-346 | CF$_3$ | COs-Bu | Me | s-Bu | H |
| 1-347 | CF$_3$ | COs-Bu | Me | i-Bu | H |
| 1-348 | CF$_3$ | COs-Bu | Me | CH(Me)CH$_2$OMe | H |
| 1-349 | CF$_3$ | COs-Bu | Me | CH(Me)Ph | H |
| 1-350 | CF$_3$ | COi-Bu | Me | i-Pr | H |
| 1-351 | CF$_3$ | COi-Bu | Me | t-Bu | H |
| 1-352 | CF$_3$ | COi-Bu | Me | s-Bu | H |
| 1-353 | CF$_3$ | COi-Bu | Me | CH(Et)CH$_2$CH$_3$ | H |
| 1-354 | CF$_3$ | COi-Bu | Me | i-Bu | H |
| 1-355 | CF$_3$ | COi-Bu | Me | CH$_2$C(Me)$_2$CH$_3$ | H |
| 1-356 | CF$_3$ | COi-Bu | Me | CH(Me)CH$_2$CH$_3$ | H |
| 1-357 | CF$_3$ | COi-Bu | Me | CH(Me)CH$_2$OMe | H |
| 1-358 | CF$_3$ | COi-Bu | Me | CH$_2$CH$_2$SMe | H |
| 1-359 | CF$_3$ | COi-Bu | Me | CH(Me)Ph | H |
| 1-360 | CF$_3$ | COt-Bu | Me | i-Pr | H |
| 1-361 | CF$_3$ | COt-Bu | Me | t-Bu | H |
| 1-362 | CF$_3$ | COt-Bu | Me | s-Bu | H |
| 1-363 | CF$_3$ | COt-Bu | Me | i-Bu | H |
| 1-364 | CF$_3$ | COt-Bu | Me | CH(Me)CH$_2$OMe | H |
| 1-365 | CF$_3$ | COt-Bu | Me | CH(Me)Ph | H |
| 1-366 | CF$_3$ | COn-Pen | Me | i-Pr | H |
| 1-367 | CF$_3$ | COn-Pen | Me | t-Bu | H |
| 1-368 | CF$_3$ | COn-Pen | Me | s-Bu | H |
| 1-369 | CF$_3$ | COn-Pen | Me | i-Bu | H |
| 1-370 | CF$_3$ | COn-Pen | Me | CH(Me)CH$_2$OMe | H |
| 1-371 | CF$_3$ | COn-Pen | Me | CH(Me)Ph | H |
| 1-372 | CF$_3$ | COn-Hex | Me | i-Pr | H |
| 1-373 | CF$_3$ | COn-Hex | Me | t-Bu | H |
| 1-374 | CF$_3$ | COn-Hex | Me | s-Bu | H |
| 1-375 | CF$_3$ | COn-Hex | Me | i-Bu | H |
| 1-376 | CF$_3$ | COn-Hex | Me | CH(Me)CH$_2$OMe | H |
| 1-377 | CF$_3$ | COn-Hex | Me | CH(Me)Ph | H |
| 1-378 | CF$_3$ | COCF$_3$ | Me | i-Pr | H |
| 1-379 | CF$_3$ | COCF$_3$ | Me | t-Bu | H |
| 1-380 | CF$_3$ | COCF$_3$ | Me | s-Bu | H |
| 1-381 | CF$_3$ | COCF$_3$ | Me | i-Bu | H |
| 1-382 | CF$_3$ | COCF$_3$ | Me | CH(Me)CH$_2$OMe | H |
| 1-383 | CF$_3$ | COCF$_3$ | Me | CH(Me)Ph | H |
| 1-384 | CF$_3$ | COCH$_2$CF$_3$ | Me | i-Pr | H |
| 1-385 | CF$_3$ | COCH$_2$CF$_3$ | Me | t-Bu | H |
| 1-386 | CF$_3$ | COCH$_2$CF$_3$ | Me | s-Bu | H |
| 1-387 | CF$_3$ | COCH$_2$CF$_3$ | Me | i-Bu | H |
| 1-388 | CF$_3$ | COCH$_2$CF$_3$ | Me | CH(Me)CH$_2$OMe | H |
| 1-389 | CF$_3$ | COCH$_2$CF$_3$ | Me | CH(Me)Ph | H |
| 1-390 | CF$_3$ | COCH=CH$_2$ | Me | i-Pr | H |
| 1-391 | CF$_3$ | COCH=CH$_2$ | Me | t-Bu | H |
| 1-392 | CF$_3$ | COCH=CH$_2$ | Me | s-Bu | H |
| 1-393 | CF$_3$ | COCH=CH$_2$ | Me | i-Bu | H |
| 1-394 | CF$_3$ | COCH=CH$_2$ | Me | CH(Me)CH$_2$OMe | H |
| 1-395 | CF$_3$ | COCH=CH$_2$ | Me | CH(Me)Ph | H |
| 1-396 | CF$_3$ | COC≡CH | Me | i-Pr | H |
| 1-397 | CF$_3$ | COC≡CH | Me | t-Bu | H |
| 1-398 | CF$_3$ | COC≡CH | Me | s-Bu | H |
| 1-399 | CF$_3$ | COC≡CH | Me | i-Bu | H |
| 1-400 | CF$_3$ | COC≡CH | Me | CH(Me)CH$_2$OMe | H |
| 1-401 | CF$_3$ | COC≡CH | Me | CH(Me)Ph | H |
| 1-402 | CF$_3$ | COc-Pr | Me | i-Pr | H |
| 1-403 | CF$_3$ | COc-Pr | Me | t-Bu | H |
| 1-404 | CF$_3$ | COc-Pr | Me | s-Bu | H |

TABLE 1-continued

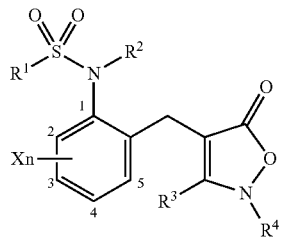

| No. | R¹ | R² | R³ | R⁴ | Xn |
|---|---|---|---|---|---|
| 1-405 | CF₃ | COc-Pr | Me | CH(Et)CH₂CH₃ | H |
| 1-406 | CF₃ | COc-Pr | Me | i-Bu | H |
| 1-407 | CF₃ | COc-Pr | Me | CH₂C(Me)₂CH₃ | H |
| 1-408 | CF₃ | COc-Pr | Me | CH(Me)CH₂CH₂CH₃ | H |
| 1-409 | CF₃ | COc-Pr | Me | CH₂CH(Me)CH₂CH₃ | H |
| 1-410 | CF₃ | COc-Pr | Me | CH₂CH(Et)CH₂CH₃ | H |
| 1-411 | CF₃ | COc-Pr | Me | CH₂c-Pr | H |
| 1-412 | CF₃ | COc-Pr | Me | CH(Me)CH₂OMe | H |
| 1-413 | CF₃ | COc-Pr | Me | CH₂CH₂SMe | H |
| 1-414 | CF₃ | COc-Pr | Me | 3-ClPh | H |
| 1-415 | CF₃ | COc-Pr | Me | CH₂Ph | H |
| 1-416 | CF₃ | COc-Pr | Me | CH(Me)Ph | H |
| 1-417 | CF₃ | COc-Pr | Me | CH(Me)(4-FPh) | H |
| 1-418 | CF₃ | COc-Bu | Me | i-Pr | H |
| 1-419 | CF₃ | COc-Bu | Me | t-Bu | H |
| 1-420 | CF₃ | COc-Bu | Me | s-Bu | H |
| 1-421 | CF₃ | COc-Bu | Me | i-Bu | H |
| 1-422 | CF₃ | COc-Bu | Me | CH(Me)CH₂OMe | H |
| 1-423 | CF₃ | COc-Bu | Me | CH(Me)Ph | H |
| 1-424 | CF₃ | COc-Pen | Me | i-Pr | H |
| 1-425 | CF₃ | COc-Pen | Me | t-Bu | H |
| 1-426 | CF₃ | COc-Pen | Me | s-Bu | H |
| 1-427 | CF₃ | COc-Pen | Me | i-Bu | H |
| 1-428 | CF₃ | COc-Pen | Me | CH(Me)CH₂OMe | H |
| 1-429 | CF₃ | COc-Pen | Me | CH(Me)Ph | H |
| 1-430 | CF₃ | COc-Hex | Me | i-Pr | H |
| 1-431 | CF₃ | COc-Hex | Me | t-Bu | H |
| 1-432 | CF₃ | COc-Hex | Me | s-Bu | H |
| 1-433 | CF₃ | COc-Hex | Me | i-Bu | H |
| 1-434 | CF₃ | COc-Hex | Me | CH(Me)CH₂OMe | H |
| 1-435 | CF₃ | COc-Hex | Me | CH(Me)Ph | H |
| 1-436 | CF₃ | COCH₂c-Pr | Me | i-Pr | H |
| 1-437 | CF₃ | COCH₂c-Pr | Me | t-Bu | H |
| 1-438 | CF₃ | COCH₂c-Pr | Me | s-Bu | H |
| 1-439 | CF₃ | COCH₂c-Pr | Me | i-Bu | H |
| 1-440 | CF₃ | COCH₂c-Pr | Me | CH(Me)CH₂OMe | H |
| 1-441 | CF₃ | COCH₂c-Pr | Me | CH(Me)Ph | H |
| 1-442 | CF₃ | COCH₂OMe | Me | i-Pr | H |
| 1-443 | CF₃ | COCH₂OMe | Me | t-Bu | H |
| 1-444 | CF₃ | COCH₂OMe | Me | s-Bu | H |
| 1-445 | CF₃ | COCH₂OMe | Me | i-Bu | H |
| 1-446 | CF₃ | COCH₂OMe | Me | CH(Me)CH₂OMe | H |
| 1-447 | CF₃ | COCH₂OMe | Me | CH(Me)Ph | H |
| 1-448 | CF₃ | COCH₂OCH₂CF₃ | Me | i-Pr | H |
| 1-449 | CF₃ | COCH₂OCH₂CF₃ | Me | t-Bu | H |
| 1-450 | CF₃ | COCH₂OCH₂CF₃ | Me | s-Bu | H |
| 1-451 | CF₃ | COCH₂OCH₂CF₃ | Me | i-Bu | H |
| 1-452 | CF₃ | COCH₂OCH₂CF₃ | Me | CH(Me)CH₂OMe | H |
| 1-453 | CF₃ | COCH₂OCH₂CF₃ | Me | CH(Me)Ph | H |
| 1-454 | CF₃ | COCH₂OCH₂CH₂OMe | Me | i-Pr | H |
| 1-455 | CF₃ | COCH₂OCH₂CH₂OMe | Me | t-Bu | H |
| 1-456 | CF₃ | COCH₂OCH₂CH₂OMe | Me | s-Bu | H |
| 1-457 | CF₃ | COCH₂OCH₂CH₂OMe | Me | i-Bu | H |
| 1-458 | CF₃ | COCH₂OCH₂CH₂OMe | Me | CH(Me)CH₂OMe | H |
| 1-459 | CF₃ | COCH₂OCH₂CH₂OMe | Me | CH(Me)Ph | H |
| 1-460 | CF₃ | COCH₂SMe | Me | i-Pr | H |
| 1-461 | CF₃ | COCH₂SMe | Me | t-Bu | H |
| 1-462 | CF₃ | COCH₂SMe | Me | s-Bu | H |
| 1-463 | CF₃ | COCH₂SMe | Me | i-Bu | H |
| 1-464 | CF₃ | COCH₂SMe | Me | CH(Me)CH₂OMe | H |
| 1-465 | CF₃ | COCH₂SMe | Me | CH(Me)Ph | H |
| 1-466 | CF₃ | COCH₂SCH₂CF₃ | Me | i-Pr | H |
| 1-467 | CF₃ | COCH₂SCH₂CF₃ | Me | t-Bu | H |
| 1-468 | CF₃ | COCH₂SCH₂CF₃ | Me | s-Bu | H |
| 1-469 | CF₃ | COCH₂SCH₂CF₃ | Me | i-Bu | H |
| 1-470 | CF₃ | COCH₂SCH₂CF₃ | Me | CH(Me)CH₂OMe | H |

TABLE 1-continued

| No. | R¹ | R² | R³ | R⁴ | Xn |
|---|---|---|---|---|---|
| 1-471 | CF₃ | COCH₂SCH₂CF₃ | Me | CH(Me)Ph | H |
| 1-472 | CF₃ | Bz | Me | i-Pr | H |
| 1-473 | CF₃ | Bz | Me | t-Bu | H |
| 1-474 | CF₃ | Bz | Me | s-Bu | H |
| 1-475 | CF₃ | Bz | Me | CH(Et)CH₂CH₃ | H |
| 1-476 | CF₃ | Bz | Me | i-Bu | H |
| 1-477 | CF₃ | Bz | Me | CH₂C(Me)₂CH₃ | H |
| 1-478 | CF₃ | Bz | Me | CH(Me)CH₂CH₂CH₃ | H |
| 1-479 | CF₃ | Bz | Me | CH(Me)CH₂OMe | H |
| 1-480 | CF₃ | Bz | Me | CH₂CH₂SMe | H |
| 1-481 | CF₃ | Bz | Me | CH(Me)Ph | H |
| 1-482 | CF₃ | 4-ClBz | Me | i-Pr | H |
| 1-483 | CF₃ | 4-ClBz | Me | t-Bu | H |
| 1-484 | CF₃ | 4-ClBz | Me | s-Bu | H |
| 1-485 | CF₃ | 4-ClBz | Me | CH(Et)CH₂CH₃ | H |
| 1-486 | CF₃ | 4-ClBz | Me | i-Bu | H |
| 1-487 | CF₃ | 4-ClBz | Me | CH₂C(Me)₂CH₃ | H |
| 1-488 | CF₃ | 4-ClBz | Me | CH(Me)CH₂CH₂CH₃ | H |
| 1-489 | CF₃ | 4-ClBz | Me | CH(Me)CH₂OMe | H |
| 1-490 | CF₃ | 4-ClBz | Me | CH₂CH₂SMe | H |
| 1-491 | CF₃ | 4-ClBz | Me | CH(Me)Ph | H |
| 1-492 | CF₃ | 4-MeBz | Me | i-Pr | H |
| 1-493 | CF₃ | 4-MeBz | Me | t-Bu | H |
| 1-494 | CF₃ | 4-MeBz | Me | s-Bu | H |
| 1-495 | CF₃ | 4-MeBz | Me | CH(Et)CH₂CH₃ | H |
| 1-496 | CF₃ | 4-MeBz | Me | i-Bu | H |
| 1-497 | CF₃ | 4-MeBz | Me | CH₂C(Me)₂CH₃ | H |
| 1-498 | CF₃ | 4-MeBz | Me | CH(Me)CH₂CH₂CH₃ | H |
| 1-499 | CF₃ | 4-MeBz | Me | CH(Me)CH₂OMe | H |
| 1-500 | CF₃ | 4-MeBz | Me | CH₂CH₂SMe | H |
| 1-501 | CF₃ | 4-MeBz | Me | CH(Me)Ph | H |
| 1-502 | CF₃ | COCH₂Ph | Me | i-Pr | H |
| 1-503 | CF₃ | COCH₂Ph | Me | t-Bu | H |
| 1-504 | CF₃ | COCH₂Ph | Me | s-Bu | H |
| 1-505 | CF₃ | COCH₂Ph | Me | i-Bu | H |
| 1-506 | CF₃ | COCH₂Ph | Me | CH(Me)CH₂OMe | H |
| 1-507 | CF₃ | COCH₂Ph | Me | CH(Me)Ph | H |
| 1-508 | CF₃ | COCH₂(4-ClPh) | Me | i-Pr | H |
| 1-509 | CF₃ | COCH₂(4-ClPh) | Me | t-Bu | H |
| 1-510 | CF₃ | COCH₂(4-ClPh) | Me | s-Bu | H |
| 1-511 | CF₃ | COCH₂(4-ClPh) | Me | i-Bu | H |
| 1-512 | CF₃ | COCH₂(4-ClPh) | Me | CH(Me)CH₂OMe | H |
| 1-513 | CF₃ | COCH₂(4-ClPh) | Me | CH(Me)Ph | H |
| 1-514 | CF₃ | COCH₂(4-MePh) | Me | i-Pr | H |
| 1-515 | CF₃ | COCH₂(4-MePh) | Me | t-Bu | H |
| 1-516 | CF₃ | COCH₂(4-MePh) | Me | s-Bu | H |
| 1-517 | CF₃ | COCH₂(4-MePh) | Me | i-Bu | H |
| 1-518 | CF₃ | COCH₂(4-MePh) | Me | CH(Me)CH₂OMe | H |
| 1-519 | CF₃ | COCH₂(4-MePh) | Me | CH(Me)Ph | H |
| 1-520 | CF₃ | CO(2-tetrahydrofuryl) | Me | i-Pr | H |
| 1-521 | CF₃ | CO(2-tetrahydrofuryl) | Me | t-Bu | H |
| 1-522 | CF₃ | CO(2-tetrahydrofuryl) | Me | s-Bu | H |
| 1-523 | CF₃ | CO(2-tetrahydrofuryl) | Me | i-Bu | H |
| 1-524 | CF₃ | CO(2-tetrahydrofuryl) | Me | CH(Me)CH₂OMe | H |
| 1-525 | CF₃ | CO(2-tetrahydrofuryl) | Me | CH(Me)Ph | H |
| 1-526 | CF₃ | CO(2-pyridyl) | Me | i-Pr | H |
| 1-527 | CF₃ | CO(2-pyridyl) | Me | t-Bu | H |
| 1-528 | CF₃ | CO(2-pyridyl) | Me | s-Bu | H |
| 1-529 | CF₃ | CO(2-pyridyl) | Me | i-Bu | H |
| 1-530 | CF₃ | CO(2-pyridyl) | Me | CH(Me)CH₂OMe | H |
| 1-531 | CF₃ | CO(2-pyridyl) | Me | CH(Me)Ph | H |
| 1-532 | CF₃ | CO(3-pyridyl) | Me | i-Pr | H |
| 1-533 | CF₃ | CO(3-pyridyl) | Me | t-Bu | H |
| 1-534 | CF₃ | CO(3-pyridyl) | Me | s-Bu | H |
| 1-535 | CF₃ | CO(3-pyridyl) | Me | i-Bu | H |
| 1-536 | CF₃ | CO(3-pyridyl) | Me | CH(Me)CH₂OMe | H |

TABLE 1-continued

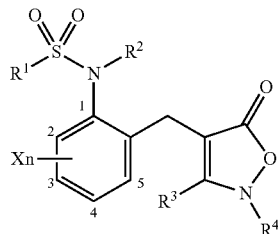

| No. | R¹ | R² | R³ | R⁴ | Xn |
|---|---|---|---|---|---|
| 1-537 | CF₃ | CO(3-pyridyl) | Me | CH(Me)Ph | H |
| 1-538 | CF₃ | CO(4-pyridyl) | Me | i-Pr | H |
| 1-539 | CF₃ | CO(4-pyridyl) | Me | t-Bu | H |
| 1-540 | CF₃ | CO(4-pyridyl) | Me | s-Bu | H |
| 1-541 | CF₃ | CO(4-pyridyl) | Me | i-Bu | H |
| 1-542 | CF₃ | CO(4-pyridyl) | Me | CH(Me)CH₂OMe | H |
| 1-543 | CF₃ | CO(4-pyridyl) | Me | CH(Me)Ph | H |
| 1-544 | CF₃ | CO(2-thienyl) | Me | i-Pr | H |
| 1-545 | CF₃ | CO(2-thienyl) | Me | t-Bu | H |
| 1-546 | CF₃ | CO(2-thienyl) | Me | s-Bu | H |
| 1-547 | CF₃ | CO(2-thienyl) | Me | i-Bu | H |
| 1-548 | CF₃ | CO(2-thienyl) | Me | CH(Me)CH₂OMe | H |
| 1-549 | CF₃ | CO(2-thienyl) | Me | CH(Me)Ph | H |
| 1-550 | CF₃ | CO(3-thienyl) | Me | i-Pr | H |
| 1-551 | CF₃ | CO(3-thienyl) | Me | t-Bu | H |
| 1-552 | CF₃ | CO(3-thienyl) | Me | s-Bu | H |
| 1-553 | CF₃ | CO(3-thienyl) | Me | i-Bu | H |
| 1-554 | CF₃ | CO(3-thienyl) | Me | CH(Me)CH₂OMe | H |
| 1-555 | CF₃ | CO(3-thienyl) | Me | CH(Me)Ph | H |
| 1-556 | CF₃ | CO(2-tetrahydrofurfuryl) | Me | i-Pr | H |
| 1-557 | CF₃ | CO(2-tetrahydrofurfuryl) | Me | t-Bu | H |
| 1-558 | CF₃ | CO(2-tetrahydrofurfuryl) | Me | s-Bu | H |
| 1-559 | CF₃ | CO(2-tetrahydrofurfuryl) | Me | i-Bu | H |
| 1-560 | CF₃ | CO(2-tetrahydrofurfuryl) | Me | CH(Me)CH₂OMe | H |
| 1-561 | CF₃ | CO(2-tetrahydrofurfuryl) | Me | CH(Me)Ph | H |
| 1-562 | CF₃ | COCH₂(2-pyridyl) | Me | i-Pr | H |
| 1-563 | CF₃ | COCH₂(2-pyridyl) | Me | t-Bu | H |
| 1-564 | CF₃ | COCH₂(2-pyridyl) | Me | s-Bu | H |
| 1-565 | CF₃ | COCH₂(2-pyridyl) | Me | i-Bu | H |
| 1-566 | CF₃ | COCH₂(2-pyridyl) | Me | CH(Me)CH₂OMe | H |
| 1-567 | CF₃ | COCH₂(2-pyridyl) | Me | CH(Me)Ph | H |
| 1-568 | CF₃ | COCH₂(2-thienyl) | Me | i-Pr | H |
| 1-569 | CF₃ | COCH₂(2-thienyl) | Me | t-Bu | H |
| 1-570 | CF₃ | COCH₂(2-thienyl) | Me | s-Bu | H |
| 1-571 | CF₃ | COCH₂(2-thienyl) | Me | i-Bu | H |
| 1-572 | CF₃ | COCH₂(2-thienyl) | Me | CH(Me)CH₂OMe | H |
| 1-573 | CF₃ | COCH₂(2-thienyl) | Me | CH(Me)Ph | H |
| 1-574 | CF₃ | CO₂Me | Me | Me | H |
| 1-575 | CF₃ | CO₂Me | Me | i-Pr | H |
| 1-576 | CF₃ | CO₂Me | Me | t-Bu | H |
| 1-577 | CF₃ | CO₂Me | Me | s-Bu | H |
| 1-578 | CF₃ | CO₂Me | Me | CH(Et)CH₂CH₃ | H |
| 1-579 | CF₃ | CO₂Me | Me | C(Me)₂CH₂CH₃ | H |
| 1-580 | CF₃ | CO₂Me | Me | i-Bu | H |
| 1-581 | CF₃ | CO₂Me | Me | CH₂C(Me)₂CH₃ | H |
| 1-582 | CF₃ | CO₂Me | Me | CH(Me)CH₂CH₂CH₃ | H |
| 1-583 | CF₃ | CO₂Me | Me | CH₂CH(Me)CH₂CH₃ | H |
| 1-584 | CF₃ | CO₂Me | Me | CH₂CH(Et)CH₂CH₃ | H |
| 1-585 | CF₃ | CO₂Me | Me | CH₂c-Pr | H |
| 1-586 | CF₃ | CO₂Me | Me | CH₂CH₂OMe | H |
| 1-587 | CF₃ | CO₂Me | Me | CH(Me)CH₂OMe | H |
| 1-588 | CF₃ | CO₂Me | Me | CH(Et)CH₂OMe | H |
| 1-589 | CF₃ | CO₂Me | Me | CH₂CH(Me)OMe | H |
| 1-590 | CF₃ | CO₂Me | Me | CH(Me)CH₂OEt | H |
| 1-591 | CF₃ | CO₂Me | Me | CH(Me)CH₂CH₂OMe | H |
| 1-592 | CF₃ | CO₂Me | Me | CH₂CH₂SMe | H |
| 1-593 | CF₃ | CO₂Me | Me | 2-ClPh | H |
| 1-594 | CF₃ | CO₂Me | Me | 3-ClPh | H |
| 1-595 | CF₃ | CO₂Me | Me | 4-ClPh | H |
| 1-596 | CF₃ | CO₂Me | Me | CH₂Ph | H |
| 1-597 | CF₃ | CO₂Me | Me | CH₂(4-FPh) | H |
| 1-598 | CF₃ | CO₂Me | Me | CH(Me)Ph | H |
| 1-599 | CF₃ | CO₂Me | Me | CH(Me)(4-FPh) | H |
| 1-600 | CF₃ | CO₂Me | Me | 1-indanyl | H |
| 1-601 | CF₃ | CO₂Me | Me | 1-(1,2,3,4-tetrahydro-Np) | H |
| 1-602 | CF₃ | CO₂Et | Me | Me | H |

TABLE 1-continued

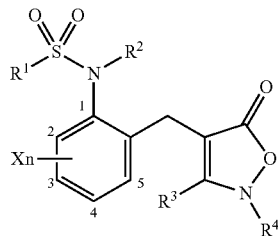

| No. | R¹ | R² | R³ | R⁴ | Xn |
|---|---|---|---|---|---|
| 1-603 | CF₃ | CO₂Et | Me | i-Pr | H |
| 1-604 | CF₃ | CO₂Et | Me | t-Bu | H |
| 1-605 | CF₃ | CO₂Et | Me | s-Bu | H |
| 1-606 | CF₃ | CO₂Et | Me | CH(Et)CH₂CH₃ | H |
| 1-607 | CF₃ | CO₂Et | Me | C(Me)₂CH₂CH₃ | H |
| 1-608 | CF₃ | CO₂Et | Me | i-Bu | H |
| 1-609 | CF₃ | CO₂Et | Me | CH₂C(Me)₂CH₃ | H |
| 1-610 | CF₃ | CO₂Et | Me | CH(Me)CH₂CH₂CH₃ | H |
| 1-611 | CF₃ | CO₂Et | Me | CH₂CH(Me)CH₂CH₃ | H |
| 1-612 | CF₃ | CO₂Et | Me | CH₂CH(Et)CH₂CH₃ | H |
| 1-613 | CF₃ | CO₂Et | Me | CH₂c-Pr | H |
| 1-614 | CF₃ | CO₂Et | Me | CH₂CH₂OMe | H |
| 1-615 | CF₃ | CO₂Et | Me | CH(Me)CH₂OMe | H |
| 1-616 | CF₃ | CO₂Et | Me | CH(Et)CH₂OMe | H |
| 1-617 | CF₃ | CO₂Et | Me | CH₂CH(Me)OMe | H |
| 1-618 | CF₃ | CO₂Et | Me | CH(Me)CH₂OEt | H |
| 1-619 | CF₃ | CO₂Et | Me | CH(Me)CH₂CH₂OMe | H |
| 1-620 | CF₃ | CO₂Et | Me | CH₂CH₂SMe | H |
| 1-621 | CF₃ | CO₂Et | Me | 2-ClPh | H |
| 1-622 | CF₃ | CO₂Et | Me | 3-ClPh | H |
| 1-623 | CF₃ | CO₂Et | Me | 4-ClPh | H |
| 1-624 | CF₃ | CO₂Et | Me | CH₂Ph | H |
| 1-625 | CF₃ | CO₂Et | Me | CH₂(4-FPh) | H |
| 1-626 | CF₃ | CO₂Et | Me | CH(Me)Ph | H |
| 1-627 | CF₃ | CO₂Et | Me | CH(Me)(4-FPh) | H |
| 1-628 | CF₃ | CO₂Et | Me | 1-indanyl | H |
| 1-629 | CF₃ | CO₂Et | Me | 1-(1,2,3,4-tetrahydro-Np) | H |
| 1-630 | CF₃ | CO₂n-Pr | Me | i-Pr | H |
| 1-631 | CF₃ | CO₂n-Pr | Me | t-Bu | H |
| 1-632 | CF₃ | CO₂n-Pr | Me | s-Bu | H |
| 1-633 | CF₃ | CO₂n-Pr | Me | i-Bu | H |
| 1-634 | CF₃ | CO₂n-Pr | Me | CH(Me)CH₂OMe | H |
| 1-635 | CF₃ | CO₂n-Pr | Me | CH(Et)CH₂OMe | H |
| 1-636 | CF₃ | CO₂n-Pr | Me | CH₂CH(Me)OMe | H |
| 1-637 | CF₃ | CO₂n-Pr | Me | CH(Me)CH₂OEt | H |
| 1-638 | CF₃ | CO₂n-Pr | Me | CH(Me)CH₂CH₂OMe | H |
| 1-639 | CF₃ | CO₂n-Pr | Me | CH(Me)Ph | H |
| 1-640 | CF₃ | CO₂i-Pr | Me | i-Pr | H |
| 1-641 | CF₃ | CO₂i-Pr | Me | t-Bu | H |
| 1-642 | CF₃ | CO₂i-Pr | Me | s-Bu | H |
| 1-643 | CF₃ | CO₂i-Pr | Me | CH(Et)CH₂CH₃ | H |
| 1-644 | CF₃ | CO₂i-Pr | Me | i-Bu | H |
| 1-645 | CF₃ | CO₂i-Pr | Me | CH₂C(Me)₂CH₃ | H |
| 1-646 | CF₃ | CO₂i-Pr | Me | CH(Me)CH₂CH₂CH₃ | H |
| 1-647 | CF₃ | CO₂i-Pr | Me | CH(Me)CH₂OMe | H |
| 1-648 | CF₃ | CO₂i-Pr | Me | CH(Et)CH₂OMe | H |
| 1-649 | CF₃ | CO₂i-Pr | Me | CH₂CH(Me)OMe | H |
| 1-650 | CF₃ | CO₂i-Pr | Me | CH(Me)CH₂OEt | H |
| 1-651 | CF₃ | CO₂i-Pr | Me | CH(Me)CH₂CH₂OMe | H |
| 1-652 | CF₃ | CO₂i-Pr | Me | CH₂CH₂SMe | H |
| 1-653 | CF₃ | CO₂i-Pr | Me | CH(Me)Ph | H |
| 1-654 | CF₃ | CO₂n-Bu | Me | i-Pr | H |
| 1-655 | CF₃ | CO₂n-Bu | Me | t-Bu | H |
| 1-656 | CF₃ | CO₂n-Bu | Me | s-Bu | H |
| 1-657 | CF₃ | CO₂n-Bu | Me | i-Bu | H |
| 1-658 | CF₃ | CO₂n-Bu | Me | CH(Me)CH₂OMe | H |
| 1-659 | CF₃ | CO₂n-Bu | Me | CH(Me)Ph | H |
| 1-660 | CF₃ | CO₂s-Bu | Me | i-Pr | H |
| 1-661 | CF₃ | CO₂s-Bu | Me | t-Bu | H |
| 1-662 | CF₃ | CO₂s-Bu | Me | s-Bu | H |
| 1-663 | CF₃ | CO₂s-Bu | Me | i-Bu | H |
| 1-664 | CF₃ | CO₂s-Bu | Me | CH(Me)CH₂OMe | H |
| 1-665 | CF₃ | CO₂s-Bu | Me | CH(Me)Ph | H |
| 1-666 | CF₃ | CO₂i-Bu | Me | Me | H |
| 1-667 | CF₃ | CO₂i-Bu | Me | i-Pr | H |
| 1-668 | CF₃ | CO₂i-Bu | Me | t-Bu | H |

TABLE 1-continued

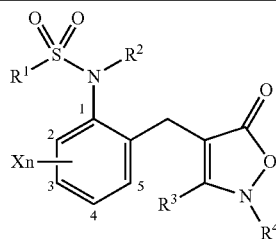

| No. | R¹ | R² | R³ | R⁴ | Xn |
|---|---|---|---|---|---|
| 1-669 | $CF_3$ | $CO_2$i-Bu | Me | s-Bu | H |
| 1-670 | $CF_3$ | $CO_2$i-Bu | Me | CH(Et)CH$_2$CH$_3$ | H |
| 1-671 | $CF_3$ | $CO_2$i-Bu | Me | i-Bu | H |
| 1-672 | $CF_3$ | $CO_2$i-Bu | Me | CH$_2$C(Me)$_2$CH$_3$ | H |
| 1-673 | $CF_3$ | $CO_2$i-Bu | Me | CH(Me)CH$_2$CH$_2$CH$_3$ | H |
| 1-674 | $CF_3$ | $CO_2$i-Bu | Me | CH$_2$CH(Me)CH$_2$CH$_3$ | H |
| 1-675 | $CF_3$ | $CO_2$i-Bu | Me | CH(Me)CH$_2$OMe | H |
| 1-676 | $CF_3$ | $CO_2$i-Bu | Me | CH$_2$CH$_2$SMe | H |
| 1-677 | $CF_3$ | $CO_2$i-Bu | Me | CH$_2$Ph | H |
| 1-678 | $CF_3$ | $CO_2$i-Bu | Me | CH(Me)Ph | H |
| 1-679 | $CF_3$ | $CO_2$i-Bu | Me | CONEt$_2$ | H |
| 1-680 | $CF_3$ | $CO_2$t-Bu | Me | i-Pr | H |
| 1-681 | $CF_3$ | $CO_2$t-Bu | Me | t-Bu | H |
| 1-682 | $CF_3$ | $CO_2$t-Bu | Me | s-Bu | H |
| 1-683 | $CF_3$ | $CO_2$t-Bu | Me | i-Bu | H |
| 1-684 | $CF_3$ | $CO_2$t-Bu | Me | CH(Me)CH$_2$OMe | H |
| 1-685 | $CF_3$ | $CO_2$t-Bu | Me | CH(Me)Ph | H |
| 1-686 | $CF_3$ | $CO_2$n-Pen | Me | i-Pr | H |
| 1-687 | $CF_3$ | $CO_2$n-Pen | Me | t-Bu | H |
| 1-688 | $CF_3$ | $CO_2$n-Pen | Me | s-Bu | H |
| 1-689 | $CF_3$ | $CO_2$n-Pen | Me | i-Bu | H |
| 1-690 | $CF_3$ | $CO_2$n-Pen | Me | CH(Me)CH$_2$OMe | H |
| 1-691 | $CF_3$ | $CO_2$n-Pen | Me | CH(Me)Ph | H |
| 1-692 | $CF_3$ | $CO_2$n-Hex | Me | i-Pr | H |
| 1-693 | $CF_3$ | $CO_2$n-Hex | Me | t-Bu | H |
| 1-694 | $CF_3$ | $CO_2$n-Hex | Me | s-Bu | H |
| 1-695 | $CF_3$ | $CO_2$n-Hex | Me | i-Bu | H |
| 1-696 | $CF_3$ | $CO_2$n-Hex | Me | CH(Me)CH$_2$OMe | H |
| 1-697 | $CF_3$ | $CO_2$n-Hex | Me | CH(Me)Ph | H |
| 1-698 | $CF_3$ | $CO_2CH_2CF_3$ | Me | i-Pr | H |
| 1-699 | $CF_3$ | $CO_2CH_2CF_3$ | Me | t-Bu | H |
| 1-700 | $CF_3$ | $CO_2CH_2CF_3$ | Me | s-Bu | H |
| 1-701 | $CF_3$ | $CO_2CH_2CF_3$ | Me | i-Bu | H |
| 1-702 | $CF_3$ | $CO_2CH_2CF_3$ | Me | CH(Me)CH$_2$OMe | H |
| 1-703 | $CF_3$ | $CO_2CH_2CF_3$ | Me | CH(Me)Ph | H |
| 1-704 | $CF_3$ | $CO_2CH_2CH=CH_2$ | Me | i-Pr | H |
| 1-705 | $CF_3$ | $CO_2CH_2CH=CH_2$ | Me | t-Bu | H |
| 1-706 | $CF_3$ | $CO_2CH_2CH=CH_2$ | Me | s-Bu | H |
| 1-707 | $CF_3$ | $CO_2CH_2CH=CH_2$ | Me | i-Bu | H |
| 1-708 | $CF_3$ | $CO_2CH_2CH=CH_2$ | Me | CH(Me)CH$_2$OMe | H |
| 1-709 | $CF_3$ | $CO_2CH_2CH=CH_2$ | Me | CH$_2$CH$_2$SMe | H |
| 1-710 | $CF_3$ | $CO_2CH_2CH=CH_2$ | Me | CH(Me)Ph | H |
| 1-711 | $CF_3$ | $CO_2CH_2C≡CH$ | Me | i-Pr | H |
| 1-712 | $CF_3$ | $CO_2CH_2C≡CH$ | Me | t-Bu | H |
| 1-713 | $CF_3$ | $CO_2CH_2C≡CH$ | Me | s-Bu | H |
| 1-714 | $CF_3$ | $CO_2CH_2C≡CH$ | Me | i-Bu | H |
| 1-715 | $CF_3$ | $CO_2CH_2C≡CH$ | Me | CH(Me)CH$_2$OMe | H |
| 1-716 | $CF_3$ | $CO_2CH_2C≡CH$ | Me | CH(Me)Ph | H |
| 1-717 | $CF_3$ | $CO_2$c-Pr | Me | i-Pr | H |
| 1-718 | $CF_3$ | $CO_2$c-Pr | Me | t-Bu | H |
| 1-719 | $CF_3$ | $CO_2$c-Pr | Me | s-Bu | H |
| 1-720 | $CF_3$ | $CO_2$c-Pr | Me | i-Bu | H |
| 1-721 | $CF_3$ | $CO_2$c-Pr | Me | CH(Me)CH$_2$OMe | H |
| 1-722 | $CF_3$ | $CO_2$c-Pr | Me | CH(Me)Ph | H |
| 1-723 | $CF_3$ | $CO_2CH_2$c-Pr | Me | i-Pr | H |
| 1-724 | $CF_3$ | $CO_2CH_2$c-Pr | Me | t-Bu | H |
| 1-725 | $CF_3$ | $CO_2CH_2$c-Pr | Me | s-Bu | H |
| 1-726 | $CF_3$ | $CO_2CH_2$c-Pr | Me | i-Bu | H |
| 1-727 | $CF_3$ | $CO_2CH_2$c-Pr | Me | CH(Me)CH$_2$OMe | H |
| 1-728 | $CF_3$ | $CO_2CH_2$c-Pr | Me | CH(Me)Ph | H |
| 1-729 | $CF_3$ | $CO_2CH_2CH_2OMe$ | Me | i-Pr | H |
| 1-730 | $CF_3$ | $CO_2CH_2CH_2OMe$ | Me | t-Bu | H |
| 1-731 | $CF_3$ | $CO_2CH_2CH_2OMe$ | Me | s-Bu | H |
| 1-732 | $CF_3$ | $CO_2CH_2CH_2OMe$ | Me | i-Bu | H |
| 1-733 | $CF_3$ | $CO_2CH_2CH_2OMe$ | Me | CH$_2$CH(Me)CH$_2$CH$_3$ | H |
| 1-734 | $CF_3$ | $CO_2CH_2CH_2OMe$ | Me | CH(Me)CH$_2$OMe | H |

TABLE 1-continued

| No. | R¹ | R² | R³ | R⁴ | Xn |
|---|---|---|---|---|---|
| 1-735 | $CF_3$ | $CO_2CH_2CH_2OMe$ | Me | $CH_2CH_2SMe$ | H |
| 1-736 | $CF_3$ | $CO_2CH_2CH_2OMe$ | Me | CH(Me)Ph | H |
| 1-737 | $CF_3$ | $CO_2CH_2CH_2OCH_2CF_3$ | Me | i-Pr | H |
| 1-738 | $CF_3$ | $CO_2CH_2CH_2OCH_2CF_3$ | Me | t-Bu | H |
| 1-739 | $CF_3$ | $CO_2CH_2CH_2OCH_2CF_3$ | Me | s-Bu | H |
| 1-740 | $CF_3$ | $CO_2CH_2CH_2OCH_2CF_3$ | Me | i-Bu | H |
| 1-741 | $CF_3$ | $CO_2CH_2CH_2OCH_2CF_3$ | Me | $CH(Me)CH_2OMe$ | H |
| 1-742 | $CF_3$ | $CO_2CH_2CH_2OCH_2CF_3$ | Me | CH(Me)Ph | H |
| 1-743 | $CF_3$ | $CO_2CH_2CH_2OCH_2CH_2OMe$ | Me | i-Pr | H |
| 1-744 | $CF_3$ | $CO_2CH_2CH_2OCH_2CH_2OMe$ | Me | t-Bu | H |
| 1-745 | $CF_3$ | $CO_2CH_2CH_2OCH_2CH_2OMe$ | Me | s-Bu | H |
| 1-746 | $CF_3$ | $CO_2CH_2CH_2OCH_2CH_2OMe$ | Me | i-Bu | H |
| 1-747 | $CF_3$ | $CO_2CH_2CH_2OCH_2CH_2OMe$ | Me | $CH(Me)CH_2OMe$ | H |
| 1-748 | $CF_3$ | $CO_2CH_2CH_2OCH_2CH_2OMe$ | Me | CH(Me)Ph | H |
| 1-749 | $CF_3$ | $CO_2CH_2CH_2SMe$ | Me | i-Pr | H |
| 1-750 | $CF_3$ | $CO_2CH_2CH_2SMe$ | Me | t-Bu | H |
| 1-751 | $CF_3$ | $CO_2CH_2CH_2SMe$ | Me | s-Bu | H |
| 1-752 | $CF_3$ | $CO_2CH_2CH_2SMe$ | Me | i-Bu | H |
| 1-753 | $CF_3$ | $CO_2CH_2CH_2SMe$ | Me | $CH(Me)CH_2OMe$ | H |
| 1-754 | $CF_3$ | $CO_2CH_2CH_2SMe$ | Me | CH(Me)Ph | H |
| 1-755 | $CF_3$ | $CO_2CH_2CH_2SCH_2CF_3$ | Me | i-Pr | H |
| 1-756 | $CF_3$ | $CO_2CH_2CH_2SCH_2CF_3$ | Me | t-Bu | H |
| 1-757 | $CF_3$ | $CO_2CH_2CH_2SCH_2CF_3$ | Me | s-Bu | H |
| 1-758 | $CF_3$ | $CO_2CH_2CH_2SCH_2CF_3$ | Me | i-Bu | H |
| 1-759 | $CF_3$ | $CO_2CH_2CH_2SCH_2CF_3$ | Me | $CH(Me)CH_2OMe$ | H |
| 1-760 | $CF_3$ | $CO_2CH_2CH_2SCH_2CF_3$ | Me | CH(Me)Ph | H |
| 1-761 | $CF_3$ | $CO_2Ph$ | Me | i-Pr | H |
| 1-762 | $CF_3$ | $CO_2Ph$ | Me | t-Bu | H |
| 1-763 | $CF_3$ | $CO_2Ph$ | Me | s-Bu | H |
| 1-764 | $CF_3$ | $CO_2Ph$ | Me | i-Bu | H |
| 1-765 | $CF_3$ | $CO_2Ph$ | Me | $CH(Me)CH_2OMe$ | H |
| 1-766 | $CF_3$ | $CO_2Ph$ | Me | CH(Me)Ph | H |
| 1-767 | $CF_3$ | $CO_2(4-ClPh)$ | Me | i-Pr | H |
| 1-768 | $CF_3$ | $CO_2(4-ClPh)$ | Me | t-Bu | H |
| 1-769 | $CF_3$ | $CO_2(4-ClPh)$ | Me | s-Bu | H |
| 1-770 | $CF_3$ | $CO_2(4-ClPh)$ | Me | i-Bu | H |
| 1-771 | $CF_3$ | $CO_2(4-ClPh)$ | Me | $CH(Me)CH_2OMe$ | H |
| 1-772 | $CF_3$ | $CO_2(4-ClPh)$ | Me | CH(Me)Ph | H |
| 1-773 | $CF_3$ | $CO_2(4-MePh)$ | Me | i-Pr | H |
| 1-774 | $CF_3$ | $CO_2(4-MePh)$ | Me | t-Bu | H |
| 1-775 | $CF_3$ | $CO_2(4-MePh)$ | Me | s-Bu | H |
| 1-776 | $CF_3$ | $CO_2(4-MePh)$ | Me | i-Bu | H |
| 1-777 | $CF_3$ | $CO_2(4-MePh)$ | Me | $CH(Me)CH_2OMe$ | H |
| 1-778 | $CF_3$ | $CO_2(4-MePh)$ | Me | CH(Me)Ph | H |
| 1-779 | $CF_3$ | $CO_2CH_2Ph$ | Me | Me | H |
| 1-780 | $CF_3$ | $CO_2CH_2Ph$ | Me | i-Pr | H |
| 1-781 | $CF_3$ | $CO_2CH_2Ph$ | Me | t-Bu | H |
| 1-782 (TLC top) | $CF_3$ | $CO_2CH_2Ph$ | Me | s-Bu | H |
| 1-783 (TLC bottom) | $CF_3$ | $CO_2CH_2Ph$ | Me | s-Bu | H |
| 1-784 | $CF_3$ | $CO_2CH_2Ph$ | Me | $CH(Et)CH_2CH_3$ | H |
| 1-785 | $CF_3$ | $CO_2CH_2Ph$ | Me | i-Bu | H |
| 1-786 | $CF_3$ | $CO_2CH_2Ph$ | Me | $CH_2C(Me)_2CH_3$ | H |
| 1-787 | $CF_3$ | $CO_2CH_2Ph$ | Me | $CH(Me)CH_2CH_2CH_3$ | H |
| 1-788 (TLC top) | $CF_3$ | $CO_2CH_2Ph$ | Me | $CH_2CH(Me)CH_2CH_3$ | H |
| 1-789 (TLC bottom) | $CF_3$ | $CO_2CH_2Ph$ | Me | $CH_2CH(Me)CH_2CH_3$ | H |
| 1-790 | $CF_3$ | $CO_2CH_2Ph$ | Me | $CH(Me)CH_2OMe$ | H |
| 1-791 | $CF_3$ | $CO_2CH_2Ph$ | Me | $CH_2CH_2SMe$ | H |
| 1-792 | $CF_3$ | $CO_2CH_2Ph$ | Me | 2-ClPh | H |
| 1-793 | $CF_3$ | $CO_2CH_2Ph$ | Me | 3-ClPh | H |
| 1-794 | $CF_3$ | $CO_2CH_2Ph$ | Me | 4-ClPh | H |
| 1-795 | $CF_3$ | $CO_2CH_2Ph$ | Me | $CH_2Ph$ | H |
| 1-796 | $CF_3$ | $CO_2CH_2Ph$ | Me | CH(Me)Ph | H |

TABLE 1-continued

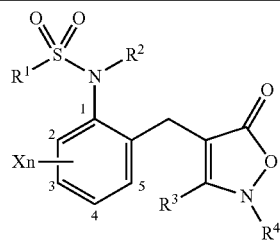

| No. | R¹ | R² | R³ | R⁴ | Xn |
|---|---|---|---|---|---|
| 1-797 | $CF_3$ | $CO_2CH_2$(4-ClPh) | Me | i-Pr | H |
| 1-798 | $CF_3$ | $CO_2CH_2$(4-ClPh) | Me | t-Bu | H |
| 1-799 | $CF_3$ | $CO_2CH_2$(4-ClPh) | Me | s-Bu | H |
| 1-800 | $CF_3$ | $CO_2CH_2$(4-ClPh) | Me | i-Bu | H |
| 1-801 | $CF_3$ | $CO_2CH_2$(4-ClPh) | Me | CH(Me)$CH_2$OMe | H |
| 1-802 | $CF_3$ | $CO_2CH_2$(4-ClPh) | Me | CH(Me)Ph | H |
| 1-803 | $CF_3$ | $CO_2CH_2$(4-MePh) | Me | i-Pr | H |
| 1-804 | $CF_3$ | $CO_2CH_2$(4-MePh) | Me | t-Bu | H |
| 1-805 | $CF_3$ | $CO_2CH_2$(4-MePh) | Me | s-Bu | H |
| 1-806 | $CF_3$ | $CO_2CH_2$(4-MePh) | Me | i-Bu | H |
| 1-807 | $CF_3$ | $CO_2CH_2$(4-MePh) | Me | CH(Me)$CH_2$OMe | H |
| 1-808 | $CF_3$ | $CO_2CH_2$(4-MePh) | Me | CH(Me)Ph | H |
| 1-809 | $CF_3$ | $CO_2$(2-tetrahydrofuryl) | Me | i-Pr | H |
| 1-810 | $CF_3$ | $CO_2$(2-tetrahydrofuryl) | Me | t-Bu | H |
| 1-811 | $CF_3$ | $CO_2$(2-tetrahydrofuryl) | Me | s-Bu | H |
| 1-812 | $CF_3$ | $CO_2$(2-tetrahydrofuryl) | Me | i-Bu | H |
| 1-813 | $CF_3$ | $CO_2$(2-tetrahydrofuryl) | Me | CH(Me)$CH_2$OMe | H |
| 1-814 | $CF_3$ | $CO_2$(2-tetrahydrofuryl) | Me | CH(Me)Ph | H |
| 1-815 | $CF_3$ | $CO_2$(2-pyridyl) | Me | i-Pr | H |
| 1-816 | $CF_3$ | $CO_2$(2-pyridyl) | Me | t-Bu | H |
| 1-817 | $CF_3$ | $CO_2$(2-pyridyl) | Me | s-Bu | H |
| 1-818 | $CF_3$ | $CO_2$(2-pyridyl) | Me | i-Bu | H |
| 1-819 | $CF_3$ | $CO_2$(2-pyridyl) | Me | CH(Me)$CH_2$OMe | H |
| 1-820 | $CF_3$ | $CO_2$(2-pyridyl) | Me | CH(Me)Ph | H |
| 1-821 | $CF_3$ | $CO_2$(2-thienyl) | Me | i-Pr | H |
| 1-822 | $CF_3$ | $CO_2$(2-thienyl) | Me | t-Bu | H |
| 1-823 | $CF_3$ | $CO_2$(2-thienyl) | Me | s-Bu | H |
| 1-824 | $CF_3$ | $CO_2$(2-thienyl) | Me | i-Bu | H |
| 1-825 | $CF_3$ | $CO_2$(2-thienyl) | Me | CH(Me)$CH_2$OMe | H |
| 1-826 | $CF_3$ | $CO_2$(2-thienyl) | Me | CH(Me)Ph | H |
| 1-827 | $CF_3$ | $CO_2$(2-tetrahydrofurfuryl) | Me | i-Pr | H |
| 1-828 | $CF_3$ | $CO_2$(2-tetrahydrofurfuryl) | Me | t-Bu | H |
| 1-829 | $CF_3$ | $CO_2$(2-tetrahydrofurfuryl) | Me | s-Bu | H |
| 1-830 | $CF_3$ | $CO_2$(2-tetrahydrofurfuryl) | Me | i-Bu | H |
| 1-831 | $CF_3$ | $CO_2$(2-tetrahydrofurfuryl) | Me | CH(Me)$CH_2$OMe | H |
| 1-832 | $CF_3$ | $CO_2$(2-tetrahydrofurfuryl) | Me | CH(Me)Ph | H |
| 1-833 | $CF_3$ | $CO_2CH_2$(2-pyridyl) | Me | i-Pr | H |
| 1-834 | $CF_3$ | $CO_2CH_2$(2-pyridyl) | Me | t-Bu | H |
| 1-835 | $CF_3$ | $CO_2CH_2$(2-pyridyl) | Me | s-Bu | H |
| 1-836 | $CF_3$ | $CO_2CH_2$(2-pyridyl) | Me | i-Bu | H |
| 1-837 | $CF_3$ | $CO_2CH_2$(2-pyridyl) | Me | CH(Me)$CH_2$OMe | H |
| 1-838 | $CF_3$ | $CO_2CH_2$(2-pyridyl) | Me | CH(Me)Ph | H |
| 1-839 | $CF_3$ | $CO_2CH_2$(2-thienyl) | Me | i-Pr | H |
| 1-840 | $CF_3$ | $CO_2CH_2$(2-thienyl) | Me | t-Bu | H |
| 1-841 | $CF_3$ | $CO_2CH_2$(2-thienyl) | Me | s-Bu | H |
| 1-842 | $CF_3$ | $CO_2CH_2$(2-thienyl) | Me | i-Bu | H |
| 1-843 | $CF_3$ | $CO_2CH_2$(2-thienyl) | Me | CH(Me)$CH_2$OMe | H |
| 1-844 | $CF_3$ | $CO_2CH_2$(2-thienyl) | Me | CH(Me)Ph | H |
| 1-845 | $CF_3$ | CO(SMe) | Me | i-Pr | H |
| 1-846 | $CF_3$ | CO(SMe) | Me | t-Bu | H |
| 1-847 | $CF_3$ | CO(SMe) | Me | s-Bu | H |
| 1-848 | $CF_3$ | CO(SMe) | Me | i-Bu | H |
| 1-849 | $CF_3$ | CO(SMe) | Me | CH(Me)$CH_2$OMe | H |
| 1-850 | $CF_3$ | CO(SMe) | Me | CH(Me)Ph | H |
| 1-851 | $CF_3$ | CO(SEt) | Me | i-Pr | H |
| 1-852 | $CF_3$ | CO(SEt) | Me | t-Bu | H |
| 1-853 | $CF_3$ | CO(SEt) | Me | s-Bu | H |
| 1-854 | $CF_3$ | CO(SEt) | Me | i-Bu | H |
| 1-855 | $CF_3$ | CO(SEt) | Me | CH(Me)$CH_2$OMe | H |
| 1-856 | $CF_3$ | CO(SEt) | Me | CH(Me)Ph | H |
| 1-857 | $CF_3$ | CO($SCF_3$) | Me | i-Pr | H |
| 1-858 | $CF_3$ | CO($SCF_3$) | Me | t-Bu | H |
| 1-859 | $CF_3$ | CO($SCF_3$) | Me | s-Bu | H |
| 1-860 | $CF_3$ | CO($SCF_3$) | Me | i-Bu | H |
| 1-861 | $CF_3$ | CO($SCF_3$) | Me | CH(Me)$CH_2$OMe | H |
| 1-862 | $CF_3$ | CO($SCF_3$) | Me | CH(Me)Ph | H |

TABLE 1-continued

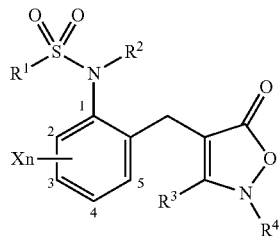

| No. | R¹ | R² | R³ | R⁴ | Xn |
|---|---|---|---|---|---|
| 1-863 | $CF_3$ | $CO(SCH_2CF_3)$ | Me | i-Pr | H |
| 1-864 | $CF_3$ | $CO(SCH_2CF_3)$ | Me | t-Bu | H |
| 1-865 | $CF_3$ | $CO(SCH_2CF_3)$ | Me | s-Bu | H |
| 1-866 | $CF_3$ | $CO(SCH_2CF_3)$ | Me | i-Bu | H |
| 1-867 | $CF_3$ | $CO(SCH_2CF_3)$ | Me | $CH(Me)CH_2OMe$ | H |
| 1-868 | $CF_3$ | $CO(SCH_2CF_3)$ | Me | CH(Me)Ph | H |
| 1-869 | $CF_3$ | CONHEt | Me | i-Pr | H |
| 1-870 | $CF_3$ | CONHEt | Me | t-Bu | H |
| 1-871 | $CF_3$ | CONHEt | Me | s-Bu | H |
| 1-872 | $CF_3$ | CONHEt | Me | i-Bu | H |
| 1-873 | $CF_3$ | CONHEt | Me | $CH(Me)CH_2OMe$ | H |
| 1-874 | $CF_3$ | CONHEt | Me | CH(Me)Ph | H |
| 1-875 | $CF_3$ | $CONHCH_2CF_3$ | Me | i-Pr | H |
| 1-876 | $CF_3$ | $CONHCH_2CF_3$ | Me | t-Bu | H |
| 1-877 | $CF_3$ | $CONHCH_2CF_3$ | Me | s-Bu | H |
| 1-878 | $CF_3$ | $CONHCH_2CF_3$ | Me | i-Bu | H |
| 1-879 | $CF_3$ | $CONHCH_2CF_3$ | Me | $CH(Me)CH_2OMe$ | H |
| 1-880 | $CF_3$ | $CONHCH_2CF_3$ | Me | CH(Me)Ph | H |
| 1-881 | $CF_3$ | $CONEt_2$ | Me | i-Pr | H |
| 1-882 | $CF_3$ | $CONEt_2$ | Me | t-Bu | H |
| 1-883 | $CF_3$ | $CONEt_2$ | Me | s-Bu | H |
| 1-884 | $CF_3$ | $CONEt_2$ | Me | i-Bu | H |
| 1-885 | $CF_3$ | $CONEt_2$ | Me | $CH(Me)CH_2OMe$ | H |
| 1-886 | $CF_3$ | $CONEt_2$ | Me | CH(Me)Ph | H |
| 1-887 | $CF_3$ | $SO_2Me$ | Me | Me | H |
| 1-888 | $CF_3$ | $SO_2Me$ | Me | i-Pr | H |
| 1-889 | $CF_3$ | $SO_2Me$ | Me | t-Bu | H |
| 1-890 | $CF_3$ | $SO_2Me$ | Me | s-Bu | H |
| 1-891 | $CF_3$ | $SO_2Me$ | Me | $CH(Et)CH_2CH_3$ | H |
| 1-892 | $CF_3$ | $SO_2Me$ | Me | i-Bu | H |
| 1-893 | $CF_3$ | $SO_2Me$ | Me | $CH_2C(Me)_2CH_3$ | H |
| 1-894 | $CF_3$ | $SO_2Me$ | Me | $CH(Me)CH_2CH_2CH_3$ | H |
| 1-895 | $CF_3$ | $SO_2Me$ | Me | $CH_2CH(Me)CH_2CH_3$ | H |
| 1-896 | $CF_3$ | $SO_2Me$ | Me | $CH_2CH(Et)CH_2CH_3$ | H |
| 1-897 | $CF_3$ | $SO_2Me$ | Me | $CH_2c-Pr$ | H |
| 1-898 | $CF_3$ | $SO_2Me$ | Me | $CH_2CH_2OMe$ | H |
| 1-899 | $CF_3$ | $SO_2Me$ | Me | $CH(Me)CH_2OMe$ | H |
| 1-900 | $CF_3$ | $SO_2Me$ | Me | $CH_2CH_2SMe$ | H |
| 1-901 | $CF_3$ | $SO_2Me$ | Me | Ph | H |
| 1-902 | $CF_3$ | $SO_2Me$ | Me | 2-ClPh | H |
| 1-903 | $CF_3$ | $SO_2Me$ | Me | 3-ClPh | H |
| 1-904 | $CF_3$ | $SO_2Me$ | Me | 4-ClPh | H |
| 1-905 | $CF_3$ | $SO_2Me$ | Me | $CH_2Ph$ | H |
| 1-906 | $CF_3$ | $SO_2Me$ | Me | $CH_2(4-FPh)$ | H |
| 1-907 | $CF_3$ | $SO_2Me$ | Me | CH(Me)Ph | H |
| 1-908 | $CF_3$ | $SO_2Me$ | Me | CH(Me)(4-FPh) | H |
| 1-909 | $CF_3$ | $SO_2Me$ | Me | 1-indanyl | H |
| 1-910 | $CF_3$ | $SO_2Me$ | Me | 1-(1,2,3,4-tetrahydro-Np) | H |
| 1-911 | $CF_3$ | $SO_2Et$ | Me | i-Pr | H |
| 1-912 | $CF_3$ | $SO_2Et$ | Me | t-Bu | H |
| 1-913 | $CF_3$ | $SO_2Et$ | Me | s-Bu | H |
| 1-914 | $CF_3$ | $SO_2Et$ | Me | i-Bu | H |
| 1-915 | $CF_3$ | $SO_2Et$ | Me | $CH(Me)CH_2OMe$ | H |
| 1-916 | $CF_3$ | $SO_2Et$ | Me | $CH_2CH_2SMe$ | H |
| 1-917 | $CF_3$ | $SO_2Et$ | Me | CH(Me)Ph | H |
| 1-918 | $CF_3$ | $SO_2n-Pr$ | Me | i-Pr | H |
| 1-919 | $CF_3$ | $SO_2n-Pr$ | Me | t-Bu | H |
| 1-920 | $CF_3$ | $SO_2n-Pr$ | Me | s-Bu | H |
| 1-921 | $CF_3$ | $SO_2n-Pr$ | Me | i-Bu | H |
| 1-922 | $CF_3$ | $SO_2n-Pr$ | Me | $CH(Me)CH_2OMe$ | H |
| 1-923 | $CF_3$ | $SO_2n-Pr$ | Me | CH(Me)Ph | H |
| 1-924 | $CF_3$ | $SO_2i-Pr$ | Me | i-Pr | H |
| 1-925 | $CF_3$ | $SO_2i-Pr$ | Me | t-Bu | H |
| 1-926 | $CF_3$ | $SO_2i-Pr$ | Me | s-Bu | H |
| 1-927 | $CF_3$ | $SO_2i-Pr$ | Me | i-Bu | H |
| 1-928 | $CF_3$ | $SO_2i-Pr$ | Me | $CH(Me)CH_2OMe$ | H |

TABLE 1-continued

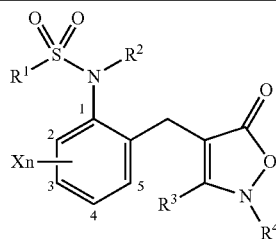

| No. | R¹ | R² | R³ | R⁴ | Xn |
|---|---|---|---|---|---|
| 1-929 | $CF_3$ | $SO_2$i-Pr | Me | CH(Me)Ph | H |
| 1-930 | $CF_3$ | $SO_2$n-Bu | Me | i-Pr | H |
| 1-931 | $CF_3$ | $SO_2$n-Bu | Me | t-Bu | H |
| 1-932 | $CF_3$ | $SO_2$n-Bu | Me | s-Bu | H |
| 1-933 | $CF_3$ | $SO_2$n-Bu | Me | i-Bu | H |
| 1-934 | $CF_3$ | $SO_2$n-Bu | Me | $CH(Me)CH_2OMe$ | H |
| 1-935 | $CF_3$ | $SO_2$n-Bu | Me | CH(Me)Ph | H |
| 1-936 | $CF_3$ | $SO_2$i-Bu | Me | i-Pr | H |
| 1-937 | $CF_3$ | $SO_2$i-Bu | Me | t-Bu | H |
| 1-938 | $CF_3$ | $SO_2$i-Bu | Me | s-Bu | H |
| 1-939 | $CF_3$ | $SO_2$i-Bu | Me | i-Bu | H |
| 1-940 | $CF_3$ | $SO_2$i-Bu | Me | $CH(Me)CH_2OMe$ | H |
| 1-941 | $CF_3$ | $SO_2$i-Bu | Me | CH(Me)Ph | H |
| 1-942 | $CF_3$ | $SO_2CH_2Cl$ | Me | i-Pr | H |
| 1-943 | $CF_3$ | $SO_2CH_2Cl$ | Me | t-Bu | H |
| 1-944 | $CF_3$ | $SO_2CH_2Cl$ | Me | i-Bu | H |
| 1-945 | $CF_3$ | $SO_2CH_2Cl$ | Me | $CH(Me)CH_2OMe$ | H |
| 1-946 | $CF_3$ | $SO_2CH_2Cl$ | Me | CH(Me)Ph | H |
| 1-947 | $CF_3$ | $SO_2CCl_3$ | Me | i-Pr | H |
| 1-948 | $CF_3$ | $SO_2CCl_3$ | Me | t-Bu | H |
| 1-949 | $CF_3$ | $SO_2CCl_3$ | Me | s-Bu | H |
| 1-950 | $CF_3$ | $SO_2CCl_3$ | Me | i-Bu | H |
| 1-951 | $CF_3$ | $SO_2CCl_3$ | Me | $CH(Me)CH_2OMe$ | H |
| 1-952 | $CF_3$ | $SO_2CCl_3$ | Me | CH(Me)Ph | H |
| 1-953 | $CF_3$ | $SO_2CHF_2$ | Me | i-Pr | H |
| 1-954 | $CF_3$ | $SO_2CHF_2$ | Me | t-Bu | H |
| 1-955 | $CF_3$ | $SO_2CHF_2$ | Me | i-Bu | H |
| 1-956 | $CF_3$ | $SO_2CHF_2$ | Me | $CH(Me)CH_2OMe$ | H |
| 1-957 | $CF_3$ | $SO_2CHF_2$ | Me | CH(Me)Ph | H |
| 1-958 | $CF_3$ | $SO_2CF_3$ | Me | H | H |
| 1-959 | $CF_3$ | $SO_2CF_3$ | Me | Me | H |
| 1-960 | $CF_3$ | $SO_2CF_3$ | Me | Et | H |
| 1-961 | $CF_3$ | $SO_2CF_3$ | Me | n-Pr | H |
| 1-962 | $CF_3$ | $SO_2CF_3$ | Me | i-Pr | H |
| 1-963 | $CF_3$ | $SO_2CF_3$ | Me | t-Bu | H |
| 1-964 | $CF_3$ | $SO_2CF_3$ | Me | s-Bu | H |
| 1-965 | $CF_3$ | $SO_2CF_3$ | Me | $CH(Et)CH_2CH_3$ | H |
| 1-966 | $CF_3$ | $SO_2CF_3$ | Me | $C(Me)_2CH_2CH_3$ | H |
| 1-967 | $CF_3$ | $SO_2CF_3$ | Me | i-Bu | H |
| 1-968 | $CF_3$ | $SO_2CF_3$ | Me | $CH_2C(Me)_2CH_3$ | H |
| 1-969 | $CF_3$ | $SO_2CF_3$ | Me | n-Bu | H |
| 1-970 | $CF_3$ | $SO_2CF_3$ | Me | $CH(Me)CH_2CH_2CH_3$ | H |
| 1-971 | $CF_3$ | $SO_2CF_3$ | Me | $CH(Et)CH_2CH_2CH_3$ | H |
| 1-972 | $CF_3$ | $SO_2CF_3$ | Me | $CH_2CH(Me)CH_2CH_3$ | H |
| 1-973 | $CF_3$ | $SO_2CF_3$ | Me | $CH_2CH(Et)CH_2CH_3$ | H |
| 1-974 | $CF_3$ | $SO_2CF_3$ | Me | $CH_2CH_2CH(Me)CH_3$ | H |
| 1-975 | $CF_3$ | $SO_2CF_3$ | Me | $CH_2CH_2C(Me)_2CH_3$ | H |
| 1-976 | $CF_3$ | $SO_2CF_3$ | Me | n-Pen | H |
| 1-977 | $CF_3$ | $SO_2CF_3$ | Me | $CH(Me)CH_2CH_2CH_2CH_3$ | H |
| 1-978 | $CF_3$ | $SO_2CF_3$ | Me | $CH_2CH_2CH(Me)CH_2CH_3$ | H |
| 1-979 | $CF_3$ | $SO_2CF_3$ | Me | n-Hex | H |
| 1-980 | $CF_3$ | $SO_2CF_3$ | Me | $CH_2CH(Et)CH_2CH_2CH_2CH_3$ | H |
| 1-981 | $CF_3$ | $SO_2CF_3$ | Me | $(CH_2)_7CH_3$ | H |
| 1-982 | $CF_3$ | $SO_2CF_3$ | Me | $(CH_2)_{13}CH_3$ | H |
| 1-983 | $CF_3$ | $SO_2CF_3$ | Me | $CH_2CH_2Cl$ | H |
| 1-984 | $CF_3$ | $SO_2CF_3$ | Me | $CH_2CF_3$ | H |
| 1-985 | $CF_3$ | $SO_2CF_3$ | Me | $CH_2CH{=}CH_2$ | H |
| 1-986 | $CF_3$ | $SO_2CF_3$ | Me | $CH(Me)CH{=}CH_2$ | H |
| 1-987 | $CF_3$ | $SO_2CF_3$ | Me | $CH_2C(Me){=}CH_2$ | H |
| 1-988 | $CF_3$ | $SO_2CF_3$ | Me | $CH_2C{\equiv}CH$ | H |
| 1-989 | $CF_3$ | $SO_2CF_3$ | Me | c-Pr | H |
| 1-990 | $CF_3$ | $SO_2CF_3$ | Me | c-Hex | H |
| 1-991 | $CF_3$ | $SO_2CF_3$ | Me | $CH_2$c-Pr | H |
| 1-992 | $CF_3$ | $SO_2CF_3$ | Me | CH(Me)c-Pr | H |
| 1-993 | $CF_3$ | $SO_2CF_3$ | Me | $CH_2$(1-Me-c-Pr) | H |
| 1-994 | $CF_3$ | $SO_2CF_3$ | Me | $CH_2$c-Hex | H |

TABLE 1-continued

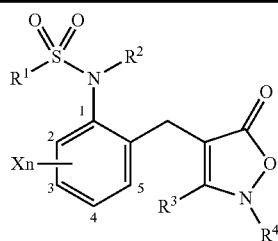

| No. | R¹ | R² | R³ | R⁴ | Xn |
|---|---|---|---|---|---|
| 1-995 | CF₃ | SO₂CF₃ | Me | CH₂OMe | H |
| 1-996 | CF₃ | SO₂CF₃ | Me | CH₂CH₂OMe | H |
| 1-997 | CF₃ | SO₂CF₃ | Me | CH(Me)CH₂OMe | H |
| 1-998 | CF₃ | SO₂CF₃ | Me | CH₂CH(Me)OMe | H |
| 1-999 | CF₃ | SO₂CF₃ | Me | CH₂CH₂Oi-Pr | H |
| 1-1000 | CF₃ | SO₂CF₃ | Me | CH₂CH₂Oi-Bu | H |
| 1-1001 | CF₃ | SO₂CF₃ | Me | CH₂CH₂CH₂OMe | H |
| 1-1002 | CF₃ | SO₂CF₃ | Me | CH₂CH₂SMe | H |
| 1-1003 | CF₃ | SO₂CF₃ | Me | CH₂CH₂CH₂SMe | H |
| 1-1004 | CF₃ | SO₂CF₃ | Me | CH₂CH₂SCH₂CF₃ | H |
| 1-1005 | CF₃ | SO₂CF₃ | Me | CH₂CH₂SOMe | H |
| 1-1006 | CF₃ | SO₂CF₃ | Me | CH₂CH₂SO₂Me | H |
| 1-1007 | CF₃ | SO₂CF₃ | Me | Ph | H |
| 1-1008 | CF₃ | SO₂CF₃ | Me | 2-ClPh | H |
| 1-1009 | CF₃ | SO₂CF₃ | Me | 3-ClPh | H |
| 1-1010 | CF₃ | SO₂CF₃ | Me | 4-ClPh | H |
| 1-1011 | CF₃ | SO₂CF₃ | Me | CH₂Ph | H |
| 1-1012 | CF₃ | SO₂CF₃ | Me | CH₂(2-FPh) | H |
| 1-1013 | CF₃ | SO₂CF₃ | Me | CH₂(3-FPh) | H |
| 1-1014 | CF₃ | SO₂CF₃ | Me | CH₂(4-FPh) | H |
| 1-1015 | CF₃ | SO₂CF₃ | Me | CH₂(4-ClPh) | H |
| 1-1016 | CF₃ | SO₂CF₃ | Me | CH₂(4-BrPh) | H |
| 1-1017 | CF₃ | SO₂CF₃ | Me | CH₂(4-CNPh) | H |
| 1-1018 | CF₃ | SO₂CF₃ | Me | CH₂(4-MePh) | H |
| 1-1019 | CF₃ | SO₂CF₃ | Me | CH₂(4-t-BuPh) | H |
| 1-1020 | CF₃ | SO₂CF₃ | Me | CH₂(3-CF₃Ph) | H |
| 1-1021 | CF₃ | SO₂CF₃ | Me | CH₂(4-CF₃Ph) | H |
| 1-1022 | CF₃ | SO₂CF₃ | Me | CH₂(4-MeOPh) | H |
| 1-1023 | CF₃ | SO₂CF₃ | Me | CH₂(4-CF₃OPh) | H |
| 1-1024 | CF₃ | SO₂CF₃ | Me | CH₂(4-MeSPh) | H |
| 1-1025 | CF₃ | SO₂CF₃ | Me | CH₂(4-CF₃SPh) | H |
| 1-1026 | CF₃ | SO₂CF₃ | Me | CH₂(2,4-F₂Ph) | H |
| 1-1027 | CF₃ | SO₂CF₃ | Me | CH₂(3,4-F₂Ph) | H |
| 1-1028 | CF₃ | SO₂CF₃ | Me | CH₂(2-Cl-4-FPh) | H |
| 1-1029 | CF₃ | SO₂CF₃ | Me | CH₂(3-Cl-4-FPh) | H |
| 1-1030 | CF₃ | SO₂CF₃ | Me | CH(Me)Ph | H |
| 1-1031 | CF₃ | SO₂CF₃ | Me | CH(Me)(4-FPh) | H |
| 1-1032 | CF₃ | SO₂CF₃ | Me | CH(Me)(2-ClPh) | H |
| 1-1033 | CF₃ | SO₂CF₃ | Me | CH(Me)(3-ClPh) | H |
| 1-1034 | CF₃ | SO₂CF₃ | Me | CH(Me)(4-ClPh) | H |
| 1-1035 | CF₃ | SO₂CF₃ | Me | CH(Me)(4-MePh) | H |
| 1-1036 | CF₃ | SO₂CF₃ | Me | CH(Me)(4-CF₃OPh) | H |
| 1-1037 | CF₃ | SO₂CF₃ | Me | CH(Me)(2,4-F₂Ph) | H |
| 1-1038 | CF₃ | SO₂CF₃ | Me | CH(Et)Ph | H |
| 1-1039 | CF₃ | SO₂CF₃ | Me | CH(n-Pr)Ph | H |
| 1-1040 | CF₃ | SO₂CF₃ | Me | CH(i-Pr)Ph | H |
| 1-1041 | CF₃ | SO₂CF₃ | Me | CH(n-Bu)Ph | H |
| 1-1042 | CF₃ | SO₂CF₃ | Me | CH(n-Pen)Ph | H |
| 1-1043 | CF₃ | SO₂CF₃ | Me | CH₂CH₂Ph | H |
| 1-1044 | CF₃ | SO₂CF₃ | Me | CH₂CH₂(4-FPh) | H |
| 1-1045 | CF₃ | SO₂CF₃ | Me | CH(Me)CH₂Ph | H |
| 1-1046 | CF₃ | SO₂CF₃ | Me | CH₂CH(Me)Ph | H |
| 1-1047 | CF₃ | SO₂CF₃ | Me | CH₂CF₂Ph | H |
| 1-1048 | CF₃ | SO₂CF₃ | Me | CH₂CH₂CH₂Ph | H |
| 1-1049 | CF₃ | SO₂CF₃ | Me | 1-indanyl | H |
| 1-1050 | CF₃ | SO₂CF₃ | Me | 1-(1,2,3,4-tetrahydro-Np) | H |
| 1-1051 | CF₃ | SO₂CF₃ | Me | CH₂(2-Me-2-oxiranyl) | H |
| 1-1052 | CF₃ | SO₂CF₃ | Me | CH₂(3-Me-3-oxetanyl) | H |
| 1-1053 | CF₃ | SO₂CF₃ | Me | CH₂(2-tetrahydrofuryl) | H |
| 1-1054 | CF₃ | SO₂CF₃ | Me | CH₂(2-thienyl) | H |
| 1-1055 | CF₃ | SO₂CF₃ | Me | CH₂(3-thienyl) | H |
| 1-1056 | CF₃ | SO₂CF₃ | Me | CH(Me)(2-thienyl) | H |
| 1-1057 | CF₃ | SO₂CF₃ | Me | CH(Me)(3-thienyl) | H |
| 1-1058 | CF₃ | SO₂CF₃ | Me | CH₂CH₂OPh | H |
| 1-1059 | CF₃ | SO₂CF₃ | Me | CH₂CH₂OCH₂Ph | H |
| 1-1060 | CF₃ | SO₂CF₃ | Me | COMe | H |

TABLE 1-continued

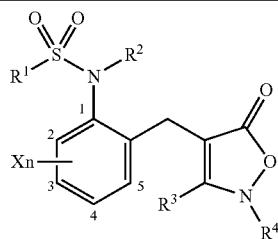

| No. | R¹ | R² | R³ | R⁴ | Xn |
|---|---|---|---|---|---|
| 1-1061 | CF₃ | SO₂CF₃ | Me | COi-Pr | H |
| 1-1062 | CF₃ | SO₂CF₃ | Me | Bz | H |
| 1-1063 | CF₃ | SO₂CF₃ | Me | SO₂Me | H |
| 1-1064 | CF₃ | SO₂CF₃ | Me | SO₂i-Pr | H |
| 1-1065 | CF₃ | SO₂CF₃ | Me | SO₂CF₃ | H |
| 1-1066 | CF₃ | SO₂CF₃ | Me | SO₂(4-MePh) | H |
| 1-1067 | CF₃ | SO₂CH₂CF₃ | Me | i-Pr | H |
| 1-1068 | CF₃ | SO₂CH₂CF₃ | Me | t-Bu | H |
| 1-1069 | CF₃ | SO₂CH₂CF₃ | Me | s-Bu | H |
| 1-1070 | CF₃ | SO₂CH₂CF₃ | Me | i-Bu | H |
| 1-1071 | CF₃ | SO₂CH₂CF₃ | Me | CH(Me)CH₂OMe | H |
| 1-1072 | CF₃ | SO₂CH₂CF₃ | Me | CH(Me)Ph | H |
| 1-1073 | CF₃ | SO₂CH=CH₂ | Me | i-Pr | H |
| 1-1074 | CF₃ | SO₂CH=CH₂ | Me | t-Bu | H |
| 1-1075 | CF₃ | SO₂CH=CH₂ | Me | s-Bu | H |
| 1-1076 | CF₃ | SO₂CH=CH₂ | Me | i-Bu | H |
| 1-1077 | CF₃ | SO₂CH=CH₂ | Me | CH(Me)CH₂OMe | H |
| 1-1078 | CF₃ | SO₂CH=CH₂ | Me | CH(Me)Ph | H |
| 1-1079 | CF₃ | SO₂CH₂CH=CH₂ | Me | i-Pr | H |
| 1-1080 | CF₃ | SO₂CH₂CH=CH₂ | Me | t-Bu | H |
| 1-1081 | CF₃ | SO₂CH₂CH=CH₂ | Me | s-Bu | H |
| 1-1082 | CF₃ | SO₂CH₂CH=CH₂ | Me | i-Bu | H |
| 1-1083 | CF₃ | SO₂CH₂CH=CH₂ | Me | CH(Me)CH₂OMe | H |
| 1-1084 | CF₃ | SO₂CH₂CH=CH₂ | Me | CH(Me)Ph | H |
| 1-1085 | CF₃ | SO₂CH₂C≡CH | Me | i-Pr | H |
| 1-1086 | CF₃ | SO₂CH₂C≡CH | Me | t-Bu | H |
| 1-1087 | CF₃ | SO₂CH₂C≡CH | Me | s-Bu | H |
| 1-1088 | CF₃ | SO₂CH₂C≡CH | Me | i-Bu | H |
| 1-1089 | CF₃ | SO₂CH₂C≡CH | Me | CH(Me)CH₂OMe | H |
| 1-1090 | CF₃ | SO₂CH₂C≡CH | Me | CH(Me)Ph | H |
| 1-1091 | CF₃ | SO₂c-Pr | Me | i-Pr | H |
| 1-1092 | CF₃ | SO₂c-Pr | Me | t-Bu | H |
| 1-1093 | CF₃ | SO₂c-Pr | Me | s-Bu | H |
| 1-1094 | CF₃ | SO₂c-Pr | Me | i-Bu | H |
| 1-1095 | CF₃ | SO₂c-Pr | Me | CH(Me)CH₂OMe | H |
| 1-1096 | CF₃ | SO₂c-Pr | Me | CH(Me)Ph | H |
| 1-1097 | CF₃ | SO₂c-Hex | Me | i-Pr | H |
| 1-1098 | CF₃ | SO₂c-Hex | Me | t-Bu | H |
| 1-1099 | CF₃ | SO₂c-Hex | Me | s-Bu | H |
| 1-1100 | CF₃ | SO₂c-Hex | Me | i-Bu | H |
| 1-1101 | CF₃ | SO₂c-Hex | Me | CH(Me)CH₂OMe | H |
| 1-1102 | CF₃ | SO₂c-Hex | Me | CH(Me)Ph | H |
| 1-1103 | CF₃ | SO₂CH₂c-Pr | Me | i-Pr | H |
| 1-1104 | CF₃ | SO₂CH₂c-Pr | Me | t-Bu | H |
| 1-1105 | CF₃ | SO₂CH₂c-Pr | Me | s-Bu | H |
| 1-1106 | CF₃ | SO₂CH₂c-Pr | Me | i-Bu | H |
| 1-1107 | CF₃ | SO₂CH₂c-Pr | Me | CH(Me)CH₂OMe | H |
| 1-1108 | CF₃ | SO₂CH₂c-Pr | Me | CH(Me)Ph | H |
| 1-1109 | CF₃ | SO₂CH₂CH₂OMe | Me | i-Pr | H |
| 1-1110 | CF₃ | SO₂CH₂CH₂OMe | Me | t-Bu | H |
| 1-1111 | CF₃ | SO₂CH₂CH₂OMe | Me | s-Bu | H |
| 1-1112 | CF₃ | SO₂CH₂CH₂OMe | Me | i-Bu | H |
| 1-1113 | CF₃ | SO₂CH₂CH₂OMe | Me | CH(Me)CH₂OMe | H |
| 1-1114 | CF₃ | SO₂CH₂CH₂OMe | Me | CH(Me)Ph | H |
| 1-1115 | CF₃ | SO₂Ph | Me | i-Pr | H |
| 1-1116 | CF₃ | SO₂Ph | Me | t-Bu | H |
| 1-1117 | CF₃ | SO₂Ph | Me | s-Bu | H |
| 1-1118 | CF₃ | SO₂Ph | Me | i-Bu | H |
| 1-1119 | CF₃ | SO₂Ph | Me | CH(Me)CH₂OMe | H |
| 1-1120 | CF₃ | SO₂Ph | Me | CH(Me)Ph | H |
| 1-1121 | CF₃ | SO₂(4-ClPh) | Me | i-Pr | H |
| 1-1122 | CF₃ | SO₂(4-ClPh) | Me | t-Bu | H |
| 1-1123 | CF₃ | SO₂(4-ClPh) | Me | s-Bu | H |
| 1-1124 | CF₃ | SO₂(4-ClPh) | Me | i-Bu | H |
| 1-1125 | CF₃ | SO₂(4-ClPh) | Me | CH(Me)CH₂OMe | H |
| 1-1126 | CF₃ | SO₂(4-ClPh) | Me | CH(Me)Ph | H |

TABLE 1-continued

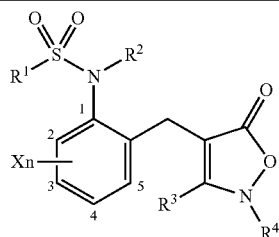

| No. | R¹ | R² | R³ | R⁴ | Xn |
|---|---|---|---|---|---|
| 1-1127 | CF₃ | SO₂(4-MePh) | Me | i-Pr | H |
| 1-1128 | CF₃ | SO₂(4-MePh) | Me | t-Bu | H |
| 1-1129 | CF₃ | SO₂(4-MePh) | Me | s-Bu | H |
| 1-1130 | CF₃ | SO₂(4-MePh) | Me | i-Bu | H |
| 1-1131 | CF₃ | SO₂(4-MePh) | Me | CH(Me)CH₂OMe | H |
| 1-1132 | CF₃ | SO₂(4-MePh) | Me | CH(Me)Ph | H |
| 1-1133 | CF₃ | SO₂CH₂Ph | Me | i-Pr | H |
| 1-1134 | CF₃ | SO₂CH₂Ph | Me | t-Bu | H |
| 1-1135 | CF₃ | SO₂CH₂Ph | Me | s-Bu | H |
| 1-1136 | CF₃ | SO₂CH₂Ph | Me | i-Bu | H |
| 1-1137 | CF₃ | SO₂CH₂Ph | Me | CH(Me)CH₂OMe | H |
| 1-1138 | CF₃ | SO₂CH₂Ph | Me | CH(Me)Ph | H |
| 1-1139 | CF₃ | SO₂CH₂(4-ClPh) | Me | i-Pr | H |
| 1-1140 | CF₃ | SO₂CH₂(4-ClPh) | Me | t-Bu | H |
| 1-1141 | CF₃ | SO₂CH₂(4-ClPh) | Me | s-Bu | H |
| 1-1142 | CF₃ | SO₂CH₂(4-ClPh) | Me | i-Bu | H |
| 1-1143 | CF₃ | SO₂CH₂(4-ClPh) | Me | CH(Me)CH₂OMe | H |
| 1-1144 | CF₃ | SO₂CH₂(4-ClPh) | Me | CH(Me)Ph | H |
| 1-1145 | CF₃ | SO₂CH₂(4-MePh) | Me | i-Pr | H |
| 1-1146 | CF₃ | SO₂CH₂(4-MePh) | Me | t-Bu | H |
| 1-1147 | CF₃ | SO₂CH₂(4-MePh) | Me | s-Bu | H |
| 1-1148 | CF₃ | SO₂CH₂(4-MePh) | Me | i-Bu | H |
| 1-1149 | CF₃ | SO₂CH₂(4-MePh) | Me | CH(Me)CH₂OMe | H |
| 1-1150 | CF₃ | SO₂CH₂(4-MePh) | Me | CH(Me)Ph | H |
| 1-1151 | CF₃ | SO₂NHMe | Me | i-Pr | H |
| 1-1152 | CF₃ | SO₂NHMe | Me | t-Bu | H |
| 1-1153 | CF₃ | SO₂NHMe | Me | s-Bu | H |
| 1-1154 | CF₃ | SO₂NHMe | Me | i-Bu | H |
| 1-1155 | CF₃ | SO₂NHMe | Me | CH(Me)CH₂OMe | H |
| 1-1156 | CF₃ | SO₂NHMe | Me | CH(Me)Ph | H |
| 1-1157 | CF₃ | SO₂NMe₂ | Me | i-Pr | H |
| 1-1158 | CF₃ | SO₂NMe₂ | Me | t-Bu | H |
| 1-1159 | CF₃ | SO₂NMe₂ | Me | s-Bu | H |
| 1-1160 | CF₃ | SO₂NMe₂ | Me | i-Bu | H |
| 1-1161 | CF₃ | SO₂NMe₂ | Me | CH(Me)CH₂OMe | H |
| 1-1162 | CF₃ | SO₂NMe₂ | Me | CH(Me)Ph | H |

Next, although production methods of the isoxazolin-5-one derivatives represented by the formula (1) of the invention are explained in detail, the production methods are not limited to these methods. In this regard, regarding the reaction devices, reaction using a microwave synthesis device is also possible in addition to reaction using a magnetic stirrer or a mechanical stirrer.

[Production Method 1]

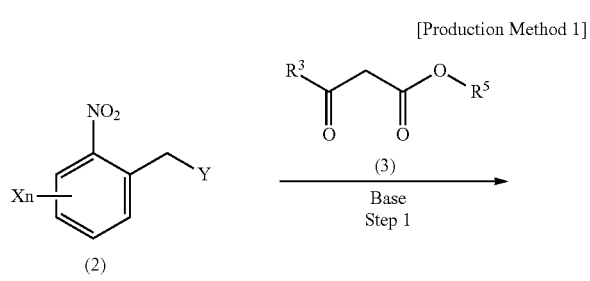

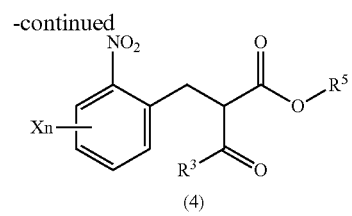

($R^3$, X and n have the same meanings as those described above. Y represents a leaving group such as a halogen atom, a methanesulfonyloxy group, a trifluoromethanesulfonyloxy group or a toluenesulfonyloxy group. $R^5$ represents a C1-C6 alkyl group.)

The step-1 is a step of reacting a nitrobenzene derivative represented by the formula (2) and a β-ketoester derivative represented by the formula (3) in the presence of a base and thus producing a 2-(2-nitrobenzyl)-β-ketoester derivative (4). The nitrobenzene derivative represented by the formula (2) and the β-ketoester derivative represented by the formula (3) are sometimes known and can be obtained from Tokyo Chemical Industry Co., Ltd. or the like. Alternatively, the derivatives can also be easily produced from an available reagent according to a known method described in Courses in Experimental Chemistry, Organic Syntheses or the like.

It is necessary to conduct the reaction in the presence of a base, and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. Of these bases, a metal base such as sodium methoxide and sodium ethoxide is preferable in view of the high yield. By conducting the reaction using the base in an amount of 0.1 to 5 equivalents based on the substrates, the target material can be obtained with a high yield. The reaction substrate (3) is generally used in an amount of 1 to 5 equivalents based on the substrate (2).

The reaction is preferably conducted in the presence of a solvent. A solvent which does not adversely affect the reaction can be used as the solvent used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water or a mixed solvent thereof can be used. To promote the progress of the reaction, a phase-transfer catalyst such as a quaternary ammonium salt can also be added.

The reaction can be conducted at a temperature which is appropriately determined in the range of from −78° C. to 200° C., although the temperature varies with the reaction conditions. After the reaction, although the target material can be obtained by a general post-treatment operation, the target material can also be purified by column chromatography, recrystallization or the like if necessary.

($R^3$, X, n and $R^5$ have the same meanings as those described above.)

The step-2 is a step of reacting the 2-(2-nitrobenzyl)-3-ketoester derivative represented by the formula (4) and hydroxylamine represented by the formula (5) and thus producing an isoxazolin-5-one derivative (6). The hydroxylamine represented by the formula (5) may be a quaternary salt such as a hydrochloride or a sulfate.

The reaction may be conducted in the presence of a base, and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. By conducting the reaction using the base in an amount of 0.1 to 5 equivalents based on the substrates, the target material can be obtained with a high yield. The reaction substrate (5) is generally used in an amount of 1 to 5 equivalents based on the substrate (4).

The reaction is preferably conducted in a solvent. A solvent which does not adversely affect the reaction can be used as the solvent, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water or a mixed solvent thereof can be used.

The reaction can be conducted at a temperature which is appropriately determined in the range of from −78° C. to 200° C., although the temperature varies with the base used and the reaction conditions. After the reaction, although the target material can be obtained by a general post-treatment operation, the target material can also be purified by column chromatography, recrystallization or the like if necessary.

[Production Method 2]

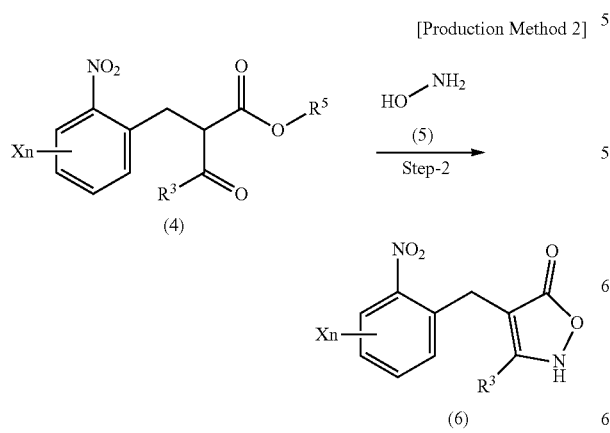

[Production Method 3]

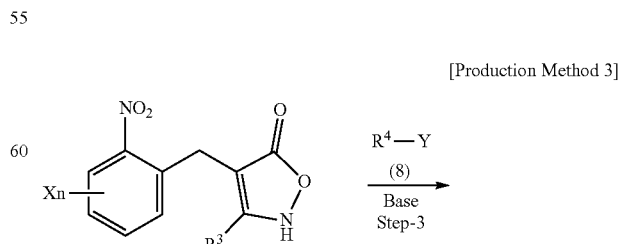

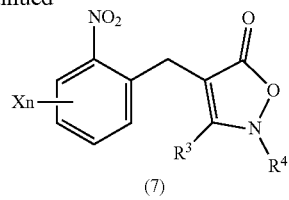

(7)

($R^3$, $R^4$, X, n and Y have the same meanings as those described above.)

The step-3 is a step of introducing $R^4$ to the nitrogen atom at the 2-position of the isoxazolin-5-one derivative represented by the formula (6) and thus producing an isoxazolin-5-one derivative represented by the formula (7).

It is necessary to conduct the reaction in the presence of a base, and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. Of these bases, a metal base such as potassium carbonate and sodium hydride is preferable in view of the high yield. By conducting the reaction using the base in an amount of 0.1 to 5 equivalents based on the substrates, the target material can be obtained with a high yield. The reaction substrate (8) is generally used in an amount of 1 to 5 equivalents based on the substrate (6).

The reaction is preferably conducted in a solvent. A solvent which does not adversely affect the reaction can be used as the solvent, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water or a mixed solvent thereof can be used.

The reaction can be conducted at a temperature which is appropriately determined in the range of from −78° C. to 200° C., although the temperature varies with the base used and the reaction conditions. After the reaction, although the target material can be obtained by a general post-treatment operation, the target material can also be purified by column chromatography, recrystallization or the like if necessary. Additionally, an O-substitution product may be generated in the reaction but can be easily separated and purified by column chromatography or the like.

[Production Method 4]

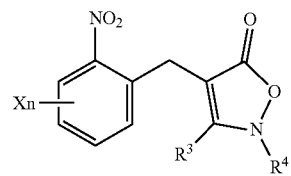

(7)

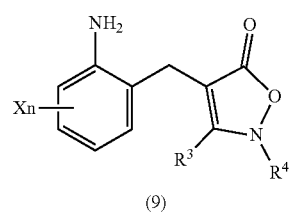

(9)

($R^3$, $R^4$, X and n have the same meanings as those described above.)

The step-4 is a step of reducing the nitro group of the isoxazolin-5-one derivative represented by the formula (7) and thus producing an isoxazolin-5-one derivative (9) having an amino group.

The method for reducing the nitro group in the step can be a method using a reducing agent such as zinc powder, reduced iron, tin powder, stannous chloride and titanium chloride, a method using a hydrogen donor such as hydrazine in the presence of Raney nickel, catalytic hydrogenation reduction or catalytic hydrogen transfer reduction in the presence of a catalyst such as Raney nickel, palladium on carbon, palladium hydroxide and platinum oxide or the like.

The reaction is preferably conducted in a solvent. A solvent which does not adversely affect the reaction can be used as the solvent, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water, hydrochloric acid, acetic acid or a mixed solvent thereof can be used.

The reaction can be conducted at a temperature which is appropriately determined in the range of from 0° C. to 200° C., although the temperature varies with the base used and the reaction conditions. After the reaction, although the target material can be obtained by a general post-treatment operation, the target material can also be purified by column chromatography, recrystallization or the like if necessary.

[Production Method 5]

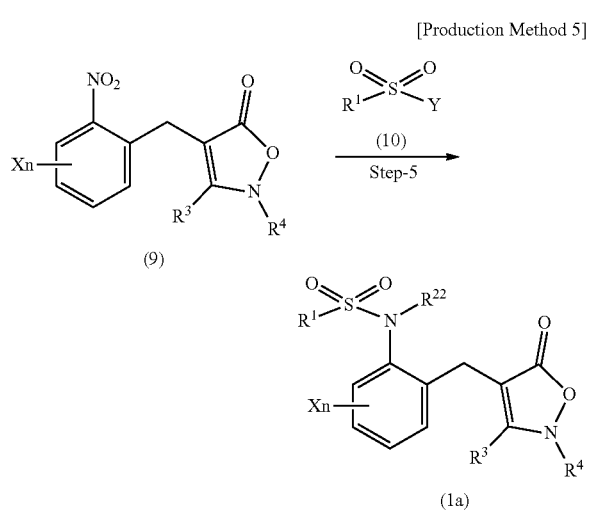

($R^1$, $R^3$, $R^4$, X, n and Y have the same meanings as those described above. $R^{22}$ represents a hydrogen atom or $R^1SO_2$.)

The step-5 is a step of reacting the isoxazolin-5-one derivative having an amino group represented by the formula (9) and a compound represented by the formula (10) and thus producing an isoxazolin-5-one derivative (la).

The reaction may be conducted in the presence of a base, and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. Of these bases, an organic base such as triethylamine and diisopropylethylamine is preferable in view of the high yield. By conducting the reaction using the base in an amount of 0.1 to 5 equivalents based on the substrates, the target material can be obtained with a high yield.

The reaction is preferably conducted in a solvent. A solvent which does not adversely affect the reaction can be used as the solvent, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water or a mixed solvent thereof can be used.

The reaction can be conducted at a temperature which is appropriately determined in the range of from −78° C. to 200° C., although the temperature varies with the base used and the reaction conditions. After the reaction, although the target material can be obtained by a general post-treatment operation, the target material can also be purified by column chromatography, recrystallization or the like if necessary.

[Production Method 6]

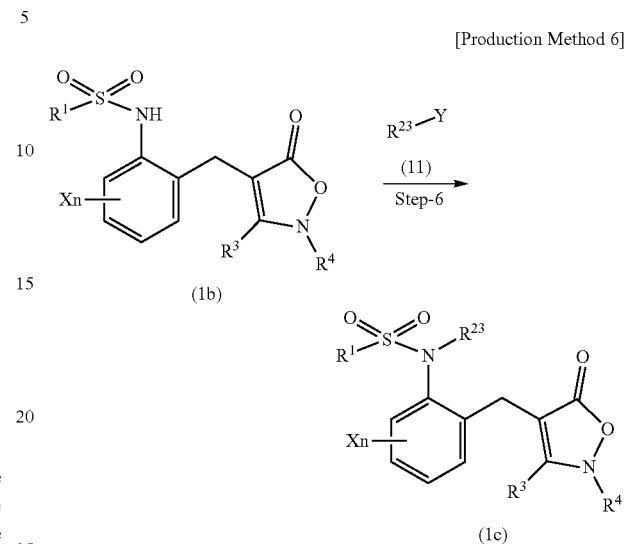

($R^1$, $R^3$, $R^4$, X, n and Y have the same meanings as those described above. $R^{23}$ represents any of the groups in $R^2$ except for hydrogen atom.)

The step-6 is a step of reacting a compound represented by the formula (11) with an isoxazolin-5-one derivative represented by the formula (1b) and thus producing an isoxazolin-5-one derivative (1c).

It is necessary to conduct the reaction in the presence of a base depending on the kind of the compound (11), and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. By conducting the reaction using the base in an amount of 0.1 to 5 equivalents based on the substrates, the target material can be obtained with a high yield.

The reaction is preferably conducted in a solvent. A solvent which does not adversely affect the reaction can be used as the solvent, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water or a mixed solvent thereof can be used.

The reaction can be conducted at a temperature which is appropriately determined in the range of from −78° C. to 200° C., although the temperature varies with the base used and the reaction conditions. After the reaction, although the target material can be obtained by a general post-treatment operation, the target material can also be purified by column chromatography, recrystallization or the like if necessary.

[Production Method 7]

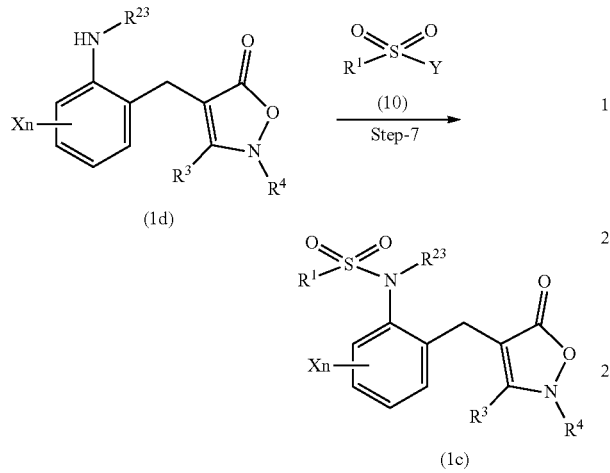

($R^1$, $R^3$, $R^4$, $R^{23}$, X, n and Y have the same meanings as those described above.)

The step-7 is a step of reacting the sulfonyl compound represented by the formula (10) with an isoxazolin-5-one derivative represented by the formula (1d) and thus producing the isoxazolin-5-one derivative (1c).

The reaction may be conducted in the presence of a base, and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. By conducting the reaction using the base in an amount of 0.1 to 5 equivalents based on the substrates, the target material can be obtained with a high yield.

The reaction is preferably conducted in a solvent. A solvent which does not adversely affect the reaction can be used as the solvent, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water or a mixed solvent thereof can be used.

The reaction can be conducted at a temperature which is appropriately determined in the range of from −78° C. to 200° C., although the temperature varies with the base used and the reaction conditions. After the reaction, although the target material can be obtained by a general post-treatment operation, the target material can also be purified by column chromatography, recrystallization or the like if necessary.

[Production Method 8]

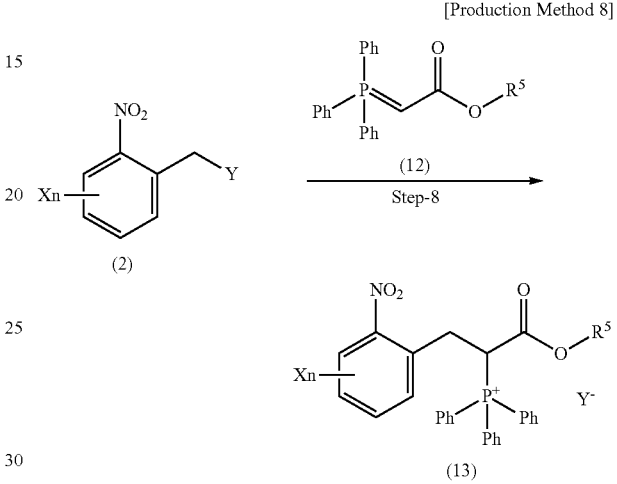

(X, n, Y and $R^5$ have the same meanings as those described above.)

The step-8 is a step of reacting the nitrobenzene derivative represented by the formula (2) and a phosphonium ylide derivative represented by the formula (12) and thus producing a phosphonium salt derivative (13). The phosphonium ylide derivative represented by the formula (12) is sometimes known and can be obtained from Tokyo Chemical Industry Co., Ltd. or the like. Alternatively, the derivative can also be easily produced from an available reagent according to a known method described in Courses in Experimental Chemistry, Organic Syntheses or the like.

The reaction is preferably conducted in the presence of a solvent. A solvent which does not adversely affect the reaction can be used as the solvent used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a halogen-based solvent such as chloroform, dichloromethane and 1,2-dichloroethane, an ester-based solvent such as ethyl acetate, propyl acetate, butyl acetate and methyl propionate, an amide-based solvent such as N,N-dimethylformamide, N,N-dimethylacetamide and N-methylpyrrolidone, dimethyl sulfoxide or a mixed solvent thereof can be used. To promote the progress of the reaction, a phase-transfer catalyst such as a quaternary ammonium salt can also be added.

The reaction can be conducted at a temperature which is appropriately determined in the range of from −78° C. to 200° C., although the temperature varies with the reaction conditions. After the reaction, although the target material can be obtained by a general post-treatment operation, the target material can also be purified by column chromatography, recrystallization or the like if necessary.

[Production Method 9]

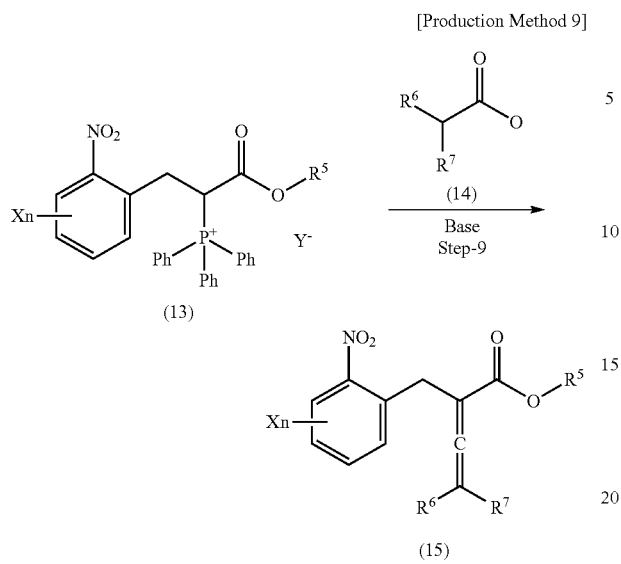

[Production Method 10]

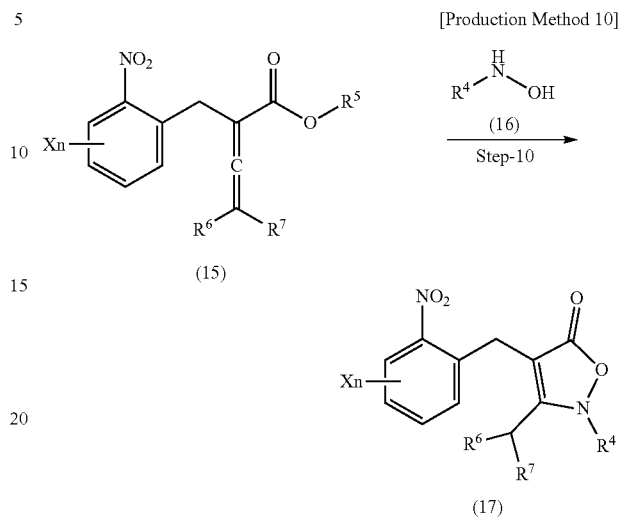

(X, n, Y and $R^5$ have the same meanings as those described above. Z represents a halogen atom. $R^6$ represents a hydrogen atom or a C1-C6 alkyl group. $R^7$ represents a hydrogen atom or a C1-C6 alkyl group.)

The step-9 is a step of reacting the phosphonium salt derivative represented by the formula (13) and an acyl halide derivative represented by the formula (14) in the presence of a base and thus producing an allenoate derivative (15).

It is necessary to conduct the reaction in the presence of a base, and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. Of these bases, an organic base such as triethylamine and diisopropylethylamine is preferable in view of the high yield. By conducting the reaction using the base in an amount of 0.1 to 5 equivalents based on the substrates, the target material can be obtained with a high yield. The reaction substrate (14) is generally used in an amount of 1 to 5 equivalents based on the substrate (13).

The reaction is preferably conducted in the presence of a solvent. A solvent which does not adversely affect the reaction can be used as the solvent used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a halogen-based solvent such as chloroform and dichloromethane or a mixed solvent thereof can be used.

The reaction can be conducted at a temperature which is appropriately determined in the range of from −78° C. to 200° C., although the temperature varies with the reaction conditions. After the reaction, although the target material can be obtained by a general post-treatment operation, the target material can also be purified by column chromatography, recrystallization or the like if necessary.

(X, n, $R^4$, $R^5$, $R^6$ and $R^7$ have the same meanings as those described above.)

The step-10 is a step of reacting the allenoate derivative represented by the formula (15) and a hydroxylamine derivative represented by the formula (16) and thus producing an isoxazolin-5-one derivative (17). The hydroxylamine derivative represented by the formula (16) is sometimes known and can be obtained from Tokyo Chemical Industry Co., Ltd. or the like. Alternatively, the derivative can also be easily produced from an available reagent according to a known method described in Courses in Experimental Chemistry, Organic Syntheses or the like. The hydroxylamine derivative represented by the formula (16) may be a quaternary salt such as a hydrochloride or a sulfate.

The reaction may be conducted in the presence of a base, and as the base, an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline and lutidine, an alkali metal salt such as sodium carbonate, potassium carbonate, sodium hydrogen carbonate, potassium hydrogen carbonate, sodium acetate, potassium acetate, sodium methoxide, sodium ethoxide, potassium-tert-butoxide, sodium hydride, potassium hydride, sodium amide, butyllithium, tert-butyllithium, lithium diisopropylamide, trimethylsilyl lithium and lithium hexamethyldisilazide or the like can be used. Of these bases, an organic base such as triethylamine and diisopropylamine is preferable in view of the high yield. By conducting the reaction using the base in an amount of 0.1 to 5 equivalents based on the substrates, the target material can be obtained with a high yield. The reaction substrate (16) is generally used in an amount of 1 to 5 equivalents based on the substrate (15).

The reaction is preferably conducted in the presence of a solvent. A solvent which does not adversely affect the reaction can be used as the solvent used, and an aromatic hydrocarbon-based solvent such as benzene, toluene, xylene and chlorobenzene, an aliphatic hydrocarbon-based solvent such as pentane, hexane and octane, an ether-based solvent such as diethyl ether, diisopropyl ether, cyclopentyl methyl ether, tetrahydrofuran, dimethoxyethane and 1,4-dioxane, a ketone such as acetone, methyl ethyl ketone and cyclohexanone, a halogen-based solvent such as chloroform and dichloromethane, a nitrile-based solvent such as acetonitrile and propionitrile, an ester-based solvent such as ethyl acetate, propyl acetate, butyl acetate and methyl propionate, an amide-based solvent such as N,N-dimethylformamide, N,N-dimethylacetamide and N-methylpyrrolidone, an alcohol-based solvent such as methanol, ethanol, 1-propanol, 2-propanol and tert-butanol, dimethyl sulfoxide, water or a mixed solvent thereof can be used.

The reaction can be conducted at a temperature which is appropriately determined in the range of from −78° C. to 200° C., although the temperature varies with the reaction conditions. After the reaction, although the target material can be obtained by a general post-treatment operation, the target material can also be purified by column chromatography, recrystallization or the like if necessary.

The compounds of the invention can be analyzed, confirmed or identified by the melting points, the infrared absorption spectra, $^1$H-NMR, $^{13}$C-NMR, mass spectrometry, X-ray structure analysis or the like, if necessary.

The production methods are not limited to those described above, and the compounds of the invention can be produced by any organic synthesis methods.

As also shown in Test Examples described below, the compounds of the invention exhibit an excellent herbicidal activity and exhibit an excellent selective weed killing activity distinguishing the weeds and the crops below. Thus, the compounds can be used for a wide range of targets such as weeds and the like in paddy rice fields and dry field. Specific examples of the weeds are as follows.

Specifically, for example, the following harmful weeds can be controlled: Gramineae weeds such as *Echinochloa crus-galli, Echinochloa oryzicola*, southern crabgrass (*Digitaria sanguinalis, Digitaria ischaem, Digitaria adscendens, Digitaria microbachne* or *Digitaria horizontalis*), *Setaria viridis, Setaria faberi, Setaria lutescens, Eleusine indica, Avena fatua, Sorghum halepense, Aropyron repens, Brachiaria plantaginea, Panicum maximum, Panicum purpurascens, Panicum dichotomiflorum, Leptochloa chinensis, Leptochloa panicea, Poa annua, Alopecurus aequalis, Alopecurus myosuroides, Agropyron tsukushiense, Bracharia platyphylla, Cenchrus echinatus, Lolium multiflorum, Cynodon dactylon, Beckmannia syzigache, Bromus catharticus, Leersia japonica, Leersia sayanuka, Lolium rigidum, Paspalum distichum* and *Phleum pratense*; Cyperaceae weeds such as *Cyperus iria, Cyperus rotundus, Cyperus esculentus, Scirpus hotarui, Cyperus serotinus, Cyperus serotinus, Eleocharis acicularis, Eleocharis kuroguwai, Cyperus flaccidus, Kyllinga brevifolia* and *Scirpus juncoides*; Alismataceae weeds such as *Sagittaria pygmaea, Sagittaria trifolia* and *Alisma canaliculatum*; Pontderiaceae weeds such as *Monochoria vaginalis, Heteranthera limosa* and *Monochoria kosakowii*; Linderniaceae weeds such as *Lindernia pyxidaria*; Plantaginaceae weeds such as *Plantago asiatica, Gratiola japonica, Dopatrium junceum* and *Veronica polita*; Lythraceae weeds such as *Rotala india, Ammannia multifflora* and *Rotala indica*; Elatinaceae weeds such as *Elatine triandra*; Malvaceae weeds such as *Abutiol theophrsti* and *Sida spinosa*; Compositae weeds such as *Xanthium strumarim, Ambrosia elatior, Breea serosa, Galinsoga ciliata, Matricaria chamomilla, Taraxacum officinale, Erigeron canadensis, Bidens frondosa, Bidens pilosa, Bidens tripartita, Gnaphalium affine* and *Senecio vulgaris*; Lamiaceae weeds such as *Lamium amplexinale weber*; Solanaceae weeds such as *Solanum nigrum* and *Datura stramonium*; Amaranthaceae weeds such as *Amaranthus viridis, Chenopodium album, Kochia scoparia* and *Amaranthus hybridus*; Polygonaceeae weeds such as *Polygonum lapathifolium, Polygonum persicaria, Polygonum convolvulus, Polygonum aviculare, Persicaria longiseta* and *Persicaria nepalensis*; Crpurea weeds such as *Cardamine flexuosa, Capsella bursapastoris, Brassica juncea* and *Rorippa indica*; Convolvulaceae weeds such as *Ipomoea purpurea, Convolvulus arvensis, Ipomoea hederacea, Calystegia pubescens* and *Ipomoea coccinea*; Portulacaceae weeds such as *Portulaca oleracea*; Fabaceae weeds such as *Cassia obtusifolia, Aeschynomene indica, Sesbania exaltata, Trifolium repens* and *Vicia sativa*; Caryophyllaceae weeds such as *Stellaria media, Stellaria neglecta* and *Stellaria uliginosa*; Euphoribiaceae weeds such as *Euphorbia helioscopia* and *Acalypha australis*; Commelinaceae weeds such as *Commelina communis* and *Murdannia keisak*; Potamogetonaceae weeds such as *Potamogeton distinctus*; Araceae weeds such as *Spirodela polyrhiza*; Cucurbitaceae weeds such as *Sicyos angulatus*; Rubiaceae weeds such as *Galium spurium*; Apiaceae weeds such as *Oenanthe javanica*; Violaceae weeds such as *Viola mandshuria*; Onagraceae weeds such as *Ludwigia epilobioides* and *Oenothera odorata*; Oxalidaceae weeds such as *Oxalis corniculata*; Equisetaceae weeds such as *Equisetum arvense*; Zygnemataceae weeds such as Spirogyra sp. and the like. Accordingly, the compounds are effectively used for a case of selectively controlling a harmful weed or a case of non-selectively controlling a harmful weed in culturing, for example, *Zea mays, Glycine max, Gossypium* spp., *Triticum* spp., *Hordeum vulgare, Secale cereale, Avena sativa, Sorghum bicolor, Brassica napus, Helianthus annuus, Beta Vulgaris, Saccharum officinarum, Zoysia japonicaa, Arachis hypogaea, Linum usitatissmum, Nicotiana tabacum, Coffea* spp. or the like, which are useful crops.

The applications of the herbicides of the invention are not limited to the weeds and the crops described above as examples.

If necessary, the compounds of the invention may be prepared as mixed formulations with another kind of herbicide, an insecticide, an acaricide, a nematicide, a germicide (a fungicide, a bactericide, an antiviral agent or a plant resistance inducer), a bird repellent, a plant growth regulator, a safener, a fertilizer, a soil conditioner, a synergist or the like during the formation or spraying or may be blended with such an agent in a tank mixer at spraying and applied.

In particular, when the compounds are blended and applied with another kind of herbicide, the amount of the used herbicide can be reduced, and the labor can be reduced. Moreover, the range of the targets of the herbicides (weed control spectrum) broadens due to the multiplier action of the agents, and a stronger effect can be expected due to the synergistic action of the agents. At this point, more than one kind of known herbicide or safener can also be combined and blended at the same time.

Of the optional components above, although representative examples of herbicides are shown below, the components are not limited to these examples only.

(1) Phenoxy-based compounds such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium 2,4-D choline salt, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioetyl, MCPB, MCPB-ethyl, MCPB-sodium, mecoprop, mecoprop-butotyl, mecoprop-sodium, mecoprop-P, mecoprop-P-butotyl, mecoprop-P-dimethyl ammonium, mecoprop-P-2-ethylhexyl, mecoprop-P-potassium, naproanilide, clomeprop and HIA-1; aromatic carboxylic acid-based compounds such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, picloram, picloram-dimethylammonium, picloram-isooctyl, picloram-potassium, picloram-trii sopropanolammonium, picloram-trii sopropylammonium, picloram-trolamine, tricolopyr, tricolopyr-butotyl, tricolopyr-triethylammonium, clopyralid, clopyralid-olamine, clopyralid-potassium, clopyralid-triisopropanolammonium, aminopyralid, aminocyclopyrachlor, aminocyclopyrachlor, halauxifen, florpyrauxifen, halauxifen-methyl and DAS-534; and other compounds which are considered to exhibit a herbicidal efficacy by disturbing the hormone action of a plant, such as naptalam, naptalam-sodium, benazolin, benazolin-ethyl, quinclorac, quinmerac, diflufenzopyr, diflufenzopyr-sodium, fluroxypyr, fluroxypyr-2-butoxy-1-methylethyl, fluroxypyr-meptyl, chlorflurenol, chlorflurenol-methyl and clacyfos.

(2) Urea-based compounds such as chlorotoluron, diuron, fluometuron, linuron, isoproturon, metobenzuron, tebuthiuron, dimefuron, isouron, karbutilate, methabenztiazuron, metoxuron, metoburomuron, monolinuron, neburon, siduron, terbumeton and trietazine; triazine-based compounds such as simazine, atrazine, atratone, simetryn, prometryn, dimethametryn, hexazinone, metribuzin, terbuthylazine, cyanazine, ametryn, cybutryne, terbutryn, propazine, metamitron and prometon; uracil-based compounds such as bromacil, bromacyl-lithium, lenacil and terbacil; anilide-based compounds such as propanil and cypromid; carbamate-based compounds such as swep, desmedipham and phenmedipham; hydroxybenzonitrile-based compounds such as bromoxynil, bromoxynil-octanoate, bromoxynil-heptanoate, ioxynil, ioxynil-octanoate, ioxynil-potassium and ioxynil-sodium; and other compounds which are considered to exhibit a herbicidal efficacy by inhibiting the photosynthesis of a plant, such as pyridate, bentazone, bentazone-sodium, amicarbazone, methazole, pentanochlor and phenmedipham.

(3) Quaternary ammonium salt-based compounds which become free radicals in the plant and which are considered to generate active oxygen and exhibit an immediate herbicidal efficacy, such as paraquat and diquat.

(4) Diphenyl ether-based compounds such as nitrofen, chlomethoxyfen, bifenox, acifluorfen, acifluorfen-sodium, fomesafen, fomesafen-sodium, oxyfluorfen, lactofen, aclonifen, ethoxyfen-ethyl, fluoroglycofen-ethyl and fluoroglycofen; cyclic imide-based compounds such as chlorphthalim, flumioxazin, flumiclorac, flumiclorac-pentyl, cinidon-ethyl, fluthiacet-methyl and EK-5385; and other compounds which are considered to exhibit a herbicidal efficacy by inhibiting chlorophyll biosynthesis of a plant and causing abnormal accumulation of a photosensitizing peroxide substance in the plant, such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, fluazolate, profluazol, flufenpyr-ethyl, bencarbazone, tiafenacil, pyrachlonil, trifludimoxazin, HNPC-B4047, IR-6396, EK-5498, SYN-523 and the compound described in WO2008/008763 (FMC).

(5) Pyridazinone-based compounds such as norflurazon, chloridazon and metflurazon; pyrazole-based compounds such as pyrazolynate, pyrazoxyfen, benzofenap, topramezone, pyrasulfotole and tolpyralate; and other compounds which are considered to exhibit a herbicidal efficacy characterized by a bleaching effect by inhibiting biosynthesis of a pigment of a plant such as carotenoids, such as amitrole, fluridone, flurtamone, diflufenican, methoxyphenone, clomazone, sulcotrione, mesotrione, tembotrione, tefuryltrione, fenquinotrione, lancotrione, cyclopyrimorate, isoxaflutole, difenzoquat, difenzoquat-metilsulfate, isoxachlortole, benzobicyclon, bicyclopyron, picolinafen, beflubutamid, ketospiradox, ketospiradox-potassium and compounds described in JP2012/2571 (Sumitomo Chemical Company, Limited).

(6) Compounds which are considered to inhibit biosynthesis of fatty acids and exhibit a herbicidal efficacy on a plant including aryloxyphenoxypropionic acid-based compounds such as diclofop-methyl, diclofop, pyriphenop-sodium, fluazifop-butyl, fluazifop, fluazifop-P, fluazifop-P-butyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, propaquizafop, HNPC-A8169 and SYP-1924; cyclohexanedione-based compounds such as alloxydim-sodium, alloxydim, clethodim, sethoxydim, tralkoxydim, butroxydim, tepraloxydim, profoxydim and cycloxydim; phenylpyrazoline-based compounds such as pinoxaden; and the like.

(7) Sulfonylurea compounds such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, flazasulfuron, rimsulfuron, nicosulfuron, imazosulfuron, flucetosulfuron, cyclosulfamuron, prosulfuron, flupyrsulfuron-methyl-sodium, flupyrsulfuron, triflusulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, amidosulfuron, azimsulfuron, propyrisulfuron, metazosulfuron, methiopyrsulfuron, monosulfuron-methyl, orsosulfuron, iofensulfuron and iofensulfuron-sodium; triazolopyrimidinesulfonamide-based compounds such as flumetsulam, metosulam, diclosulam, cloransulam-methyl, florasulam, penoxsulam and pyroxsulam; imidazolinone-based compounds such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl and imazapic; pyrimidinyl salicylic acid-based compounds such as pyrithiobac-sodium, bispyribac-sodium, pyriminobac-methyl, pyribenzoxim, pyriftalid, pyrimisulfan and triafamone; sulfonylaminocarbonyltriazolinone-based compounds such as flucarbazone, flucarbazone-sodium, propoxycarbazone-sodium, propoxycarbazone and thiencarbazone-methyl; and other compounds which are considered to exhibit a herbicidal efficacy by inhibiting amino acid biosynthesis of a plant, such as glyphosate, glyphosate-sodium, glyphosate-potassium, glyphosate-ammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium and cinmethylin.

(8) Dinitroaniline-based compounds such as trifluralin, oryzalin, nitralin, pendimethalin, ethalfluralin, benfluralin, prodiamine, butralin and dinitramine; amide-based compounds such as bensulide, napropamide, napropamide-M, propyzamide and pronamide; organic phosphorus-based compounds such as amiprofos-methyl, butamifos, anilofos and piperophos; phenyl carbamate-based compounds such as propham, chlorpropham, barban and carbetamide; cumylamine-based compounds such as daimuron, cumyluron, bromobutide and methyldymron; and other compounds which are considered to exhibit a herbicidal efficacy by inhibiting cell mitosis of a plant, such as asulam, asulam-sodium, dithiopyr, thiazopyr, chlorthal-dimethyl, chlorthal, diphenamid, flamprop-M-methyl, flamprop-M and flamprop-M-isopropyl.

(9) Chloroacetamide-based compounds such as alachlor, metazachlor, butachlor, pretilachlor, metolachlor, S-metolachlor, thenylchlor, pethoxamid, acetochlor, propachlor, dimethenamide, dimethenamide-P, propisochlor and dimethachlor; thiocarbamate-based compounds such as molinate, dimepiperate, pyributicarb, EPTC, butylate, vernolate, cycloate, prosulfocarb, esprocarb, thiobencarb, diallate, triallate and orbencarb; and other compounds which are considered to exhibit a herbicidal efficacy by inhibiting protein biosynthesis or lipid biosynthesis of a plant, such as etobenzanid, mefenacet, flufenacet, tridiphane, cafenstrole, fentrazamide, ipfencarbazone, oxaziclomefone, indanofan, benfuresate, pyroxasulfone, fenoxasulfone, methiozolin, dalapon, dalapon-sodium, TCA-sodium and trichloracetic acid.

(10) Compounds which are considered to exhibit a herbicidal efficacy by inhibiting cellulose biosynthesis of a plant, such as dichlobenil, triaziflam, indaziflam, flupoxam and isoxaben.

(11) Other herbicides such as MSMA, DSMA, CMA, endothall, endothall-dipotassium, endothall-sodium, endothall-mono(N,N-dimethylalkylammonium), ethofumesate, sodium chlarate, pelargonic acid, nonanoic acid, fosamine, fosamine-ammonium, aclolein, ammonium sulfamate, borax, chloroacetic acid, sodium chloroacetate, cyanamide, methylarsonic acid, dimethylarsonic acid, sodium dimethylarsonate, dinoterb, dinoterb-ammonium, dinoterb-diolamine, dinoterb-acetate, DNOC, ferrous sulfate, flupropanate, flupropanate-sodium, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, zanthinosin, herbimycin, unguinol, metatyrosine, sarmentine, thaxtomin A, mevalocidin, alpha-limonene, pyribambenz-propyl, pyribambenz-isopropyl, JS-913, KHG-23844, H-9201, SIOC-0163, SIOC-0171, SIOC-0172, SIOC-0285, SIOC-0426, SIOC-H-057, ZJ-0166, ZJ-1835, ZJ-0453, ZJ-0777, ZJ-0862 and compounds described in WO2008/096398 (Kumiai Chemical Industry Co., Ltd.).

(12) Those which are considered to exhibit a herbicidal efficacy by parasitizing in a plant, such as *Xanthomonas campestris, Epicoccosirus nematosorus, Epicoccosirus nematosperus, Exserohilum monoseras* and *Drechsrela monoceras*.

When the compounds of the invention are used as herbicides, the compounds can be directly used but can also be used as formulations. To prepare the formulations, an appropriate carrier, an auxiliary agent, a surfactant, a binder, a stabilizer and the like described in Pesticide Formulation Guide (edited by Special Committee on Application of Pesticide Science Society of Japan, issued by Japan Plant Protection Association, 1997).

The herbicides containing the compounds of the invention can be formulated into any agent forms which are generally used as agent forms. For example, although the herbicides can be used in the forms of granules, microgranules, fine granules, water dispersible powder, a granulate water dispersible (dry flowable) agent, an emulsion, water soluble powder, a sol agent (flowable agent), a liquid, powder, rough powder, DL (driftless) powder, a flow dust agent, an oil, a microcapsule, a paste, a jumbo agent and the like, the forms are not limited to these examples.

As the carrier used for formulation, both solid and liquid can be used as long as the carrier is generally used for herbicide formulations. Although the carrier is not limited to a particular carrier, specific examples include the following carriers. Examples of the solid carrier include mineral powders (kaolin, bentonite, clay, montmorillonite, talc, diatomaceous earth, mica, vermiculite, quartz, calcium carbonate, apatite, white carbon, slaked lime, silica sand, Japanese acid clay, zeolite, sepiolite, expanded perlite powder, Shirasu-balloon, alumina balloon, a phenolic resin, an epoxy resin, polyacrylonitrile, microspheres of polyurethane or the like and the like), vegetable powders (soybean flour, wheat flour, wood flour, tobacco powder, starch, crystalline cellulose and the like), polymer compounds (a petroleum resin, polyvinyl chloride, a ketone resin and the like), alumina, silicate, glucose, sucrose, lactose, glycopolymers, ammonium sulfate, sodium chloride, potassium chloride, urea, highly dispersible silicic acid, waxes and the like.

Examples of the liquid carrier include water, alcohols (methyl alcohol, ethyl alcohol, n-propyl alcohol, isopropyl alcohol, butanol, ethylene glycol, benzyl alcohol and the like), aromatic hydrocarbons (toluene, benzene, xylene, ethyl benzene, methylnaphthalene and the like), ethers (ethyl ether, ethylene oxide, dioxane, tetrahydrofuran and the like), ketones (acetone, methyl ethyl ketone, cyclohexanone, methyl isobutyl ketone, isophorone and the like), esters (ethyl acetate, butyl acetate, ethylene glycol acetate, amyl acetate and the like), acid amides (dimethylformamide, dimethylacetamide and the like), nitriles (acetonitrile, propionitrile, acrylonitrile and the like), sulfoxides (dimethyl sulfoxide and the like), alcoholethers (ethylene glycol monomethyl ether, ethylene glycol monoethyl ether and the like), aliphatic or alicyclic hydrocarbons (n-hexane, cyclohexane and the like), industrial gasoline (petroleum ether, solvent naphtha and the like), petroleum fractions (paraffin, kerosene, light oil and the like) and the like.

When the herbicides are formulated into an emulsion, water dispersible powder, a flowable agent or the like, various kinds of surfactant are blended for the purpose of emulsification, dispersion, solubilization, wetting, foaming, lubrication, spreading or the like. Examples of such a surfactant include nonionic surfactants such as polyoxyethylene alkyl ethers, polyoxyethylene alkyl esters, polyoxyethylene sorbitan alkyl esters, polyoxyethylenealkyl aryl ethers, polyoxyethylene-polyoxypropylene block polymers and polyoxyethylene styrylphenylethers, anionic surfactants such as alkylbenzene sulfonates, alkyl sulfosuccinates, alkyl sulfates, polyoxyethylene alkyl sulfates, aryl sulfonates, alkylnaphthalene sulfonates, polyoxyethylene styrylphenylether sulfates, lignin sulfonates, naphthalene sulfonate formaldehyde condensate and polycarboxylates, cationic surfactants such as alkylamines (lauryl amine, stearyltrimethyl ammonium chloride and the like), polyoxyethylene alkyl amines, alkyl pyridinium salts, alkyltrimethyl ammonium salts and alkyldimethyl ammonium salts, ampholytic surfactants such as carboxylic acid (betaine type) and sulfate esters and the like, but the surfactant is not limited to the examples.

In addition, various kinds of auxiliary agent and additive such as polyvinyl alcohol (PVA), carboxymethyl cellulose (CMC), gum arabic, polyvinyl acetate, sodium alginate, gelatin, tragacanth gum, dextrin, hydroxypropyl methylcellulose (HPMC) and methyl cellulose (MC) and the like can be used.

An appropriate amount of the compound of the invention in the herbicide is around 0.01 to 90% based on the mass.

Preferable methods for using the herbicides containing the compounds of the invention as active ingredients include soil treatment, water surface treatment, leave and stem treatment and the like, and the herbicides can exhibit a particularly excellent effect when applied before germination and during the plumule period of a weed to be controlled.

Although the amount of the compound of the invention to be applied as an herbicide differs with the situation of the application, the time of the application, the application method, the target weed, the cultivated crop and the like, an appropriate amount of the active ingredient is generally around 0.001 to 10 Kg, and preferably around 0.01 to 1 Kg per hectare (ha).

EXAMPLES

Although the invention is explained further specifically below using Synthesis Examples, Formulation Examples and Test Examples of the compounds of the invention, the invention is not limited to the examples.

Synthesis Example 1

Synthesis of 1,1,1-trifluoro-N-[2-[(2-isobutyl-3-methyl-5-oxoisoxazol-4-yl)methyl]phenyl]methanesulfonamide (1-105) and 1,1,1-trifluoro-N-[2-[(2-isobutyl-3-methyl-5-oxoisoxazol-4-yl)methyl]phenyl]-N-(trifluoromethylsulfonyl)methanesulfonamide (1-967

Triethylamine (200 mg, 2.00 mmol) and trifluoromethanesulfonic acid anhydride (400 mg, 1.40 mmol) were added at 0° C. to a chloroform solution (10 ml) of 4-[(2-aminophenyl)methyl]-2-isobutyl-3-methylisoxazolin-5-one (350 mg, 1.30 mmol), and the mixture was stirred at the same temperature for an hour. Water was poured into the reaction mixture, followed by extraction with chloroform. The extraction liquid was washed with saturated brine, dried over anhydrous sodium sulfate and then concentrated under reduced pressure. The concentrate was purified by silica gel column chromatography (eluent: ethyl acetate/n-hexane=1/3), and 1,1,1-trifluoro-N-[2-[(2-isobutyl-3-methyl-5-oxoisoxazol-4-yl)methyl]phenyl]methanesulfonamide (amount of 230 mg, yield of 59%) as a yellow oil and 1,1,1-trifluoro-N-[2-[(2-isobutyl-3-methyl-5-oxoisoxazol-4-yl)methyl]phenyl]-N-(trifluoromethylsulfonyl)methanesulfonamide (amount of 180 mg, yield of 34%) as a yellow solid were thus obtained.

Synthesis Example 2

Synthesis of 1,1,1-trifluoro-N-[2-[(3-methyl-5-oxo-2-sec-butyl-isoxazol-4-yl)methyl]phenyl]methanesulfonamide (1-102) and 1,1,1-trifluoro-N-[2-[(3-methyl-5-oxo-2-sec-butyl-isoxazol-4-yl)methyl]phenyl]-N-(trifluoromethyl sulfonyl)methanesulfonamide (1-964

Triethylamine (86.0 mg, 0.850 mmol) and trifluoromethanesulfonic anhydride (220 mg, 0.770 mmol) were added at 0° C. to a chloroform solution (3 ml) of 4-[(2-aminophenyl)methyl]-3-methyl-2-sec-butyl-isoxazolin-5-one (100 mg, 0.380 mmol), and the mixture was stirred at the same temperature for an hour. Water was poured into the reaction mixture, followed by extraction with chloroform. The extraction liquid was washed with saturated brine, dried over anhydrous sodium sulfate and then concentrated under reduced pressure. The concentrate was purified by silica gel column chromatography (eluent: ethyl acetate/n-hexane=1/3), and 1,1,1-trifluoro-N-[2-[(3-methyl-5-oxo-2-sec-butyl-isoxazol-4-yl)methyl]phenyl]methanesulfonamide (amount of 80.0 mg, yield of 50%) as a yellow oil and 1,1,1-trifluoro-N-[2-[(3-methyl-5-oxo-2-sec-butyl-isoxazol-4-yl)methyl]phenyl]-N-(trifluoromethylsulfonyl)methanesulfonamide (amount of 20.0 mg, yield of 10%) as a yellow gum were thus obtained.

Synthesis Example 3

Synthesis of 1,1,1-trifluoro-N-[2-[[2-(2-methoxy-1-methyl-ethyl)-3-methyl-5-oxo-isoxazol-4-yl]methyl]phenyl]methanesulfonamide (1-149) and 1,1,1-trifluoro-N-[2-[[2-(2-methoxy-1-methyl-ethyl)-3-methyl-5-oxo-isoxazol-4-yl]methyl]phenyl]-N-(trifluoromethyl sulfonyl)methanesulfonamide (1-997

The same reaction and treatment as those in Synthesis Example 2 were conducted using 4-[(2-aminophenyl)methyl]-2-(2-methoxy-1-methyl-ethyl)-3-methyl-isoxazolin-5-one instead of 4-[(2-aminophenyl)methyl]-3-methyl-2-sec-butyl-isoxazolin-5-one, and 1,1,1-trifluoro-N-[2-[[2-(2-methoxy-1-methyl-ethyl)-3-methyl-5-oxo-isoxazol-4-yl]methyl]phenyl]methanesulfonamide (yield of 47%) as a white solid and 1,1,1-trifluoro-N-[2-[[2-(2-methoxy-1-methyl-ethyl)-3-methyl-5-oxo-isoxazol-4-yl]methyl]phenyl]-N-(trifluoromethylsulfonyl)methanesulfonamide (yield of 14%) as a yellow solid were thus obtained.

Synthesis Example 4

Synthesis of N-[2-[(2-isobutyl-3-methyl-5-oxoisoxazol-4-yl)methyl]phenyl]-N-(trifluoromethyl sulfonyl)acetamide (1-297

Triethylamine (71.0 mg, 0.700 mmol) and acetyl chloride (51.0 mg, 0.640 mmol) were added at 0° C. to a chloroform solution (3 ml) of 1,1,1-trifluoro-N-[2-[(2-isobutyl-3-methyl-5-oxoisoxazol-4-yl)methyl]phenyl]methanesulfonamide (230 mg, 0.590 mmol), and the mixture was stirred at the same temperature for an hour. Water was poured into the reaction mixture, followed by extraction with chloroform. The extraction liquid was washed with saturated brine, dried over anhydrous sodium sulfate and then concentrated under reduced pressure. The concentrate was purified by silica gel column chromatography (eluent: ethyl acetate/n-hexane=1/1), and the title compound (amount of 240 mg, yield of 94%) as a yellow oil was thus obtained.

Synthesis Example 5

Synthesis of methyl N-[2-[(3-methyl-5-oxo-2-sec-butyl-isoxazol-4-yl)methyl]phenyl]-N-(trifluoromethyl sulfonyl)carbamate (1-577

Sodium hydrogen carbonate (161 mg, 1.91 mmol) and methyl chloroformate (181 mg, 1.91 mmol) were added to an acetonitrile solution (3 ml) of 1,1,1-trifluoro-N-[2-[(3-methyl-5-oxo-2-sec-butyl-isoxazol-4-yl)methyl]phenyl] methanesulfonamide (250 mg, 0.637 mmol), and the mixture was heated under reflux for an hour. Water was poured into the reaction mixture, followed by extraction with ethyl acetate. The extraction liquid was washed with saturated brine, dried over anhydrous sodium sulfate and then concentrated under reduced pressure. The concentrate was purified by silica gel column chromatography (eluent: ethyl acetate/n-hexane=1/3), and the title compound (amount of 201 mg, yield of 70%) as a yellow solid was thus obtained.

Synthesis Example 6

Synthesis of N-[2-[(2-tert-butyl-3-methyl-5-oxo-isoxazol-4-yl)]methyl]phenyl]-1,1,1-trifluoromethanesulfonamide (1-101) and N-[2-[(2-tert-butyl-3-methyl-5-oxo-isoxazol-4-yl)methyl]phenyl]-1,1,1-trifluoro-N-(trifluoromethylsulfonyl) methanesulfonamide (1-963

Triethylamine (1.60 g, 16.0 mmol) and trifluoromethanesulfonic anhydride (4.10 g, 15.0 mmol) were added at 0° C. to a chloroform solution (100 ml) of 4-[(2-aminophenyl)methyl]-2-tert-butyl-3-methyl-isoxazolin-5-one (2.70 g, 10.0 mmol), and the mixture was stirred at the same temperature for an hour. Water was poured into the reaction mixture, followed by extraction with chloroform. The extraction liquid was washed with saturated brine, dried over anhydrous sodium sulfate and then concentrated under reduced pressure. The concentrate was purified by silica gel column chromatography (eluent: ethyl acetate/n-hexane=1/3), and N-[2-[(2-tert-butyl-3-methyl5-oxo-isoxazol-4-yl)]methyl]phenyl]-1,1,1-trifluoro-methanesulfonamide (amount of 1.40 g, yield of 34%) as a yellow oil and N-[2-[(2-tert-butyl-3-methyl-5-oxo-isoxazol-4-yl)methyl] phenyl]-1,1,1-trifluoro-N-(trifluoromethylsulfonyl)methanesulfonamide (amount of 0.95 g, yield of 17%) as a yellow amorphous material were thus obtained.

The $^1$HNMR spectrum (CDCl$_3$) σ (ppm) values, the melting points (° C.) and the like of the compounds according to the invention produced based on the above Synthesis Examples and the above production methods are shown in Table 2. The $^1$HNMR data were measured by JNM-ECS400 spectrometer (manufactured by JEOL Ltd.). The compound numbers in Table 2 are the same as those in Table 1 above.

TABLE 2

| No. | Property (mp.° C.) | Form | $^1$HNMR spectrum σ ppm: |
|---|---|---|---|
| 1-2 | | amorphous | 9.65 (1H, brs), 7.57 (1H, d, J = 7.8 Hz), around7.24 (1H, m), 7.17-7.16 (2H, m), 4.58 (2H, s), 3.77 (1H, m), 3.66 (2H, s), 2.28 (3H, s), 1.84-1.77 (1H, m), 1.65-1.58 (1H, m), 1.19 (3H, d, J = 6.6 Hz), 0.90 (3H, t, J = 7.3 Hz) |
| 1-3 | | gum | |
| 1-4 | | amorphous | |
| 1-5 | | amorphous | |
| 1-6 | | amorphous | |
| 1-7 | | gum | |
| 1-17 | | gum | 9.20 (1H, brs), 7.35 (1H, d, J = 7.8 Hz), 7.23 (1H, t, J = 7.8 Hz), 7.17 (1H, d, J = 7.8 Hz), 7.07 (1H, t, J = 7.8 Hz), 6.12 (1H, t, J = 55.2 Hz 9, 3.82-3.76 (1H, m), 3.63 (1H, dd, J = 15.1, 3.2 Hz), 3.90 (1H, d, J = 15.1 Hz), 1.85-1.75 (1H, m), 1.67-1.56 (1H, m), 1.20 (3H, dd, J = 6.4, 1.0 Hz), 0.90 (3H, td, J = 7.3, 2.3 Hz) |
| 1-19 | | amorphous | |
| 1-20 | | amorphous | |
| 1-28 | | oil | 10.7 (1H, br.s), 7.46 (1H, dd, J = 8.7, 5.0 Hz), 6.96 (1H, td, J = 8.4, 2.9 Hz), 6.84 (1H, dd, J = 8.5, 3.0 Hz), 3.54 (2H, s), 3.45 (2H, d, J = 6.9 Hz), 2.32 (3H, s), 2.20-2.12 (1H, m), 0.94 (6H, d, J = 6.9 Hz). |
| 1-29 | | oil | |
| 1-31 | | oil | |
| 1-32 | 65.1 | solid | |
| 1-33 | 125 | solid | |
| 1-37 | | gum | 10.70 (1H, brs), 7.50 (1H, d, J = 2.0 Hz), 7.16 (1H, dd, J = 8.4, 2.0 Hz), 7.05 (1H, d, J = 8.4 Hz), 4.15-4.04 (1H, m), 3.31 (2H, s), 2.29 (3H, s), 1.25 (6H, d, J = 6.4 Hz). |
| 1-41 | | gum | 10.87 (1H, brs), 7.42 (1H, d, J = 8.8 Hz), 7.22 (1H, dd, J = 8.8, 2.4 Hz), 7.10 (1H, d, J = 2.4 Hz), 4.14-4.06 (1H, m), 3.51 (2H, s), 2.31 (3H, s), 1.27 (6H, d, J = 6.8 Hz). |
| 1-46 | | gum | 11.10 (1H, brs), 7.43 (1H, dd, J = 7.6, 1.2 Hz), 7.30 (1H, dd, J = 7.6, 1.2 Hz), 7.21 (1H, dd, J = 7.6, 7.6 Hz), 4.11 (1H, quint, J = 6.4 Hz), 3.71 (2H, s), 2.38 (3H, s), 1.26 (6H, d, J = 6.4 Hz). |
| 1-47 | | gum | |
| 1-63 | | gum | 10.91 (1H, brs), 7.48 (1H, d, J = 8.4 Hz), 7.28-7.22 (1H, m), 7.22-7.16 (1H, m), 7.14 (1H, dd, J = 7.2, 1.2 Hz), 4.07 (1H, quint, J = 6.8 Hz), 3.56 (2H, s), 2.67 (2H, q, J = 8.0 Hz), 1.32-1.23 (9H, m). |
| 1-68 | | gum | 10.93 (1H, brs), 7.48 (1H, dd, J = 7.6, 1.2 Hz), 7.28-7.22 (1H, m), 7.21-7.14 (2H, m), 4.16 (1H, quint, J = 6.4 Hz), 3.61 (2H, s), 3.27 (1H, quint, J = 7.2 Hz), 1.40 (6H, d, J = 7.2 Hz), 1.27 (6H, d, J = 6.4 Hz). |
| 1-69 | | gum | |
| 1-78 | | gum | |
| 1-81 | | oil | 9.92 (1H, br.s), 7.51 (1H, dd, J = 7.8, 1.4 Hz), 7.33-7.23 (3H, m), 3.79 (2H, s), 3.50 (2H, d, J = 7.3 Hz), 2.26-2.14 (1H, m), 2.17 (3H, s), 0.97 (6H, d, J = 6.9 Hz). |

TABLE 2-continued

| No. | Property (mp.° C.) | Form | ¹HNMR spectrum σ ppm: |
|---|---|---|---|
| 1-83 | | gum | 10.79 (1H, brs), 7.52-7.48 (1H, m), 7.28-7.19 (3H, m), 4.44 (1H, quint, 6.4 Hz), 3.67 (2H, s), 1.68 (2H, m), 1.25 (6H, d, J = 6.4 Hz), 0.96-0.92 (2H, m) |
| 1-84 | 105 | solid | |
| 1-96 | 135-137 | solid | 10.60 (2H, brs), 7.48 (1H, dd, J = 8.4, 1.6 Hz), 7.29-7.24 (1H, m), 7.21 (1H, ddd, J = 7.4, 7.4, 1.6 Hz), 7.17 (1H, dd, J = 8.4, 2.4 Hz), 3.56 (2H, s), 2.36 (3H, s). |
| 1-97 | | oil | |
| 1-98 | | gum | |
| 1-100 | | gum | |
| 1-101 | | oil | 10.9 (1H, br.s), 7.50-7.47 (1H, m), 7.27-7.23 (1H, m), 7.22-7.18 (1H, m), 7.16-7.14 (1H, m), 3.56 (2H, s), 2.43 (3H, s), 1.42 (9H, s). |
| 1-102 | | oil | 7.50-7.48 (1H, d, J = 7.8 Hz), 7.28-7.15 (3H, m), 3.82 (1H, m), 3.57 (2H, s), 2.32 (3H, s), 1.85-1.74 (1H, m), 1.67-1.56 (1H, m), 1.20 (3H, d, J = 6.9 Hz), 0.89 (3H, t, J = 7.3 Hz) |
| 1-103 | | oil | |
| 1-105 | | oil | 10.9 (1H, br.s), 7.50 (1H, d, J = 8.2 Hz), 7.28-7.24 (1H, m), 7.21 (1H, td, J = 7.3, 1.4 Hz), , 7.15 (1H, dd, J = 7.8, 1.8 Hz), 3.56 (2H, s), 3.43 (2H, d, J = 6.9 Hz), 2.31 (3H, s), 2.21-2.10 (1H, m), 0.94 (6H, d, J = 6.9 Hz). |
| 1-106 | 146-148 | solid | |
| 1-109 | | gum | |
| 1-110 | | oil | |
| 1-112 | | oil | |
| 1-113 | | gum | |
| 1-115 | 68.1-72.4 | solid | |
| 1-116 | | gum | |
| 1-120 | | oil | |
| 1-124 | 68 | solid | |
| 1-130 | | oil | |
| 1-133 | | oil | |
| 1-134 | | oil | 10.0 (1H, br.s), 7.50 (1H, d, J = 7.8 Hz), 7.31-7.27 (1H, m), 7.26-7.22 (1H, m), 7.16-7.14 (1H, m), 4.20 (2H, d, J = 7.8 Hz), 3.61 (2H, s), 2.38 (3H, s). |
| 1-135 | | oil | 7.50-7.48 (1H, d, J = 6.9 Hz), 7.29-7.14 (3H, s), 5.77-5.70 (1H, m), 5.30-5.25 (2H, m), 4.24 (1H, brd, J = 6.0 Hz), 3.60 (2H, s), 2.17 (3H, s) |
| 1-136 | | oil | |
| 1-137 | | oil | |
| 1-138 | | oil | 10.2 (1H, br.s), 7.49 (1H, dd, J = 7.8, 1.4 Hz), 7.28 (1H, td, J = 7.3, 1.8 Hz), 7.23 (1H, td, J = 7.4, 1.5 Hz), 7.17 (1H, dd, J = 7.6, 1.6 Hz), 4.36 (2H, d, J = 2.3 Hz), 3.62 (2H, s), 2.34 (3H, s), 2.25 (1H, d, J = 2.3 Hz). |
| 1-142 | | oil | 10.8 (1H, br.s), 7.49 (1H, dd, J = 7.8, 0.9 Hz), 7.28-7.13 (3H, m), 3.77-3.64 (1H, m), 3.56 (2H, s), 2.36 (3H, s), 1.88-1.84 (2H, m), 1.74-1.64 (4H, m), 1.29-1.24 (2H, m). |
| 1-143 | | oil | 10.8 (1H, br.s), 7.50 (1H, d, J = 7.8 Hz), 7.27 (1H, td, J = 7.3, 1.4 Hz), 7.21 (1H, td, J = 7.3, 1.4 Hz), 7.16 (1H, dd, J = 7.6, 1.6 Hz), 3.58 (2H, s), 3.52 (2H, d, J = 6.9 Hz), 2.33 (3H, s), 1.05-0.95 (1H, m), 0.65-0.53 (2H, m), 0.34-0.23 (2H, m). |
| 1-144 | | oil | |
| 1-145 | | oil | |
| 1-146 | | gum | |
| 1-148 | 109.0-112.5 | solid | 10.72 (1H, brs), 7.47 (1H, dd, J = 7.6, 1.2 Hz), 7.26-7.21 (1H, m), 7.19 (1H, ddd, J = 7.6, 7.6, 1.6 Hz), 7.16-7.13 (1H, m), 3.82 (2H, dd, J = 4.8, 4.8 Hz), 3.55 (2H, s), 3.48 (2H, dd, J = 4.8, 4.8 Hz), 3.15 (3H, s), 2.32 (3H, s). |
| 1-149 | 107-109 | solid | 10.8 (1H, br.s), 7.48-7.46 (1H, m), 7.26-7.15 (3H, m), 4.17-4.08 (1H, m), 3.56 (2H, s), 3.43-3.32 (2H, m), 3.11 (3H, s), 2.33 (3H, s), 1.28-1.26 (3H, m). |
| 1-155 | | oil | 10.58 (1H, brs), 7.48-7.41 (1H, m), 7.37-7.31 (3H, m), 3.85 (2H, d, J = 4.8 Hz), 3.71 (2H, s), 3.59 (2H, dd, J = 4.0, 4.0 Hz), 3.53-3.44 (1H, m), 2.02 (3H, s), 1.04 (6H, d, J = 6.0 Hz). |
| 1-156 | | oil | 7.51-7.40 (1H, m), 7.37-7.31 (1H, m), 7.27-7.21 (1H, m), 7.19-7.11 (1H, m), 3.89-3.85 (2H, m), 3.71 (1H, s), 3.60 (1H, dd, J = 4.0, 4.0 Hz), 3.54 (1H, s), 3.49 (1H, dd, J = 4.0, 4.0 Hz), 3.12 (1H, d, J = 6.8 Hz), 3.00 (1H, d, J = 6.8 Hz), 2.15 (3H, s), 1.64-1.54 (1H, m), 0.81 (3H, d, J = 6.8 Hz), 0.72 (3H, d, J = 6.8 Hz). |
| 1-162 | | oil | 10.6 (1H, br.s), 7.49 (1H, dd, J = 8.0, 1.1 Hz), 7.27 (1H, dd, J = 7.3, 1.8 Hz), 7.21 (1H, td, J = 7.6, 1.5 Hz), 7.16 (1H, dd, J = 7.8, 1.8 Hz), 3.83 (2H, t, J = 6.6 Hz), 3.58 (2H, s), 2.75 (2H, t, J = 6.6 Hz), 2.37 (3H, s), 2.05 (3H, s). |
| 1-166 | | oil | |
| 1-167 | | oil | |
| 1-174 | | oil | 10.6 (1H, br.s), 7.54-7.41 (4H, m), 7.32-7.19 (5H, m), 3.67 (2H, s), 2.32 (3H, s). |
| 1-175 | | oil | |
| 1-176 | | oil | |
| 1-177 | | amorphous | |
| 1-180 | | gum | |
| 1-181 | | oil | |
| 1-182 | | gum | |
| 1-183 | | gum | |
| 1-186 | | gum | 10.4 (1H, br.s), 7.48 (1H, dd, J = 8.0, 1.1 Hz), 7.31 (2H, dt, J = 8.7, 2.2 Hz), 7.27-7.25 (1H, m), 7.21 (1H, td, J = 7.3, 1.4 Hz), 7.16 (2H, dt, J = 8.7, 2.2 Hz), 7.10 (3H, dd, J = 7.6, 1.6 Hz), 4.73 (2H, s), 3.54 (2H, s), 2.35 (3H, s). |
| 1-187 | 110-115 | solid | |
| 1-189 | | oil | |

TABLE 2-continued

| No. | Property (mp.° C.) | Form | ¹HNMR spectrum σ ppm: |
|---|---|---|---|
| 1-191 | 88-89 | solid | 10.58 (1H, brs), 7.46 (1H, dd, J = 8.0, 1.2 Hz), 7.27-7.22 (1H, m), 7.18 (1H, ddd, J = 7.6, 7.6, 1.2 Hz), 7.13-7.06 (5H, m), 4.74 (2H, s), 3.51 (2H, s), 2.33 (3H, s), 2.31 (3H, s). |
| 1-192 | | gum | |
| 1-193 | | gum | |
| 1-194 | | gum | 10.28 (1H, brs), 7.57 (2H, d, J = 8.4 Hz), 7.45 (1H, dd, J = 8.4, 1.6 Hz), 7.33 (2H, d, J = 8.4 Hz), 7.27-7.22 (1H, m), 7.19 (1H, ddd, J = 7.6, 7.6, 1.6 Hz), 7.10 (1H, dd, J = 7.6, 1.6 Hz), 4.79 (2H, s), 3.53 (2H, s), 2.35 (3H, s). |
| 1-195 | | oil | 10.57 (1H, brs), 7.46 (1H, dd, J = 8.0, 1.2 Hz), 7.26-7.22 (1H, m), 7.18 (1H, ddd, J = 8.0, 8.0, 1.2 Hz), 7.12 (2H, d, J = 8.8 Hz), 7.09 (1H, dd, J = 1.6, 7.6 Hz), 6.83 (2H, d, J = 8.8 Hz), 4.71 (2H, s), 3.78 (3H, s), 3.51 (2H, s), 2.32 (3H, s). |
| 1-198 | | gum | 10.28 (1H, brs), 7.61 (2H, d, J = 8.0 Hz), 7.47 (1H, dd, J = 7.6, 0.8 Hz), 7.29-7.23 (3H, m), 7.19 (1H, ddd, J = 7.2, 7.2, 1.2 Hz), 7.10 (1H, dd, J = 7.2, 1.2 Hz), 4.77 (2H, s), 3.55 (2H, s), 2.36 (3H, s). |
| 1-199 | | oil | |
| 1-200 | | gum | |
| 1-201 | | gum | |
| 1-202 | | oil | |
| 1-203 | | gum | 10.6 (1H, br.s), 7.47-7.44 (1H, m), 7.34-7.29 (3H, m), 7.26-7.21 (3H, m), 7.18-7.14 (1H, m), 7.07-7.05 (1H, m), 5.03 (1H, q, J = 7.0 Hz), 3.50 (2H, q, J = 14.7 Hz), 2.28 (3H, s), 1.70 (3H, d, J = 6.9 Hz). |
| 1-204 | | oil | 10.52 (1H, brs), 7.46 (1H, dd, J = 7.6, 0.8 Hz), 7.26-7.20 (3H, m), 7.16 (1H, ddd, J = 7.2, 7.2, 1.2 Hz), 7.04 (1H, dd, J = 7.2, 1.2 Hz), 6.99 (2H, dd, J = 8.8, 8.8 Hz), 4.98 (1H, dd, J = 6.8, 6.8 Hz), 3.53 (1H, d, J = 15.2 Hz), 3.46 (1H, d, J = 15.2 Hz), 2.29 (3H, s), 1.67 (3H, d, J = 6.8 Hz). |
| 1-205 | | oil | |
| 1-206 | | oil | |
| 1-207 | | oil | |
| 1-208 | | oil | |
| 1-209 | | gum | 10.48 (1H, brs), 7.46 (1H, dd, J = 8.0, 0.8 Hz), 7.30-7.26 (2H, m), 7.25-7.21 (1H, m), 7.18-7.14 (3H, m), 7.05 (1H, dd, J = 7.6, 1.6 Hz), 5.01 (1H, q, J = 6.8 Hz), 3.53 (1H, d, J = 15.2 Hz), 3.47 (1H, d, J = 15.2 Hz), 2.29 (3H, s), 1.66 (3H, d, J = 6.8 Hz). |
| 1-211 | | oil | 10.40 (1H, brs), 7.44 (1H, dd, J = 8.0, 1.2 Hz), 7.32-7.26 (3H, m), 7.22-7.16 (3H, m), 7.12 (1H, ddd, J = 7.2, 7.2, 0.8 Hz), 7.02 (1H, dd, J = 8.0, 1.6 Hz), 4.65 (1H, dd, J = 8.0, 8.0 Hz), 3.52 (1H, d, J = 15.2 Hz), 3.41 (1H, d, J = 15.2 Hz), 2.31-2.23 (4H, m), 2.08-1.96 (1H, m), 0.95 (3H, t, J = 7.2 Hz). |
| 1-212 | | gum | |
| 1-213 | | gum | |
| 1-214 | | gum | |
| 1-215 | | gum | |
| 1-216 | | oil | 10.58 (1H, brs), 7.49-7.43 (1H, m), 7.37-7.31 (2H, m), 7.30-7.25 (4H, m), 7.18-7.14 (2H, m), 3.88 (2H, dd, J = 6.8, 6.8 Hz), 3.66 (2H, s), 3.01 (2H, dd, J = 6.8, 6.8 Hz), 2.15 (3H, s). |
| 1-218 | | gum | |
| 1-219 | | gum | |
| 1-220 | | oil | |
| 1-221 | | gum | |
| 1-222 | | gum | 10.61 (1H, brs), 7.51-7.46 (1H, m), 7.29-7.03 (7H, m), 5.45 (1H, dd, J = 8.5, 5.3 Hz), 3.59 (2H, s), 3.16-3.08 (1H, m), 2.92-2.85 (1H, m), 2.41-2.314 (1H, m), 2.17-2.07 (1H, m), 2.03 (3H, s) |
| 1-224 | | gum | 10.76 (1H, brs), 7.51-7.48 (1H, m), 7.29-7.06 (7H, m), 5.14 (1H, m), 3.60 (2H, s), 2.88-2.71 (2H, m), 2.33 (3H, s), 2.02-1.87 (4H, m), 1.81-1.72 (2H, m) |
| 1-229 | | oil | |
| 1-230 | | oil | 10.66 (1H, brs), 7.42 (1H, dd, J = 8.0, 1.2 Hz), 7.27-7.22 (1H, m), 7.20-7.18 (1H, m), 7.17-7.15 (1H, m), 4.09-4.03 (1H, m), 3.80-3.66 (4H, m), 3.60 (1H, d, J = 15.2 Hz), 3.53 (1H, d, J = 15.2 Hz), 2.73 (3H, s), 2.06-1.98 (1H, m), 1.91-1.82 (2H, m), 1.61-1.54 (1H, m). |
| 1-231 | | oil | |
| 1-232 | | oil | 10.4 (1H, br.s), 7.48-7.46 (1H, m), 7.29-7.27 (1H, m), 7.26-7.16 (3H, m), 7.10-7.08 (1H, m), 6.94-6.92 (1H, m), 4.79 (2H, s), 3.52 (2H, s), 2.33 (3H, s). |
| 1-235 | | oil | |
| 1-237 | | oil | 10.57 (1H, brs), 7.47 (1H, d, J = 6.9 Hz), 7.27-7.12 (5H, m), 6.95 (1H, t, J = 7.3 Hz), 6.68 (1H, brd, J = 7.8 Hz), 4.13-4.09 (4H, m), 3.55 (2H, s), 2.24 (3H, s) |
| 1-238 | | oil | 7.49 (1H, d, J = 8.2 Hz), 7.31-7.27 (3H, m), 7.22 (1H, t, J = 8.2 Hz), around7.11 (4H, m), 4.34 (2H, s), 3.87 (2H, t, J = 4.8 Hz), 3.57 (2H, t, J = 4.8 Hz), 3.55 (2H, s), 2.30 (3H, s) |
| 1-242 | | oil | 9.77 (1H, br.s), 7.51 (1H, d, J = 7.8 Hz), 7.31 (1H, td, J = 7.6, 1.8 Hz), 7.28-7.23 (1H, m), 7.19 (1H, dd, J = 7.8, 1.8 Hz), 3.64 (2H, s), 3.18-3.15 (1H, m), 2.75 (3H, s), 1.22 (6H, d, J = 6.9 Hz). |
| 1-248 | | oil | |
| 1-249 | | oil | 9.95 (1H, br.s), 7.50 (1H, dd, J = 8.0, 1.6 Hz), 7.35-7.26 (2H, m), 7.18 (1H, dd, J = 7.6, 1.6 Hz), 3.68 (2H, s), 3.22 (3H, s), 2.60 (3H, s). |
| 1-251 | | oil | |
| 1-254 | | amorphous | 9.98 (1H, br.s), 7.61 (2H, d, J = 8.4 Hz), 7.40 (1H, dd, J = 8.0, 1.1 Hz), 7.30-7.28 (1H, m), 7.22-7.18 (1H, m), 7.20 (1H, d, J=8.4 Hz), 6.96 (1H, dd, J = 7.6,1.6 Hz), 3.46 (2H, s), 2.60 (3H, s), 2.35 (3H, s). |
| 1-256 | | gum | |

TABLE 2-continued

| No. | Property (mp.° C.) | Form | ¹HNMR spectrum σ ppm: |
|---|---|---|---|
| 1-260 | | gum | |
| 1-263 | | oil | |
| 1-264 | | gum | 7.34 (1H, dd, J = 7.3, 1.8 Hz), 7.29-7.19 (3H, m), 3.89 (2H, q, J = 7.2 Hz), 3.71 (2H, s), 3.47 (2H, d, J = 7.3 Hz), 2.09 (2H, s), 1.90-1.84 (1H, m), 1.46-1.36 (4H, m), 1.23 (3H, t, J = 7.3 Hz), 0.92 (6H, td, J = 7.3, 1.4 Hz). |
| 1-270 | | oil | 7.36-7.32 (2H, m), 7.28-7.24 (1H, m), 7.21-7.19 (1H, m), 5.20 (1H, d, J = 10.1 Hz), 4.97 (1H, d, J = 10.1 Hz), 3.71 (2H, s), 3.44 (3H, s), 3.39 (2H, d, J = 7.3 Hz), 2.22-2.16 (1H, m), 2.09 (3H, s), 0.98 (6H, dd, J = 6.9, 1.8 Hz). |
| 1-271 | | oil | |
| 1-278 | | oil | 7.37-7.29 (2H, m), 7.28-7.24 (2H, m), 7.17-7.14 (3H, m), 7.12-7.10 (1H, m), 6.99-6.96 (1H, m), 5.06 (1H, d, J = 14.2 Hz), 4.82 (1H, d, J = 14.2 Hz), 3.53 (1H, d, J = 16.9 Hz), 3.35 (2H, d, J = 7.3 Hz), 3.08 (1H, d, J = 16.9 Hz), 2.22-2.16 (1H, m), 1.93 (3H, s), 0.96 (6H, dd, J = 6.9 Hz). |
| 1-279 | | oil | |
| 1-293 | | oil | |
| 1-294 | 92-94 | solid | 7.45 (1H, t, J = 7.8 Hz), 7.36 (1H, t, J = 7.8 Hz), 7.32 (1H, d, _J = 7.8 Hz), 7.21 (1H, d, J = 7.8 Hz), 3.81 (1H, m), 3.69 (1H, d, J = 18.8 Hz), 3.60 (1H, d, J = 18.8 Hz), 2.16 (3H, s), 1.92-1.82 (1H, m), 1.72-1.60 (1H, m), 1.28-1.21 (3H, m), 0.98 (3H, dt, J = 9.6, 7.3 Hz) |
| 1-295 | | oil | |
| 1-297 | | oil | 7.46-7.42 (1H, m), 7.37-7.33 (2H, m), 7.20 (1H, d, J = 8.2 Hz), 3.63 (2H, dd, J = 41.2, 16.9 Hz), 3.41 (2H, d, J = 7.3 Hz), 2.28-2.17 (1H, m), 2.15 (3H, s), 2.14 (3H, s), 0.99 (6H, dd, J = 6.6, 3.4 Hz). |
| 1-298 | | oil | |
| 1-299 | | oil | |
| 1-300 | | oil | |
| 1-304 | | oil | 7.46-7.40 (1H, m), 7.37-7.32 (1H, m), 7.31-7.28 (1H, m), 7.22-7.20 (1H, m), 4.20-4.09 (1H, m), 3.70-3.54 (3H, m), 3.39-3.36 (1H, m), 3.32 (3H, d, J = 19.7 Hz), 2.18-2.16 (6H, m), 1.34-1.32 (3H, m). |
| 1-305 | | gum | |
| 1-306 | | oil | |
| 1-307 | | oil | |
| 1-308 | | oil | |
| 1-310 | | gum | |
| 1-315 | | | |
| 1-316 | | oil | |
| 1-318 | | oil | |
| 1-319 | 122-124 | solid | 7.39 (1H, ddd, J = 7.2, 7.2, 0.8 Hz), 7.34-7.25 (2H, m), 7.18 (1H, d, J = 7.2 Hz), 4.18-4.07 (1H, m), 3.65-3.50 (3H, m), 3.39-3.33 (1H, m), 3.32 (1.5H, s), 3.27 (1.5H, s), 2.50-2.30 (1H, m), 2.27-2.18 (1H, m), 2.16 (1.5H, s), 2.14 (1.5H, s), 1.31 (3H, d, J = 6.8 Hz), 1.08 (3H, t, J = 6.8 Hz). |
| 1-320 | | gum | |
| 1-321 | | oil | |
| 1-329 | | | |
| 1-330 | | oil | |
| 1-331 | | oil | |
| 1-333 | | oil | |
| 1-334 | | oil | |
| 1-335 | | oil | 7.43-7.37 (1H, m), 7.35-7.30 (1H, m), 7.29-7.25 (1H, m), 7.23-7.19 (1H, m), 4.18-4.07 (1H, m), 3.66-3.53 (3H, m), 3.38-3.34 (1H, m), 3.32 (1.5H, s), 3.27 (1.5H, s), 2.58-2.45 (1H, m), 2.12 (1.5H, s), 2.10 (1.5H, s), 1.33-1.27 (3H, m), 1.22-1.16 (3H, m), 1.08-1.03 (3H, m). |
| 1-336 | | gum | |
| 1-337 | | oil | |
| 1-351 | 97-98 | solid | 7.43 (1H, ddd, J = 7.6, 7.6, 1.2 Hz), 7.34 (1H, ddd, J = 7.6, 7.6, 1.6 Hz), 7.21 (1H, d, J = 7.6 Hz), 7.17 (1H, d, J = 7.6 Hz), 3.64 (1H, d, J = 17.6 Hz), 3.55 (1H, d, J = 17.6 Hz), 2.31-2.24 (1H, m), 2.23 (3H, s), 2.22-2.02 (2H, m), 1.45 (9H, s), 0.91 (3H, d, J = 6.4 Hz), 0.87 (3H, d, J = 6.4 Hz). |
| 1-352 | 95-97 | solid | 7.44 (1H, t, J = 7.6 Hz), 7.34 (1H, t, J = 7.6 Hz), 7.28 (1H, dd, J = 8.2, 5.0 Hz), 7.16 (1H, d, J = 8.2 Hz), 3.83-3.74 (1H, m), 3.65 (1H, d, J = 16.9 Hz), 3.57 (1H, d, J = 16.9 Hz), 2.28-2.02 (2H, m), 2.13 (3H, s), 1.92-1.79 (1H, m), 1.70-1.58 (2H, m), 1.29-0.85 (12H, m) |
| 1-353 | | oil | |
| 1-354 | | oil | 7.47-7.43 (1H, m), 7.37-7.32 (2H, m), 7.18 (1H, d, J=7.8 Hz), 3.62 (2H, q, J=16.5 Hz), 3.41 (2H, d, J=7.3 Hz), 2.25-2.04 (4H, m), 2.13 (3H, s), 0.99 (6H, dd, J=6.9, 2.7 Hz), 0.90 (6H, dd, J=13.7, 6.4 Hz). |
| 1-355 | | oil | |
| 1-356 | | oil | |
| 1-357 | 80-82 | solid | 7.45-7.37 (1H, m), 7.35-7.25 (2H, m), 7.17 (1H, d, J = 8.0 Hz), 4.18-4.07 (1H, m), 3.67-3.51 (3H, m), 3.40-3.27 (4H, m), 2.34-2.24 (1H, m), 2.21-2.01 (5H, m), 1.32 (3H, d, J = 10.0 Hz), 0.93-0.90 (3H, m), 0.89-0.86 (3H, m). |
| 1-358 | | gum | |
| 1-359 | | oil | |
| 1-403 | | oil | |
| 1-404 | | oil | 7.44 (1H, t, J = 7.3 Hz), 7.39-7.33- (2H, m), around7.24 (1H, m), 3.78 (1H, d, J = 16.9 Hz), 3.78 (1H, m), 3.64 (1H, d, J = 16.9 Hz), 2.15 (3H, s), 1.90-1.78 (1H, m), |

TABLE 2-continued

| No. | Property (mp.° C.) | Form | ¹HNMR spectrum σ ppm: |
|---|---|---|---|
| | | | 1.69-1.58 (2H, m), 1.47-1.36 (1H, m), around1.24 (1H, m), 1.21 (3H, dd, J = 6.9, 1.4 Hz), 1.11-1.03 (1H, m), 0.95 (3H, dt, J = 7.3, 1.8 Hz) |
| 1-405 | | oil | |
| 1-407 | | oil | |
| 1-408 | | oil | |
| 1-412 | | oil | |
| 1-413 | | gum | |
| 1-414 | | oil | |
| 1-416 | | oil | |
| 1-431 | | gum | |
| 1-432 | | oil | 7.46 (1H, t, J = 7.6 Hz), 7.36-7.29 (2H, m), 7.21 (1H, d, J = 7.6 Hz), 3.79 (1H, m), 3.58 (2H, s), 2.27-2.16 (1H, m), 2.12 (3H, s), 1.95-1.57 (8H, m), 1.46-1.37 (1H, m), 1.25 (3H, dd, J = 8.0, 6.6 Hz), around1.18 (2H, m), 0.97 (3H, dt, J = 7.3, 6.4 Hz), around0.97 (1H, m) |
| 1-434 | | gum | |
| 1-444 | | gum | 7.48 (1H, t, J = 7.8 Hz), 7.36 (1H, t, J = 7.8 Hz), 7.31 (1H, d, J = 7.8 Hz), 7.22 (1H, d, J = 7.8 Hz), 4.12 (1H, dd, J = 16.9, 3.0 Hz), 3.81 (1H, m), 3.69 (1H, d, J = 17.9 Hz), 3.57 (1H, d, J = 17.9 Hz), 3.40 (2H, s), 2.23 (3H, s), 1.92-1.81 (1H, m), 1.70-1.59 (1H, m), 1.24 (3H, dd, J = 18.5, 6.6 Hz), 0.98 (3H, dt, J = 11.0, 7.3 hz) |
| 1-472 | | gum | |
| 1-473 | | gum | |
| 1-474 | | oil | 7.59 (2H, d, J = 7.3 Hz), 7.45 (1H, t, J = 7.8 Hz), 7.38 (1H, t, J = 7.8 Hz), 7.38 (1H, t, J = 7.6 Hz), around7.28 (3H, m), 7.19 (1H, d, J = 7.9 Hz), 7.12 (1H, t, J = 7.6 Hz), 7.02 (1H, d, J = 7.8 Hz), 3.92-3.79 (3H, m), 2.12 (3H, s), 1.90-1.80 (1H, m), 1.67-1.64 (1H, m), around1.22 (3H, m), 0.96 (3H, dt, J = 16.9, 7.3 Hz) |
| 1-479 | | gum | 7.46-7.38 (1H, m), 7.35-7.25 (3H, m), 7.24-7.15 (2H, m), 7.14-7.00 (3H, m), 4.19-4.08 (1H, m), 3.87-3.77 (1H, m), 3.74-3.51 (2H, m), 3.40-3.26 (4H, m), 2.18 (3H, d, J = 7.2 Hz), 1.33 (3H, d, J = 8.0 Hz). |
| 1-484 | | amorphous | |
| 1-494 | | oil | |
| 1-503 | | gum | |
| 1-504 | | gum | 7.44 (1H, t, J = 7.6 Hz), 7.32-7.21 (5H, m), 7.04 (2H, m), 3.82-3.54 (5H, m), 2.16 (3H, s), 1.89-1.81 (1H, m), 1.70-1.63 (1H, m), 1.22 (3H, d, J = 6.9 Hz), 0.97 (3H, dt, J = 9.2, 7.3 Hz) |
| 1-506 | | gum | |
| 1-522 | | gum | 7.50 (1H, d, J = 7.8 Hz), around7.24 (1H, m), 7.21 (1H, t, J = 7.8 Hz), 7.15 (1H, d, J = 7.8 Hz), 4.01-3.94 (1H, m), 3.84-3.74 (2H, m), 3.57 (2H, s), 2.32 (3H, s), 1.91-1.75 (3H, m), 1.68-1.59 (2H, m), 1.20 (3H, d, J = 6.4 Hz), 0.90 (3H, t, J = 7.3 Hz) |
| 1-528 | | gum | 8.45 (1H, t, J = 5.7 Hz), 7.89 (1H, d, J = 7.8 Hz), around7.24 (4H, m), 7.06 (1H, t, J = 6.9 Hz), 7.01 (1H, t, J = 6.9 Hz), 7.01 (1H, t, J = 6.9 Hz), 4.30 (1H, dd, J = 17.4, 6.0 Hz), 3.88 (1H, d, J = 17.4 Hz), 3.78 (1H, m)2.12 (3H, s), 1.87 (1H, m), 1.66 (1H, m), 1.23 (3H, dd, J = 15.3, 6.6 Hz), 0.97 (3H, dt, J = 13.6, 5.4 Hz) |
| 1-575 | | gum | |
| 1-576 | | oil | 7.41-7.38 (1H, m), 7.33-7.28 (1H, m), 7.26-7.24 (1H, m), 7.19-7.14 (1H, m), 3.87 (3H, s), 3.57 (2H, s), 2.14 (3H, s), 1.44 (9H, s). |
| 1-577 | 75-80 | solid | 7.43-7.39 (1H, m), 7.33-7.28 (2H, m), 7.18 (1H, d, J = 7.8 Hz), 3.87 (3H, d, J = 4.1 Hz), 3.79-3.73 (1H, m), 3.63 (2H, d, J = 1.8 Hz), 2.04 (3H, s), 1.90-1.81 (1H, m), 1.69-1.59 (1H, m), 1.22 (3H, d, J = 6.4 Hz), 0.96 (3H, td, J = 7.4, 2.0 Hz). |
| 1-580 | | gum | |
| 1-583 | | oil | |
| 1-587 | 98-100 | solid | 7.41-7.36 (1H, m), 7.31-7.26 (2H, m), 7.20-7.16 (1H, m), 4.14-4.05 (1H, m), 3.88 (3H, d, J = 3.2 Hz), 3.62-3.56 (3H, m), 3.40-3.34 (1H, m), 3.30 (3H, d, J = 5.0 Hz), 2.06 (3H, d, J = 7.8 Hz), 1.31 (3H, dd, J = 7.8, 6.9 Hz). |
| 1-592 | | oil | |
| 1-594 | | oil | |
| 1-597 | | gum | |
| 1-598 | | oil | |
| 1-604 | 98-100 | solid | 7.41-7.37 (1H, m), 7.32-7.27 (2H, m), 7.26-7.24 (1H, m), 7.18 (1H, d, J = 7.6 Hz), 4.40-4.28 (2H, m), 3.63 (2H, s), 2.13 (3H, s), 1.44 (9H, s), 1.30 (3H, t, J = 7.6 Hz). |
| 1-605 | 73-75 | solid | 7.42-7.38 (1H, m), 7.33-7.28 (2H, m), 7.18 (1H, d, J = 7.3 Hz), 4.36-4.27 (2H, m), 3.78-3.63 (1H, m), 3.63 (2H, s), 2.03 (3H, d, J = 3.7 Hz), 1.90-1.82 (1H, m), 1.68-1.59 (1H, m), 1.35-1.26 (3H, m), 1.23-1.16 (3H, m), 0.96 (3H, t, J = 7.3 Hz). |
| 1-608 | 88 | solid | |
| 1-609 | | oil | |
| 1-611 | | oil | |
| 1-615 | 84-88 | solid | 7.39-7.35 (1H, m), 7.31-7.26 (2H, m), 7.18-7.16 (1H, m), 4.37-4.30 (2H, m), 4.14-4.07 (1H, m), 3.63-3.57 (3H, m), 3.41-3.35 (1H, m), 3.30 (3H, d, J = 5.0 Hz), 2.03 (3H, d, J = 6.4 Hz), 1.32-1.24 (6H, m). |
| 1-620 | | oil | |
| 1-622 | | oil | |
| 1-623 | | oil | |
| 1-626 | | oil | 7.38-7.27 (5H, m), 7.26-7.22 (1H, m), 7.21-7.08 (2H, m), 6.93-6.88 (0.5H, m), 6.55-6.50 (0.5H, m), 4.94 (1H, quint, J = 7.6 Hz), 4.35-4.23 (2H, m), 3.52 (2H, d, J = 5.6 Hz), 1.99 (1, 5H, s), 1.98 (1, 5H, s), 1.78 (1, 5H, d, J = 7.6 Hz), 1.75 (1, 5H, d, J = 7.6 Hz), 1.26 (3H, t, J = 6.8 Hz). |
| 1-631 | 104-106 | solid | |
| 1-632 | 84-86 | solid | |

TABLE 2-continued

| No. | Property (mp.° C.) | Form | ¹HNMR spectrum σ ppm: |
|---|---|---|---|
| 1-634 | | oil | |
| 1-641 | 144-146 | solid | |
| 1-642 | 108-110 | solid | 7.41-7.37 (1H, m), 7.32-7.27 (2H, m), 7.17 (1H, d, J = 7.3 Hz), 5.13-5.06 (1H, m), 3.78-3.73 (1H, m), 3.63 (2H, s), 2.01 (3H, d, J = 3.7 Hz), 1.90-1.82 (1H, m), 1.68-1.60 (1H, m), 1.34-1.27 (6H, m), 1.22 (3H, d, J = 6.4 Hz), 0.96 (3H, t, J = 7.3 Hz). |
| 1-647 | | oil | 7.39-7.35 (1H, m), 7.30-7.26 (2H, m), 7.18-7.14 (1H, m), 5.13-5.06 (1H, m), 4.13-4.04 (1H, m), 3.64-3.57 (3H, m), 3.39-3.33 (1H, m), 3.30 (3H, d, J = 4.6 Hz), 2.03 (3H, d, J = 6.4 Hz), 1.34-1.28 (9H, m). |
| 1-652 | | oil | |
| 1-653 | | oil | |
| 1-666 | | oil | |
| 1-667 | | amorphous | |
| 1-668 | | gum | |
| 1-669 | 78-80 | solid | 7.42-7.38 (1H, m), 7.34-7.28 (2H, m), 7.18 (1H, d, J = 7.8 Hz), 4.14-4.08 (1H, m), 4.02-3.95 (1H, m), 3.78-3.72 (1H, m), 3.64 (2H, s), 2.03 (3H, d, J = 4.1 Hz), 1.97-1.82 (2H, m), 1.67-1.52 (1H, m), 1.24-1.20 (3H, m), 0.97-0.93 (3H, m), 0.86-0.82 (6H, m). |
| 1-671 | | gum | |
| 1-674 | | amorphous | |
| 1-675 | | oil | 7.40-7.35 (1H, m), 7.31-7.27 (2H, m), 7.19-7.17 (1H, m), 4.14-4.06 (2H, m), 4.03-3.97 (1H, m), 3.64-3.56 (3H, m), 3.39-3.34 (1H, m), 3.30 (3H, d, J = 3.7 Hz), 2.04 (3H, d, J = 6.4 Hz), 1.96-1.89 (1H, m), 1.31 (3H, t, J = 6.9 Hz), 0.85 (6H, dd, J = 12.4, 6.4 Hz). |
| 1-676 | | oil | |
| 1-677 | | amorphous | |
| 1-678 | | oil | |
| 1-679 | | oil | |
| 1-706 | | oil | 7.42-7.38 (1H, m), 7.33-7.28 (2H, m), 7.19 (1H, d, J = 7.8 Hz), 5.91-5.80 (1H, m), 5.30-5.24 (2H, m), 4.79-4.67 (2H, m), 3.79-3.72 (1H, m), 3.63 (2H, s), 2.02 (3H, d, J = 4.1 Hz), 1.89-1.81 (1H, m), 1.69-1.59 (1H, m), 1.23-1.20 (3H, m), 0.97-0.93 (3H, m). |
| 1-707 | | gum | |
| 1-708 | | oil | 7.39-7.33 (1H, m), 7.25-7.20 (2H, m), 7.16 (1H, d, J = 8.0 Hz), 5.91-5.78 (1H, m), 5.36-5.21 (2H, m), 4.78-4.65 (2H, m), 4.13-4.03 (1H, m), 3.68-3.53 (3H, m), 3.39-3.30 (1H, m), 3.28 (1.5H, s), 3.27 (1.5H, s), 2.02 (1.5H, s), 2.00 (1.5H, s), 1.32-1.27 (3H, m). |
| 1-709 | | oil | |
| 1-710 | | oil | |
| 1-731 | | oil | 7.41-7.37 (1H, m), 7.32-7.28 (2H, m), 7.19 (1H, d, J = 7.3 Hz), 4.43-4.35 (2H, m), 3.81-3.73 (1H, m), 3.65-3.64 (2H, m), 3.60-3.52 (2H, m), 3.27 (2H, d, J = 2.7 Hz), 2.03 (3H, d, J = 2.7 Hz), 1.89-1.80 (1H, m), 1.69-1.59 (1H, m), 1.22 (3H, dd, J = 6.6, 2.5 Hz), 0.96 (3H, t, J = 7.3 Hz). |
| 1-733 | | oil | |
| 1-735 | | oil | |
| 1-736 | | oil | |
| 1-762 | | gum | |
| 1-763 | | amorphous | 7.45-7.18 (9H, m), 3.75 (3H, m), 2.03 (3H, brs), 1.90-1.78 (1H, m), 1.67-1.57 (1H, m), 1.20 (3H, d, J = 6.4 Hz), 0.93 (3H, brdt, J = 7.3 Hz, 1.8 Hz) |
| 1-765 | 117-121 | solid | 7.44-7.25 (7H, m), 7.23-7.15 (2H, m), 4.14-4.02 (1H, m), 3.73 (2H, dd, J = 5.6, 5.6 Hz), 3.62-3.52 (1H, m), 3.35-3.31 (1H, m), 3.28 (1.5H, s), 3.27 (1.5H, s), 2.06 (1.5H, s), 2.02 (1.5H, s), 1.30 (1.5H, d, J = 2.8 Hz), 1.28 (1.5H, d, J = 2.8 Hz). |
| 1-766 | | gum | |
| 1-781 | | oil | |
| 1-782 (TLC top) | | oil | |
| 1-783 (TLC bottom) | | oil | |
| 1-785 | | gum | |
| 1-788 (TLC top) | | oil | |
| 1-789 (TLC bottom) | | oil | |
| 1-790 | | oil | 7.39-7.32 (4H, m), 7.30-7.25 (4H, m), 7.15-7.13 (1H, m), 5.33-5.23 (2H, m), 4.14-4.03 (1H, m), 3.69-3.52 (3H, m), 3.38-3.32 (1H, m), 3.29 (3H, d, J = 5.0 Hz), 2.02 (3H, d, J = 6.4 Hz), 1.31-1.25 (3H, m). |
| 1-791 | | oil | |
| 1-793 | | oil | |
| 1-794 | | oil | |
| 1-796 | | oil | |
| 1-829 | | oil | 7.40 (1H, t, J = 6.9 Hz), 7.35-7.28 (2H, m), 7.20 (1H, d, J = 7.8 Hz), 4.34-4.28 (1H, m), 4.23-4.01 (2H, m), around 3.74 (1H, m), 3.65 (2H, s), 2.04 (3H, m), 2.00-1.46 (8H, m), around 1.23 (3H, m), 0.96 (3H, t, J = 7.3 Hz) |

TABLE 2-continued

| No. | Property (mp.° C.) | Form | ¹HNMR spectrum σ ppm: |
|---|---|---|---|
| 1-874 | | oil | |
| 1-886 | | oil | |
| 1-888 | 158-160 | solid | 7.42 (1H, m), 7.37-7.30 (2H, m), 7.16 (1H · m), 4.06 (1H, m), 3.69 (2H, m), 3.66 (3H, s), 2.03 (3H, s), around1.25 (6H, m) |
| 1-889 | | oil | |
| 1-890 | | oil | 7.45-7.41 (1H, m), 7.37-7.29 (2H, m), 7.22-7.19 (1H, m), 3.84-3.75 (1H, m), 3.71 (2H, d, J = 6.4 Hz), 3.63 (3H, s), 2.12 (3H, s), 1.91-1.82 (1H, m), 1.70-1.62 (1H, m), 1.27-1.22 (3H, m), 1.00-0.95 (3Hm). |
| 1-892 | | oil | |
| 1-893 | | oil | |
| 1-894 | | oil | |
| 1-895 | | oil | |
| 1-899 | | oil | |
| 1-900 | | oil | |
| 1-901 | | oil | |
| 1-903 | | oil | |
| 1-904 | | oil | |
| 1-906 | | gum | |
| 1-907 | | oil | |
| 1-913 | | oil | |
| 1-915 | | oil | 7.49-7.33 (2H, m), 7.32-7.26 (1H, m), 7.22-7.14 (1H, m), 4.19-4.07 (1H, m), 3.89-3.76 (1H, m), 3.73-3.62 (3H, m), 3.61-3.53 (1H, m), 3.41-3.32 (1H, m), 3.31-3.28 (3H, m), 2.17-2.08 (3H, m), 1.60 (3H, t, J = 7.2 Hz), 1.35-1.29 (3H, m). |
| 1-916 | | oil | |
| 1-917 | | oil | |
| 1-960 | 135-137 | solid | |
| 1-962 | 144-146 | solid | |
| 1-963 | | amorphous | 7.52-7.45 (1H, m), 7.38-7.34 (2H, m), 7.30-7.26 (1H, m), 3.71 (2H, s), 2.11 (3H, s), 1.46 (9H, s). |
| 1-964 | | gum | 7.52-7.48 (1H, m), 7.36-7.35 (3H, m), 3.79 (1H, m), 3.75 (2H, s), 2.01 (3H, s), 1.89 (1H, m), 1.67 (1H, m), 1.25 (3H, dJ = 6.9 Hz), 0.97 (3H, t, J = 7.3 Hz) |
| 1-965 | | oil | |
| 1-967 | 120-122 | solid | 7.52-7.46 (1H, m), 7.39-7.34 (3H, m), 3.73 (2H, s), 3.43 (2H, d, J = 6.9 Hz), 2.31-2.16 (1H, m), 2.00 (3H, s), 0.99 (6H, d, J = 6.9 Hz). |
| 1-968 | 113-115 | solid | |
| 1-969 | | amorphous | |
| 1-970 | | gum | |
| 1-971 | | oil | |
| 1-972 | | amorphous | |
| 1-973 | | gum | |
| 1-974 | | oil | |
| 1-975 | | gum | |
| 1-977 | | oil | |
| 1-978 | | gum | |
| 1-980 | | oil | |
| 1-981 | | oil | |
| 1-982 | 60-62 | solid | |
| 1-983 | 93.8-97.0 | solid | |
| 1-985 | | oil | |
| 1-986 | | amorphous | |
| 1-988 | 106-112 | solid | |
| 1-990 | 134-136 | solid | |
| 1-991 | 96-97 | solid | |
| 1-992 | | oil | |
| 1-993 | | oil | |
| 1-994 | 105 | solid | |
| 1-996 | | amorphous | |
| 1-997 | 116-118 | solid | 7.48-7.42 (1H, m), 7.35-7.28 (3H, m), 4.15-4.07 (1H, m), 3.72 (2H, d, J = 2.0 Hz), 3.61 (1H, dd, J = 9.6, 9.6 Hz), 3.37 (1H, dd, J = 9.6, 4.0 Hz), 3.30 (3H, s), 1.99 (3H, s), 1.32 (3H, d, J = 7.2 Hz). |
| 1-1000 | | oil | |
| 1-1002 | | oil | |
| 1-1003 | | oil | |
| 1-1005 | | oil | |
| 1-1006 | | oil | |
| 1-1008 | | oil | |
| 1-1009 | 105-107 | solid | |
| 1-1010 | | oil | |
| 1-1011 | | amorphous | |
| 1-1012 | 90-94 | solid | |
| 1-1013 | | gum | |
| 1-1014 | | gum | |
| 1-1015 | | gum | |
| 1-1016 | 112-117 | solid | |
| 1-1017 | 119.6 | solid | |
| 1-1018 | 108 | solid | |
| 1-1019 | | gum | |

TABLE 2-continued

| No. | Property (mp.° C.) | Form | ¹HNMR spectrum σ ppm: |
|---|---|---|---|
| 1-1020 | 118 | solid | |
| 1-1021 | | gum | |
| 1-1022 | | oil | |
| 1-1023 | | oil | |
| 1-1026 | | oil | |
| 1-1027 | | gum | |
| 1-1028 | | gum | |
| 1-1029 | 124-126 | solid | |
| 1-1030 | 107-112 | solid | |
| 1-1031 | | oil | |
| 1-1032 | 172-175 | solid | |
| 1-1033 | 108.7-113.4 | solid | |
| 1-1034 | | oil | |
| 1-1036 | | gum | |
| 1-1037 | | oil | |
| 1-1038 | | gum | |
| 1-1039 | | gum | |
| 1-1040 | | gum | |
| 1-1041 | | gum | |
| 1-1042 | | gum | |
| 1-1043 | | oil | |
| 1-1044 | | oil | |
| 1-1045 | | gum | |
| 1-1046 | | gum | |
| 1-1047 | | amorphous | |
| 1-1048 | | gum | |
| 1-1049 | | gum | |
| 1-1050 | | gum | |
| 1-1051 | | oil | |
| 1-1054 | | oil | |
| 1-1055 | | oil | |
| 1-1057 | | oil | |
| 1-1058 | | oil | |
| 1-1059 | 88-92 | solid | |
| 1-1061 | | oil | |
| 1-1063 | 151-153 | solid | |
| 1-1064 | | oil | |
| 1-1066 | | oil | |
| 1-1093 | | oil | |
| 1-1127 | | gum | 7.80 (2H, d, J = 8.2 Hz), 7.39 (2H, d, J = 8.2 Hz), around7.39 (1H, m), around7.24 (1H, m), 7.20 (1H, d, J = 7.8 Hz), 7.12 (1H, dJ = 7.8 Hz), 4.02 (1H, m), 3.46 (1H, d, J = 17.4 Hz), 3.12 (1H, d, J = 17.4 Hz), 2.49 (3H, s), 2.05 (3H, s), 1.29-1.26 (6H, m) |

Although the Reference Examples below show Synthesis Examples for synthesizing the starting substances of the syntheses above from commercial products, the syntheses are not limited to the examples.

Reference Example 1

Synthesis of 3-methyl-4-[(2-nitrophenyl)methyl]-2H-isoxazol-5-one

Ethyl acetoacetate (834 g, 641 mmol) was added at 0° C. to a dimethoxyethane solution (1000 ml) of 60% sodium hydride (25.6 g, 641 mmol), and the mixture was stirred at room temperature for 30 minutes. To the mixture solution, 2-Nitrobenzyl chloride (100 g, 583 mmol) (manufactured by Tokyo Chemical Industry Co., Ltd.) was added at 0° C., and the mixture solution was stirred at 80° C. for three hours. The reaction mixture was poured into an aqueous dilute hydrochloric acid solution, followed by extraction with ethyl acetate. The extraction liquid was washed with saturated brine, dried over anhydrous sodium sulfate and then concentrated under reduced pressure, and ethyl 2-[(2-nitrophenyl)methyl]-3-oxo-butanoate (amount of 155 g, yield of 100%) as a yellow oil was thus obtained. Hydroxylamine chloride (60.7 g, 873 mmol) was added to a methanol solution (500 ml) of the obtained oil, and the mixture was stirred at 80° C. for an hour. Water was poured into the reaction mixture, followed by extraction with ethyl acetate. The extraction liquid was washed with saturated brine, dried over anhydrous sodium sulfate and then concentrated under reduced pressure. The concentrate was washed with a mixed solvent (ethyl acetate/n-hexane=1/2), and the title compound (amount of 100 g, yield of 73%) as a white solid was thus obtained.

Melting point: 148 to 150° C.
¹HNMR spectrum (DMSO-d6) σ: 12.1 (1H, br.s), 7.89 (1H, d, J=7.6 Hz), 7.60 (1H, t, J=7.6 Hz), 7.44 (1H, t, J=7.6 Hz), 7.36 (1H, d, J=7.6 Hz), 2.00 (3H, s).

Reference Example 2

Synthesis of 2-isobutyl-3-methyl-4-[(2-nitrophenyl)methyl]isoxazol-5-one

Potassium carbonate (5.50 g, 40.0 mmol) and 1-iodo-2-methylpropane (5.80 g, 32.0 mmol) were added to a N,N-dimethylformamide solution (15 ml) of 3-methyl-4-[(2-nitrophenyl)methyl]-2H-isoxazol-5-one (6.20 g, 26.0 mmol), and the mixture was stirred at 80° C. for five hours. Water was poured into the reaction mixture, followed by extraction with ethyl acetate. The extraction liquid was washed with saturated brine, dried over anhydrous sodium sulfate and then concentrated under reduced pressure. The concentrate was purified by silica gel column chromatography (eluent: ethyl acetate/n-hexane=1/5), and the title compound (amount of 3.50 g, yield of 46%) as a yellow gum was thus obtained. $^1$HNMR spectrum (CDCl$_3$) σ: 7.89 (1H, d, J=7.8 Hz), 7.55-7.51 (2H, m), 7.38-7.34 (1H, m), 3.89 (2H, s), 3.37 (2H, d, J=6.4 Hz), 2.22-2.14 (1H, m), 2.13 (3H, s), 0.96 (6H, d, J=6.4 Hz).

Reference Example 3

Synthesis of 3-methyl-4-[(2-nitrophenyl)methyl]-2-sec-butyl-isoxazol-5-one

The same reaction and treatment as those in Reference Example 2 were conducted using 2-iodobutane instead of 1-iodo-2-methylpropane, and the title compound (yield of 47%) as a yellow gum was thus obtained. $^1$HNMR spectrum (CDCl$_3$) σ: 7.89 (1H, d, J=7.8 Hz), 7.54-7.51 (2H, m), 7.38-7.34 (1H, m), 3.90 (2H, d, J=2.3 Hz), 3.88-3.72 (1H, m), 2.13 (3H, s), 1.86-1.79 (1H, m), 1.65-1.58 (1H, m), 1.19 (3H, d, J=7.0 Hz), 0.94 (3H, t, J=7.0 Hz).

Reference Example 4

Synthesis of 2-(2-methoxy-1-methyl-ethyl)-3-methyl-4-[(2-nitrophenyl)methyl]-isoxazol-5-one The same reaction and treatment as those in Reference Example 2 were conducted using (2-methoxy-1-methyl-ethyl) 4-methylbenzenesulfonate instead of 1-iodo-2-methylpropane, and the title compound (yield of 40%) as a light red solid was thus obtained.
Melting point: 89 to 91° C.
$^1$HNMR spectrum (CDCl$_3$) σ: 7.91 (1H, d, J=8.0 Hz), 7.54-7.47 (2H, m), 7.38-7.34 (1H, m), 4.13-4.05 (1H, m), 3.92 (2H, m), 3.56 (1H, t, J=10.0 Hz), 3.36 (1H, dd, J=10.0, 4.0 Hz), 3.27 (3H, s), 2.14 (3H, s), 1.28 (3H, d, J=6.8 Hz).

Reference Example 5

Synthesis of 4-[(2-aminophenyl)methyl]-2-isobutyl-3-methylisoxazol-5-one

Reduced iron (3.00 g), ammonium chloride (1.81 g, 33.9 mmol) and water (10 ml) were added to an ethanol solution (30 ml) of 2-isobutyl-3-methyl-4-[(2-nitrophenyl)methyl] isoxazol-5-one (1.97 g, 6.79 mmol), and the mixture was stirred at 90° C. for an hour. The reaction mixture was filtered through Celite, and an aqueous saturated sodium hydrogen carbonate solution was poured, followed by extraction with ethyl acetate. The extraction liquid was washed with saturated brine, dried over anhydrous sodium sulfate and then concentrated under reduced pressure. The concentrate was purified by silica gel column chromatography (eluent: ethyl acetate/n-hexane=1/3), and the title compound (amount of 1.73 g, yield of 98%) as a yellow oil was thus obtained.
$^1$HNMR spectrum (CDCl$_3$) σ: 7.05-6.98 (2H, m), 6.67-6.63 (2H, m), 4.32 (2H, br.s), 3.43 (2H, s), 3.31 (2H, d, J=7.0 Hz), 2.22-2.12 (1H, m), 2.13 (3H, s), 0.94 (6H, d, J=7.0 Hz).

Reference Example 6

Synthesis of 4-[(2-aminophenyl)methyl]-3-methyl-2-sec-butylisoxazol-5-one

The same reaction and treatment as those in Reference Example 5 were conducted using 3-methyl-4-[(2-nitrophenyl)methyl]-2-sec-butyl-isoxazol-5-one instead of 2-isobutyl-3-methyl-4-[(2-nitrophenyl)methyl]isoxazol-5-one, and the title compound (yield of 97%) as a yellow oil was thus obtained.
$^1$HNMR spectrum (CDCl$_3$) σ: 7.05-6.99 (2H, m), 6.67-6.63 (2H, m), 4.28 (2H, br.s), 3.74-3.67 (1H, m), 3.40 (2H, s), 2.12 (3H, s), 1.86-1.75 (1H, m), 1.65-1.57 (1H, m), 1.17 (3H, d, J=7.0 Hz), 0.92 (3H, d, J=7.0 Hz).

Reference Example 7

Synthesis of 4-[(2-aminophenyl)methyl]-2-(2-methoxy-1-methyl-ethyl)-3-methyl-isoxazolin-5-one The same reaction and treatment as those in Reference Example 5 were conducted using 2-(2-methoxy-1-methyl-ethyl)-3-methyl-4-[(2-nitrophenyl)methyl]-isoxazol-5-one instead of 2-isobutyl-3-methyl-4-[(2-nitrophenyl)methyl] isoxazol-5-one, and the title compound (yield of 99%) as a yellow oil was thus obtained.
$^1$HNMR spectrum (CDCl$_3$) σ: 7.03-6.99 (2H, m), 6.67-6.62 (2H, m), 4.22 (2H, br.s), 4.08-4.00 (1H, m), 3.48 (1H, t, J=10.0 Hz), 3.43 (2H, s), 3.35 (1H, dd, J=10.0, 4.0 Hz), 2.12 (3H, s), 3.18 (3H, s), 2.15 (3H, s), 1.25 (3H, d, J=6.8 Hz).

Reference Example 8

Synthesis of [2-ethoxy-1-[(2-nitrophenyl)methyl]2-oxo-ethyl]triphenyl-phosphonium bromide Ethyl (triphenylphosphoranylidene)acetate (25.0 g, 71.8 mmol) was added at room temperature to a chloroform (500 ml) solution of 2-nitrobenzyl bromide (15.5 g, 71.8 mol), and the mixture was heated under reflux for five hours. The reaction mixture was concentrated under reduced pressure, and the obtained concentrate was purified by silica gel column chromatography (eluent: ethyl acetate/n-hexane=9/1). The title compound (amount of 29.0 g, yield of 72%) as a brown gum was thus obtained.
$^1$HNMR spectrum (CDCl$_3$) σ: 8.00-7.38 (19H, m), 3.80 (2H, q, J=7.2 Hz), 3.69-3.55 (3H, m), 0.51 (3H, t, J=7.2 Hz).

Reference Example 9

Synthesis of ethyl 2-[(2-nitrophenyl)methyl]buta-2,3-dienoate

Diisopropylethylamine (2.98 g, 23.0 mmol) was added at room temperature to a chloroform (80 ml) solution of [2-ethoxy-1-[(2-nitrophenyl)methyl]2-oxo-ethyl]triphenyl-phosphonium bromide (13.0 g, 23.0 mmol), and the mixture was stirred at the same temperature for 30 minutes. Then, acetyl chloride (1.81 g, 23.0 mmol) was dropped using a dropping funnel, and the mixture was stirred at the same temperature for an hour. The reaction mixture was concentrated under reduced pressure, and the obtained concentrate was purified by silica gel column chromatography (eluent: ethyl acetate/n-hexane=1/1). The title compound (amount of 5.69 g, yield of 100%) as a light-yellow oil was thus obtained.
$^1$HNMR spectrum (CDCl$_3$) σ: 7.92-7.90 (1H, m), 7.51 (1H, m), 7.39-7.34 (2H, m), 5.02 (2H, t, J=3.2 Hz), 4.18 (2H, q, J=7.0 Hz), 3.92 (2H, t, J=3.2 Hz), 1.25 (3H, t, J=7.0 Hz).

Reference Example 10

Synthesis of 2-tert-butyl-3-methyl-[(2-nitrophenyl)methyl]isoxazol-5-one

N-(Tert-butyl)hydroxylamine hydrochloride (1.68 g, 13.4 mmol) and triethylamine (1.35 g, 13.4 mmol) were added to a toluene (15 ml) solution of ethyl 2-[(2-nitrophenyl)methyl]buta-2,3-dienoate (3.00 g, 12.1 mmol), and the mixture was stirred at 100° C. for 10 minutes. The reaction mixture was concentrated under reduced pressure, and the obtained concentrate was purified by silica gel column chromatography (eluent: ethyl acetate/n-hexane=1/1). The title compound (amount of 3.5 g, yield of 100%) as a white solid was thus obtained.

Melting point: 86 to 88° C.
$^1$HNMR spectrum (CDCl$_3$) σ: 7.89 (1H, m), 7.53 (1H, m), 7.46 (1H, m), 7.37 (1H, m), 3.91 (2H, s), 2.23 (3H, s), 1.42 (9H, s).

Reference Example 11

Synthesis of 4-[(2-aminophenyl)methyl]-2-tert-butyl-isoxazol-5-one

The same reaction and treatment as those in Reference Example 5 were conducted using 2-tert-butyl-3-methyl-[(2-nitrophenyl)methyl]isoxazol-5-one instead of 2-isobutyl-3-methyl-4-[(2-nitrophenyl)methyl]isoxazol-5-one, and the title compound (yield of 86%) as a light-yellow solid was thus obtained.

Melting point: 98 to 100° C.
$^1$HNMR spectrum (CDCl$_3$) σ: 7.01 (2H, m), 6.65 (2H, m), 4.27 (2H, brs), 3.44 (2H, s), 2.25 (3H, s), 1.40 (9H, s)

Next, the methods for formulating the compounds of the invention as herbicides are explained specifically by the Formulation Examples below. In this regard, however, the herbicides are not limited to these Formulation Examples only and can be blended with various other additives at any ratios and formulated.

Formulation Example 1 (Granules

Fifteen parts of water was added to 1 part of the compound of Synthesis Example 1, 1 part of calcium lignin sulfonate, 1 part of lauryl sulfate, 30 parts of bentonite and 67 parts of talc, and the mixture was kneaded with a kneader and then granulated with an extrusion granulator. By drying the granules with a fluidized-bed dryer, granules containing 1% active herbicide ingredient can be obtained. Furthermore, granules can be obtained by the same method except that each compound in Table 1 is used instead of the compound of Synthesis Example 1.

Formulation Example 2 (Flowable Agent

By evenly mixing and pulverizing 20.0 parts of the compound of Synthesis Example 1, 2.0 parts of di-2-ethylhexyl sulfosuccinate sodium salt, 2.0 parts of polyoxyethylene nonylphenyl ether, 5.0 parts of propylene glycol, 0.5 parts of a defoaming agent and 70.5 parts of water in a wet type ball mill, a flowable agent containing 20% active herbicide ingredient can be obtained. Furthermore, a flowable agent can be obtained by the same method except that each compound in Table 1 is used instead of the compound of Synthesis Example 1.

Formulation Example 3 (Dry Flowable Agent

By evenly mixing and finely pulverizing 75 parts of the compound of Synthesis Example 1, 10 parts of naphthalene sulfonate formaldehyde condensate, 5 parts of sodium lauryl sulfate, 5 parts of white carbon and 5 parts of clay, a dry flowable (granulate water dispersible) agent containing 75% active herbicide ingredient can be obtained. Furthermore, a dry flowable (granulate water dispersible) agent can be obtained by the same method except that each compound in Table 1 is used instead of the compound of Synthesis Example 1.

Formulation Example 4 (Water Dispersible Powder

By evenly mixing 15 parts of the compound of Synthesis Example 1, 15 parts of white carbon, 3 parts of calcium lignin sulfonate, 2 parts of polyoxyethylene alkyl ether, 5 parts of diatomaceous earth and 60 parts of clay with a pulverizing mixer, water dispersible powder containing 15% active herbicide ingredient can be obtained. Furthermore, water dispersible powder can be obtained by the same method except that each compound in Table 1 is used instead of the compound of Synthesis Example 1.

Formulation Example 5 (Emulsion

By mixing 20 parts of the compound of Synthesis Example 1, 18 parts of polyoxyethylene styrylphenylether, 2 parts of calcium dodecylbenzene sulfonate and 60 parts of xylene, an emulsion containing 20% active herbicide ingredient can be obtained. Furthermore, an emulsion can be obtained by the same method except that each compound in Table 1 is used instead of the compound of Synthesis Example 1.

Formulation Example 6 (Powder

By evenly mixing and pulverizing 0.5 parts of the compound of Synthesis Example 1, 0.5 parts of white carbon, 0.5 parts of calcium stearate, 50.0 parts of clay and 48.5 parts of talc, powder containing 0.5% active herbicide ingredient can be obtained. Furthermore, powder can be obtained by the same method except that each compound in Table 1 is used instead of the compound of Synthesis Example 1.

Formulation Example 7 (Jumbo Agent

After mixing 15 parts of the compound of Synthesis Example 1, 2 parts of sodium lauryl sulfate, 5 parts of di-2-ethylhexyl sulfosuccinate sodium salt, 5 parts of carboxymethyl cellulose sodium salt, 35 parts of Shirasu-balloon, 10 parts of lactose and 28 parts of expanded perlite, 35 parts of water was added, and the mixture was kneaded with a kneader and then granulated with an extrusion granulator. By drying the granules with a fluidized-bed dryer, a jumbo agent containing 15% active herbicide ingredient can be obtained. Furthermore, a jumbo agent can be obtained by the same method except that each compound in Table 1 is used instead of the compound of Synthesis Example 1.

Next, Test Examples are shown in order to demonstrate the herbicidal effect of the isoxazolin-5-one derivatives of the invention.

Test Example 1

Herbicidal Effect Test by Treatment of Rice Paddy Soil

Wagner pots with an area of 1/10000 ares were filled with a paddy soil, and after adding water, a compound fertilizer (N:P:K=17:17:17) was added, followed by soil puddling. Then, *Echinochloa crus-galli*, broad leaf weeds (*Lindernia pyxidaria* and *Monochoria vaginalis*) and *Scirpus juncoides*, 30 seeds each, were sown in a depth of 0 to 1 cm. Water was poured immediately after seeding, and the water depth was kept at about 3 cm. The subsequent management was conducted in a glass greenhouse. Immediately after that, emulsions prepared using the compounds in Table 3 below according to Formulation Example 5 were diluted with water, and a certain amount of the water-diluted agent solutions were dropped. The converted amount of the applied active ingredient corresponded to 120 g per 10 ares.

This test was conducted in a double system per one agent solution concentration area, and the herbicidal rates (%) were determined by the following equation (Math. 1) on 14 days after the treatment with the agents.

Herbicidal Rate (%)={1-(Average Dry Weight (g) of Plant of Treated Area)/(Average Dry Weight (g) of Plant of Untreated Area)}×100   [Math. 1]

The results are shown in Table 3 below. In this regard, a herbicidal rate of 80% or more is the maximum effect, and it has been confirmed that the effect is exhibited also in a test at a low concentration. The compound numbers in Table 3 are the same as those in Table 1 and Table 2 above.

TABLE 3

| No. | Concentration (g/10a) | Echinochloa crus-galli | Monochoria vaginalis | Lindernia pyxidaria | Scirpus juncoides |
|---|---|---|---|---|---|
| 1-28 | 120 | 100 | 100 | 90 | 90 |
| 1-29 | 120 | 100 | 90 | 90 | 90 |
| 1-31 | 120 | 90 | 80 | 90 | 90 |
| 1-32 | 120 | 80 | 90 | 80 | 90 |
| 1-33 | 120 | 80 | 90 | 90 | 100 |
| 1-37 | 120 | 60 | 40 | 80 | 90 |
| 1-41 | 120 | 100 | 100 | 100 | 100 |
| 1-46 | 120 | 60 | 80 | 80 | 90 |
| 1-47 | 120 | 40 | 70 | 70 | 80 |
| 1-63 | 120 | 90 | 100 | 100 | 100 |
| 1-68 | 120 | 80 | 80 | 90 | 90 |
| 1-69 | 120 | 80 | 70 | 70 | 90 |
| 1-78 | 120 | 40 | 50 | 50 | 70 |
| 1-81 | 120 | 90 | 80 | 80 | 90 |
| 1-83 | 120 | 90 | 70 | 100 | 90 |
| 1-84 | 120 | 80 | 70 | 70 | 80 |
| 1-97 | 120 | 100 | 100 | 100 | 100 |
| 1-98 | 120 | 100 | 100 | 100 | 90 |
| 1-100 | 120 | 90 | 100 | 100 | 90 |
| 1-101 | 120 | 90 | 90 | 90 | 90 |
| 1-102 | 120 | 100 | 100 | 100 | 100 |
| 1-103 | 120 | 100 | 100 | 80 | 90 |
| 1-105 | 120 | 90 | 100 | 100 | 90 |
| 1-106 | 120 | 90 | 90 | 90 | 90 |
| 1-109 | 120 | 100 | 100 | 100 | 100 |
| 1-110 | 120 | 100 | 100 | 100 | 100 |
| 1-112 | 120 | 100 | 90 | 90 | 90 |
| 1-113 | 120 | 100 | 100 | 100 | 100 |
| 1-115 | 120 | 100 | 90 | 90 | 90 |
| 1-116 | 120 | 90 | 80 | 90 | 90 |
| 1-120 | 120 | 100 | 100 | 100 | 100 |
| 1-124 | 120 | 100 | 90 | 90 | 90 |
| 1-130 | 120 | 100 | 100 | 100 | 100 |
| 1-133 | 120 | 80 | 100 | 100 | 100 |
| 1-134 | 120 | 80 | 80 | 60 | 80 |
| 1-135 | 120 | 90 | 60 | 90 | 90 |
| 1-136 | 120 | 100 | 70 | 80 | 90 |
| 1-137 | 120 | 90 | 70 | 90 | 90 |
| 1-138 | 120 | 90 | 100 | 100 | 90 |
| 1-142 | 120 | 100 | 90 | 100 | 90 |
| 1-143 | 120 | 90 | 100 | 100 | 90 |
| 1-144 | 120 | 100 | 100 | 90 | 90 |
| 1-145 | 120 | 100 | 100 | 100 | 100 |
| 1-146 | 120 | 100 | 100 | 100 | 100 |
| 1-148 | 120 | 90 | 90 | 100 | 100 |
| 1-149 | 120 | 90 | 90 | 90 | 90 |
| 1-155 | 120 | 90 | 60 | 60 | 80 |
| 1-156 | 120 | 100 | 80 | 100 | 100 |
| 1-162 | 120 | 100 | 100 | 100 | 100 |
| 1-166 | 120 | 100 | 90 | 90 | 90 |
| 1-167 | 120 | 100 | 80 | 90 | 90 |
| 1-180 | 120 | 90 | 90 | 90 | 90 |
| 1-181 | 120 | 90 | 90 | 100 | 90 |
| 1-182 | 120 | 90 | 90 | 100 | 100 |
| 1-183 | 120 | 100 | 100 | 100 | 100 |
| 1-186 | 120 | 90 | 100 | 100 | 90 |
| 1-187 | 120 | 90 | 90 | 90 | 80 |
| 1-189 | 120 | 90 | 90 | 100 | 90 |
| 1-191 | 120 | 90 | 90 | 100 | 90 |
| 1-192 | 120 | 90 | 100 | 100 | 40 |
| 1-193 | 120 | 90 | 100 | 100 | 90 |
| 1-194 | 120 | 80 | 80 | 100 | 80 |
| 1-195 | 120 | 90 | 60 | 70 | 90 |
| 1-198 | 120 | 80 | 100 | 100 | 80 |
| 1-199 | 120 | 100 | 100 | 100 | 90 |
| 1-200 | 120 | 90 | 100 | 100 | 90 |
| 1-201 | 120 | 90 | 80 | 90 | 100 |
| 1-202 | 120 | 100 | 90 | 100 | 80 |
| 1-203 | 120 | 90 | 100 | 100 | 90 |
| 1-204 | 120 | 100 | 90 | 90 | 90 |
| 1-205 | 120 | 100 | 100 | 100 | 90 |
| 1-206 | 120 | 90 | 100 | 100 | 90 |
| 1-207 | 120 | 100 | 100 | 100 | 90 |
| 1-208 | 120 | 90 | 90 | 80 | 90 |
| 1-209 | 120 | 90 | 60 | 60 | 70 |
| 1-211 | 120 | 90 | 90 | 90 | 90 |
| 1-212 | 120 | 90 | 80 | 90 | 90 |
| 1-213 | 120 | 100 | 90 | 90 | 90 |
| 1-214 | 120 | 100 | 90 | 100 | 90 |
| 1-215 | 120 | 100 | 80 | 100 | 90 |
| 1-216 | 120 | 90 | 100 | 100 | 100 |
| 1-218 | 120 | 100 | 90 | 90 | 90 |
| 1-219 | 120 | 100 | 80 | 90 | 90 |
| 1-220 | 120 | 90 | 100 | 100 | 90 |
| 1-221 | 120 | 90 | 60 | 70 | 80 |
| 1-222 | 120 | 100 | 90 | 90 | 90 |
| 1-224 | 120 | 100 | 100 | 100 | 90 |
| 1-229 | 120 | 70 | 100 | 80 | 90 |
| 1-230 | 120 | 100 | 80 | 100 | 90 |
| 1-231 | 120 | 90 | 90 | 80 | 80 |
| 1-232 | 120 | 90 | 90 | 80 | 90 |
| 1-235 | 120 | 90 | 80 | 60 | 80 |
| 1-237 | 120 | 90 | 80 | 90 | 80 |
| 1-238 | 120 | 100 | 80 | 80 | 80 |
| 1-248 | 120 | 60 | 80 | 90 | 50 |
| 1-251 | 120 | 100 | 100 | 90 | 80 |
| 1-263 | 120 | 50 | 50 | 80 | 60 |
| 1-264 | 120 | 90 | 90 | 80 | 100 |
| 1-293 | 120 | 90 | 90 | 90 | 90 |
| 1-294 | 120 | 90 | 90 | 90 | 90 |
| 1-295 | 120 | 90 | 90 | 90 | 90 |
| 1-297 | 120 | 100 | 100 | 100 | 100 |
| 1-298 | 120 | 90 | 90 | 90 | 90 |
| 1-299 | 120 | 100 | 80 | 100 | 90 |
| 1-300 | 120 | 100 | 70 | 80 | 90 |
| 1-304 | 120 | 90 | 90 | 90 | 90 |
| 1-305 | 120 | 90 | 90 | 90 | 90 |
| 1-310 | 120 | 90 | 90 | 90 | 90 |
| 1-315 | 120 | 90 | 90 | 90 | 90 |
| 1-316 | 120 | 90 | 90 | 90 | 90 |
| 1-318 | 120 | 90 | 90 | 90 | 90 |
| 1-319 | 120 | 90 | 90 | 90 | 90 |
| 1-320 | 120 | 90 | 90 | 90 | 90 |
| 1-321 | 120 | 90 | 90 | 90 | 90 |

TABLE 3-continued

| No. | Concentration (g/10a) | Echinochloa crus-galli | Monochoria vaginalis | Lindernia pyxidaria | Scirpus juncoides |
|---|---|---|---|---|---|
| 1-329 | 120 | 90 | 90 | 90 | 90 |
| 1-330 | 120 | 90 | 90 | 90 | 90 |
| 1-331 | 120 | 90 | 90 | 90 | 90 |
| 1-333 | 120 | 90 | 90 | 90 | 90 |
| 1-334 | 120 | 100 | 80 | 70 | 90 |
| 1-335 | 120 | 90 | 90 | 90 | 90 |
| 1-336 | 120 | 90 | 90 | 90 | 90 |
| 1-337 | 120 | 90 | 90 | 90 | 90 |
| 1-351 | 120 | 90 | 90 | 90 | 90 |
| 1-352 | 120 | 90 | 90 | 90 | 90 |
| 1-353 | 120 | 90 | 90 | 90 | 90 |
| 1-354 | 120 | 100 | 90 | 90 | 90 |
| 1-355 | 120 | 90 | 90 | 90 | 90 |
| 1-356 | 120 | 100 | 60 | 90 | 90 |
| 1-357 | 120 | 90 | 90 | 90 | 90 |
| 1-358 | 120 | 90 | 90 | 90 | 90 |
| 1-359 | 120 | 90 | 90 | 90 | 90 |
| 1-403 | 120 | 90 | 90 | 90 | 90 |
| 1-404 | 120 | 90 | 90 | 90 | 90 |
| 1-405 | 120 | 90 | 90 | 90 | 90 |
| 1-407 | 120 | 90 | 90 | 90 | 90 |
| 1-408 | 120 | 100 | 80 | 80 | 90 |
| 1-412 | 120 | 90 | 90 | 90 | 90 |
| 1-413 | 120 | 90 | 90 | 90 | 90 |
| 1-416 | 120 | 90 | 90 | 90 | 90 |
| 1-431 | 120 | 90 | 90 | 90 | 90 |
| 1-432 | 120 | 90 | 90 | 90 | 90 |
| 1-434 | 120 | 90 | 90 | 90 | 90 |
| 1-444 | 120 | 90 | 90 | 90 | 90 |
| 1-472 | 120 | 90 | 60 | 90 | 90 |
| 1-473 | 120 | 90 | 90 | 90 | 90 |
| 1-474 | 120 | 90 | 90 | 90 | 90 |
| 1-479 | 120 | 90 | 90 | 90 | 90 |
| 1-484 | 120 | 90 | 90 | 90 | 90 |
| 1-494 | 120 | 90 | 90 | 90 | 90 |
| 1-503 | 120 | 90 | 90 | 90 | 90 |
| 1-504 | 120 | 90 | 90 | 90 | 90 |
| 1-506 | 120 | 90 | 90 | 90 | 90 |
| 1-522 | 120 | 90 | 90 | 90 | 90 |
| 1-528 | 120 | 90 | 90 | 90 | 90 |
| 1-575 | 120 | 90 | 100 | 100 | 100 |
| 1-576 | 120 | 90 | 90 | 90 | 90 |
| 1-577 | 120 | 90 | 90 | 90 | 90 |
| 1-580 | 120 | 90 | 90 | 90 | 90 |
| 1-583 | 120 | 100 | 90 | 90 | 90 |
| 1-587 | 120 | 90 | 90 | 90 | 90 |
| 1-592 | 120 | 90 | 90 | 90 | 90 |
| 1-597 | 120 | 90 | 100 | 90 | 90 |
| 1-598 | 120 | 90 | 90 | 90 | 90 |
| 1-604 | 120 | 90 | 90 | 90 | 90 |
| 1-605 | 120 | 90 | 90 | 90 | 90 |
| 1-608 | 120 | 70 | 80 | 70 | 90 |
| 1-609 | 120 | 90 | 90 | 90 | 90 |
| 1-611 | 120 | 100 | 80 | 90 | 90 |
| 1-615 | 120 | 90 | 90 | 90 | 90 |
| 1-620 | 120 | 90 | 90 | 90 | 90 |
| 1-626 | 120 | 90 | 90 | 90 | 90 |
| 1-631 | 120 | 90 | 90 | 90 | 90 |
| 1-632 | 120 | 90 | 90 | 90 | 90 |
| 1-634 | 120 | 90 | 90 | 90 | 90 |
| 1-641 | 120 | 90 | 90 | 90 | 90 |
| 1-642 | 120 | 90 | 90 | 90 | 90 |
| 1-647 | 120 | 90 | 90 | 90 | 90 |
| 1-652 | 120 | 90 | 90 | 90 | 90 |
| 1-653 | 120 | 90 | 90 | 90 | 90 |
| 1-666 | 120 | 100 | 100 | 80 | 90 |
| 1-667 | 120 | 90 | 90 | 90 | 90 |
| 1-668 | 120 | 90 | 90 | 90 | 90 |
| 1-669 | 120 | 90 | 90 | 90 | 90 |
| 1-671 | 120 | 90 | 90 | 90 | 90 |
| 1-674 | 120 | 100 | 90 | 90 | 90 |
| 1-675 | 120 | 90 | 90 | 90 | 90 |
| 1-676 | 120 | 90 | 90 | 90 | 90 |
| 1-677 | 120 | 90 | 100 | 100 | 90 |
| 1-678 | 120 | 90 | 90 | 90 | 90 |
| 1-679 | 120 | 60 | 50 | 50 | 50 |
| 1-706 | 120 | 90 | 90 | 90 | 90 |
| 1-707 | 120 | 90 | 90 | 90 | 90 |
| 1-708 | 120 | 90 | 90 | 90 | 90 |
| 1-709 | 120 | 90 | 90 | 90 | 90 |
| 1-710 | 120 | 90 | 90 | 90 | 90 |
| 1-731 | 120 | 90 | 90 | 90 | 90 |
| 1-733 | 120 | 100 | 90 | 90 | 100 |
| 1-735 | 120 | 90 | 90 | 90 | 90 |
| 1-736 | 120 | 90 | 90 | 90 | 90 |
| 1-762 | 120 | 90 | 90 | 90 | 90 |
| 1-763 | 120 | 90 | 90 | 90 | 90 |
| 1-765 | 120 | 90 | 90 | 90 | 90 |
| 1-766 | 120 | 90 | 90 | 90 | 90 |
| 1-781 | 120 | 90 | 90 | 90 | 90 |
| 1-783 (TLC bottom) | 120 | 90 | 90 | 90 | 90 |
| 1-785 | 120 | 90 | 90 | 90 | 90 |
| 1-788 (TLC top) | 120 | 80 | 50 | 60 | 80 |
| 1-789 (TLC bottom) | 120 | 100 | 90 | 90 | 90 |
| 1-790 | 120 | 90 | 90 | 90 | 90 |
| 1-796 | 120 | 90 | 90 | 90 | 90 |
| 1-829 | 120 | 90 | 90 | 90 | 90 |
| 1-874 | 120 | 90 | 90 | 90 | 90 |
| 1-886 | 120 | 90 | 90 | 90 | 90 |
| 1-888 | 120 | 100 | 90 | 100 | 90 |
| 1-889 | 120 | 90 | 90 | 90 | 90 |
| 1-890 | 120 | 90 | 90 | 90 | 90 |
| 1-892 | 120 | 100 | 90 | 90 | 90 |
| 1-893 | 120 | 90 | 90 | 90 | 90 |
| 1-894 | 120 | 100 | 60 | 80 | 100 |
| 1-895 | 120 | 100 | 80 | 90 | 90 |
| 1-899 | 120 | 90 | 90 | 90 | 90 |
| 1-900 | 120 | 90 | 90 | 90 | 90 |
| 1-906 | 120 | 100 | 100 | 100 | 100 |
| 1-907 | 120 | 90 | 90 | 90 | 90 |
| 1-913 | 120 | 90 | 90 | 90 | 90 |
| 1-915 | 120 | 90 | 90 | 90 | 90 |
| 1-916 | 120 | 90 | 90 | 90 | 90 |
| 1-917 | 120 | 90 | 90 | 90 | 90 |
| 1-960 | 120 | 80 | 70 | 70 | 80 |
| 1-962 | 120 | 100 | 100 | 100 | 90 |
| 1-963 | 120 | 90 | 90 | 90 | 90 |
| 1-964 | 120 | 90 | 100 | 100 | 90 |
| 1-965 | 120 | 100 | 100 | 80 | 80 |
| 1-967 | 120 | 90 | 100 | 90 | 90 |
| 1-968 | 120 | 90 | 90 | 90 | 90 |
| 1-969 | 120 | 100 | 80 | 100 | 90 |
| 1-970 | 120 | 100 | 100 | 100 | 100 |
| 1-971 | 120 | 100 | 100 | 100 | 100 |
| 1-972 | 120 | 100 | 100 | 100 | 100 |
| 1-973 | 120 | 100 | 80 | 100 | 100 |
| 1-974 | 120 | 100 | 80 | 90 | 90 |
| 1-975 | 120 | 100 | 80 | 90 | 90 |
| 1-977 | 120 | 100 | 100 | 100 | 90 |
| 1-978 | 120 | 100 | 80 | 90 | 90 |
| 1-980 | 120 | 100 | 80 | 100 | 90 |
| 1-981 | 120 | 80 | 50 | 60 | 70 |
| 1-983 | 120 | 70 | 90 | 90 | 90 |
| 1-985 | 120 | 90 | 70 | 100 | 90 |
| 1-986 | 120 | 90 | 80 | 90 | 90 |
| 1-988 | 120 | 90 | 100 | 100 | 90 |
| 1-990 | 120 | 90 | 80 | 90 | 80 |
| 1-991 | 120 | 90 | 100 | 100 | 90 |
| 1-992 | 120 | 100 | 100 | 90 | 100 |
| 1-993 | 120 | 100 | 100 | 100 | 100 |
| 1-994 | 120 | 90 | 60 | 100 | 90 |
| 1-996 | 120 | 90 | 80 | 80 | 90 |
| 1-997 | 120 | 90 | 80 | 90 | 90 |
| 1-1000 | 120 | 100 | 90 | 80 | 100 |
| 1-1002 | 120 | 100 | 100 | 100 | 100 |
| 1-1003 | 120 | 100 | 90 | 90 | 90 |

TABLE 3-continued

| No. | Concentration (g/10a) | Echinochloa crus-galli | Monochoria vaginalis | Lindernia pyxidaria | Scirpus juncoides |
|---|---|---|---|---|---|
| 1-1005 | 120 | 90 | 70 | 60 | 90 |
| 1-1006 | 120 | 70 | 60 | 70 | 90 |
| 1-1011 | 120 | 90 | 90 | 90 | 90 |
| 1-1012 | 120 | 90 | 100 | 100 | 100 |
| 1-1013 | 120 | 40 | 90 | 90 | 90 |
| 1-1014 | 120 | 90 | 100 | 90 | 90 |
| 1-1015 | 120 | 90 | 90 | 100 | 90 |
| 1-1016 | 120 | 90 | 60 | 90 | 80 |
| 1-1017 | 120 | 40 | 90 | 60 | 90 |
| 1-1018 | 120 | 90 | 90 | 100 | 90 |
| 1-1019 | 120 | 40 | 60 | 60 | 40 |
| 1-1020 | 120 | 50 | 40 | 80 | 40 |
| 1-1021 | 120 | 40 | 40 | 40 | 60 |
| 1-1022 | 120 | 90 | 100 | 100 | 90 |
| 1-1023 | 120 | 50 | 50 | 40 | 50 |
| 1-1026 | 120 | 100 | 100 | 100 | 90 |
| 1-1027 | 120 | 90 | 100 | 100 | 80 |
| 1-1028 | 120 | 80 | 90 | 80 | 40 |
| 1-1029 | 120 | 60 | 60 | 60 | 60 |
| 1-1030 | 120 | 90 | 100 | 100 | 90 |
| 1-1031 | 120 | 100 | 100 | 100 | 100 |
| 1-1032 | 120 | 80 | 90 | 90 | 90 |
| 1-1033 | 120 | 90 | 100 | 100 | 90 |
| 1-1034 | 120 | 100 | 100 | 100 | 90 |
| 1-1036 | 120 | 70 | 60 | 60 | 70 |
| 1-1037 | 120 | 90 | 60 | 70 | 90 |
| 1-1038 | 120 | 90 | 90 | 90 | 90 |
| 1-1039 | 120 | 90 | 80 | 90 | 90 |
| 1-1040 | 120 | 100 | 90 | 100 | 90 |
| 1-1041 | 120 | 100 | 90 | 90 | 90 |
| 1-1042 | 120 | 90 | 80 | 90 | 90 |
| 1-1043 | 120 | 100 | 100 | 100 | 90 |
| 1-1044 | 120 | 90 | 40 | 60 | 40 |
| 1-1045 | 120 | 100 | 80 | 90 | 90 |
| 1-1046 | 120 | 100 | 80 | 70 | 90 |
| 1-1047 | 120 | 90 | 80 | 100 | 90 |
| 1-1048 | 120 | 90 | 60 | 80 | 80 |
| 1-1049 | 120 | 90 | 80 | 90 | 90 |
| 1-1050 | 120 | 100 | 100 | 100 | 90 |
| 1-1051 | 120 | 80 | 80 | 60 | 100 |
| 1-1054 | 120 | 90 | 100 | 100 | 90 |
| 1-1055 | 120 | 60 | 100 | 100 | 90 |
| 1-1057 | 120 | 90 | 80 | 80 | 90 |
| 1-1058 | 120 | 90 | 70 | 80 | 90 |
| 1-1059 | 120 | 100 | 90 | 80 | 80 |
| 1-1064 | 120 | 90 | 90 | 90 | 90 |
| 1-1127 | 120 | 100 | 100 | 100 | 90 |

Test Example 2

Herbicidal Effect Test by Treatment During Growing Period in Paddy Rice Cultivation Wagner pots with an area of 1/10000 ares were filled with a paddy soil, and after adding water, a compound fertilizer (N:P:K=17:17:17) was mixed, followed by soil puddling. Then, *Echinochloa crus-galli*, broad leaf weeds (*Lindernia pyxidaria* and *Monochoria vaginalis*) and *Scirpus juncoides*, 30 seeds each, were sown in a depth of 0 to 1 cm. Water was poured immediately after seeding, and the water depth was kept at about 3 cm. The subsequent management was conducted in a glass greenhouse. Emulsions prepared using the compounds in Table 4 below according to Formulation Example 5 were diluted with water seven days after seeding, and a certain amount of the water-diluted agent solutions were dropped. The converted amount of the applied active ingredient corresponded to 120 g per 10 ares. The test was conducted in a double system per one agent solution concentration area, and the herbicidal rates (%) were determined by the equation (Math. 1) on 14 days after the treatment with the agents. The results are shown in Table 4. In this regard, a herbicidal rate of 80% or more is the maximum effect, and it has been confirmed that the effect is exhibited also in a test at a low concentration. The compound numbers in Table 4 are the same as those in Table 1 and Table 2 above.

TABLE 4

| No. | Concentration (g/10a) | Echinochloa crus-galli | Monochoria vaginalis | Lindernia pyxidaria | Scirpus juncoides |
|---|---|---|---|---|---|
| 1-28 | 120 | 100 | 100 | 80 | 90 |
| 1-29 | 120 | 100 | 90 | 80 | 90 |
| 1-31 | 120 | 50 | 80 | 60 | 70 |
| 1-32 | 120 | 90 | 90 | 80 | 90 |
| 1-33 | 120 | 60 | 60 | 60 | 80 |
| 1-37 | 120 | 40 | 40 | 40 | 0 |
| 1-41 | 120 | 90 | 80 | 90 | 60 |
| 1-46 | 120 | 40 | 40 | 40 | 60 |
| 1-47 | 120 | 40 | 40 | 40 | 70 |
| 1-63 | 120 | 80 | 90 | 80 | 90 |
| 1-68 | 120 | 40 | 80 | 70 | 80 |
| 1-69 | 120 | 60 | 60 | 40 | 60 |
| 1-78 | 120 | 40 | 60 | 40 | 80 |
| 1-81 | 120 | 80 | 80 | 60 | 90 |
| 1-83 | 120 | 40 | 40 | 40 | 60 |
| 1-84 | 120 | 40 | 40 | 40 | 70 |
| 1-97 | 120 | 90 | 60 | 80 | 90 |
| 1-98 | 120 | 80 | 60 | 60 | 90 |
| 1-100 | 120 | 90 | 100 | 90 | 90 |
| 1-101 | 120 | 90 | 90 | 90 | 90 |
| 1-102 | 120 | 90 | 90 | 60 | 90 |
| 1-103 | 120 | 90 | 80 | 60 | 80 |
| 1-105 | 120 | 90 | 90 | 90 | 90 |
| 1-106 | 120 | 90 | 90 | 90 | 90 |
| 1-109 | 120 | 90 | 90 | 70 | 90 |
| 1-110 | 120 | 100 | 100 | 80 | 80 |
| 1-112 | 120 | 90 | 80 | 80 | 90 |
| 1-113 | 120 | 90 | 80 | 60 | 90 |
| 1-115 | 120 | 90 | 80 | 80 | 90 |
| 1-116 | 120 | 90 | 80 | 60 | 90 |
| 1-120 | 120 | 90 | 80 | 80 | 90 |
| 1-124 | 120 | 90 | 70 | 60 | 80 |
| 1-130 | 120 | 100 | 90 | 90 | 80 |
| 1-133 | 120 | 60 | 80 | 60 | 80 |
| 1-134 | 120 | 80 | 80 | 40 | 80 |
| 1-135 | 120 | 80 | 60 | 40 | 90 |
| 1-136 | 120 | 90 | 70 | 60 | 90 |
| 1-137 | 120 | 90 | 60 | 40 | 80 |
| 1-138 | 120 | 90 | 80 | 80 | 80 |
| 1-142 | 120 | 100 | 100 | 90 | 90 |
| 1-143 | 120 | 90 | 80 | 70 | 90 |
| 1-144 | 120 | 90 | 80 | 50 | 90 |
| 1-145 | 120 | 90 | 80 | 60 | 80 |
| 1-146 | 120 | 100 | 90 | 70 | 90 |
| 1-148 | 120 | 90 | 80 | 60 | 90 |
| 1-149 | 120 | 100 | 90 | 90 | 90 |
| 1-155 | 120 | 100 | 60 | 60 | 80 |
| 1-156 | 120 | 80 | 100 | 100 | 90 |
| 1-162 | 120 | 90 | 80 | 70 | 80 |
| 1-166 | 120 | 100 | 90 | 90 | 90 |
| 1-167 | 120 | 90 | 90 | 90 | 90 |
| 1-180 | 120 | 70 | 90 | 80 | 90 |
| 1-181 | 120 | 50 | 90 | 80 | 90 |
| 1-182 | 120 | 40 | 60 | 60 | 70 |
| 1-183 | 120 | 80 | 100 | 100 | 100 |
| 1-186 | 120 | 50 | 80 | 80 | 80 |
| 1-187 | 120 | 40 | 80 | 70 | 70 |
| 1-189 | 120 | 60 | 80 | 80 | 80 |
| 1-191 | 120 | 90 | 80 | 80 | 90 |
| 1-192 | 120 | 40 | 80 | 80 | 60 |
| 1-193 | 120 | 60 | 80 | 80 | 70 |
| 1-194 | 120 | 40 | 60 | 60 | 60 |
| 1-195 | 120 | 80 | 40 | 40 | 80 |
| 1-198 | 120 | 40 | 90 | 90 | 40 |
| 1-199 | 120 | 90 | 80 | 80 | 80 |
| 1-200 | 120 | 60 | 90 | 90 | 80 |
| 1-201 | 120 | 40 | 70 | 70 | 40 |
| 1-202 | 120 | 40 | 60 | 60 | 40 |
| 1-203 | 120 | 90 | 90 | 90 | 90 |
| 1-204 | 120 | 80 | 80 | 80 | 80 |

TABLE 4-continued

| No. | Concentration (g/10a) | Echinochloa crus-galli | Monochoria vaginalis | Lindernia pyxidaria | Scirpus juncoides |
| --- | --- | --- | --- | --- | --- |
| 1-205 | 120 | 50 | 90 | 90 | 80 |
| 1-206 | 120 | 60 | 90 | 80 | 80 |
| 1-207 | 120 | 60 | 70 | 60 | 70 |
| 1-208 | 120 | 90 | 90 | 60 | 80 |
| 1-209 | 120 | 40 | 80 | 60 | 90 |
| 1-211 | 120 | 90 | 80 | 60 | 90 |
| 1-212 | 120 | 90 | 90 | 70 | 90 |
| 1-213 | 120 | 90 | 80 | 70 | 80 |
| 1-214 | 120 | 90 | 80 | 70 | 80 |
| 1-215 | 120 | 90 | 80 | 90 | 90 |
| 1-216 | 120 | 90 | 100 | 100 | 90 |
| 1-218 | 120 | 90 | 80 | 40 | 90 |
| 1-219 | 120 | 90 | 70 | 40 | 90 |
| 1-220 | 120 | 40 | 90 | 100 | 90 |
| 1-221 | 120 | 60 | 40 | 40 | 40 |
| 1-222 | 120 | 90 | 90 | 90 | 90 |
| 1-224 | 120 | 90 | 80 | 60 | 80 |
| 1-229 | 120 | 70 | 90 | 60 | 90 |
| 1-230 | 120 | 90 | 90 | 70 | 90 |
| 1-231 | 120 | 60 | 40 | 40 | 60 |
| 1-232 | 120 | 70 | 40 | 40 | 90 |
| 1-235 | 120 | 50 | 60 | 40 | 60 |
| 1-237 | 120 | 90 | 90 | 60 | 90 |
| 1-238 | 120 | 80 | 80 | 40 | 80 |
| 1-248 | 120 | 40 | 90 | 90 | 90 |
| 1-251 | 120 | 50 | 80 | 50 | 90 |
| 1-263 | 120 | 90 | 60 | 40 | 90 |
| 1-264 | 120 | 80 | 80 | 50 | 90 |
| 1-293 | 120 | 90 | 90 | 90 | 90 |
| 1-294 | 120 | 90 | 90 | 90 | 90 |
| 1-295 | 120 | 90 | 90 | 90 | 90 |
| 1-297 | 120 | 100 | 90 | 100 | 90 |
| 1-298 | 120 | 90 | 90 | 90 | 90 |
| 1-299 | 120 | 100 | 70 | 60 | 90 |
| 1-300 | 120 | 100 | 90 | 70 | 80 |
| 1-304 | 120 | 90 | 90 | 90 | 90 |
| 1-305 | 120 | 90 | 90 | 90 | 90 |
| 1-310 | 120 | 90 | 90 | 90 | 90 |
| 1-315 | 120 | 90 | 90 | 90 | 90 |
| 1-316 | 120 | 90 | 90 | 90 | 90 |
| 1-318 | 120 | 90 | 90 | 90 | 90 |
| 1-319 | 120 | 90 | 90 | 90 | 90 |
| 1-320 | 120 | 90 | 90 | 90 | 90 |
| 1-321 | 120 | 90 | 90 | 90 | 90 |
| 1-329 | 120 | 90 | 90 | 90 | 90 |
| 1-330 | 120 | 90 | 90 | 90 | 90 |
| 1-331 | 120 | 90 | 90 | 90 | 90 |
| 1-333 | 120 | 90 | 90 | 90 | 90 |
| 1-334 | 120 | 100 | 70 | 70 | 90 |
| 1-335 | 120 | 90 | 90 | 90 | 90 |
| 1-336 | 120 | 90 | 90 | 90 | 90 |
| 1-337 | 120 | 90 | 90 | 90 | 90 |
| 1-351 | 120 | 90 | 90 | 90 | 90 |
| 1-352 | 120 | 90 | 90 | 90 | 90 |
| 1-353 | 120 | 90 | 90 | 90 | 90 |
| 1-354 | 120 | 100 | 90 | 70 | 90 |
| 1-355 | 120 | 90 | 90 | 90 | 90 |
| 1-356 | 120 | 100 | 70 | 60 | 90 |
| 1-357 | 120 | 90 | 90 | 90 | 90 |
| 1-358 | 120 | 90 | 90 | 90 | 90 |
| 1-359 | 120 | 90 | 90 | 90 | 90 |
| 1-403 | 120 | 90 | 90 | 90 | 90 |
| 1-404 | 120 | 90 | 90 | 90 | 90 |
| 1-405 | 120 | 90 | 90 | 90 | 90 |
| 1-407 | 120 | 90 | 90 | 90 | 90 |
| 1-408 | 120 | 90 | 60 | 70 | 90 |
| 1-412 | 120 | 90 | 90 | 90 | 90 |
| 1-413 | 120 | 90 | 90 | 90 | 90 |
| 1-416 | 120 | 90 | 90 | 90 | 90 |
| 1-431 | 120 | 90 | 90 | 90 | 90 |
| 1-432 | 120 | 90 | 90 | 90 | 90 |
| 1-434 | 120 | 90 | 90 | 90 | 90 |
| 1-444 | 120 | 90 | 90 | 90 | 90 |
| 1-472 | 120 | 90 | 90 | 80 | 90 |
| 1-473 | 120 | 90 | 90 | 90 | 90 |
| 1-474 | 120 | 90 | 90 | 90 | 90 |
| 1-479 | 120 | 90 | 90 | 90 | 90 |
| 1-484 | 120 | 90 | 90 | 90 | 90 |
| 1-494 | 120 | 90 | 90 | 90 | 90 |
| 1-503 | 120 | 90 | 90 | 90 | 90 |
| 1-504 | 120 | 90 | 90 | 90 | 90 |
| 1-506 | 120 | 90 | 90 | 90 | 90 |
| 1-522 | 120 | 90 | 90 | 90 | 90 |
| 1-528 | 120 | 90 | 90 | 90 | 90 |
| 1-575 | 120 | 90 | 100 | 100 | 100 |
| 1-576 | 120 | 90 | 90 | 90 | 90 |
| 1-577 | 120 | 90 | 90 | 90 | 90 |
| 1-580 | 120 | 90 | 90 | 90 | 90 |
| 1-583 | 120 | 100 | 90 | 80 | 90 |
| 1-587 | 120 | 90 | 90 | 90 | 90 |
| 1-592 | 120 | 90 | 90 | 90 | 90 |
| 1-597 | 120 | 90 | 100 | 80 | 90 |
| 1-598 | 120 | 90 | 90 | 90 | 90 |
| 1-604 | 120 | 90 | 90 | 90 | 90 |
| 1-605 | 120 | 90 | 90 | 90 | 90 |
| 1-608 | 120 | 90 | 80 | 60 | 80 |
| 1-609 | 120 | 90 | 90 | 90 | 90 |
| 1-611 | 120 | 100 | 80 | 70 | 90 |
| 1-615 | 120 | 90 | 90 | 90 | 90 |
| 1-620 | 120 | 90 | 90 | 90 | 90 |
| 1-626 | 120 | 90 | 90 | 90 | 90 |
| 1-631 | 120 | 90 | 90 | 90 | 90 |
| 1-632 | 120 | 90 | 90 | 90 | 90 |
| 1-634 | 120 | 90 | 90 | 90 | 90 |
| 1-641 | 120 | 90 | 90 | 90 | 90 |
| 1-642 | 120 | 90 | 90 | 90 | 90 |
| 1-647 | 120 | 90 | 90 | 90 | 90 |
| 1-652 | 120 | 90 | 90 | 90 | 90 |
| 1-653 | 120 | 90 | 90 | 90 | 90 |
| 1-666 | 120 | 100 | 90 | 90 | 90 |
| 1-667 | 120 | 90 | 90 | 90 | 90 |
| 1-668 | 120 | 90 | 90 | 90 | 90 |
| 1-669 | 120 | 90 | 90 | 90 | 90 |
| 1-671 | 120 | 90 | 90 | 60 | 90 |
| 1-674 | 120 | 100 | 90 | 70 | 90 |
| 1-675 | 120 | 90 | 90 | 90 | 90 |
| 1-676 | 120 | 90 | 90 | 90 | 90 |
| 1-677 | 120 | 70 | 80 | 80 | 90 |
| 1-678 | 120 | 90 | 90 | 90 | 90 |
| 1-679 | 120 | 50 | 40 | 40 | 40 |
| 1-706 | 120 | 90 | 90 | 90 | 90 |
| 1-707 | 120 | 90 | 90 | 90 | 90 |
| 1-708 | 120 | 90 | 90 | 90 | 90 |
| 1-709 | 120 | 90 | 90 | 90 | 90 |
| 1-710 | 120 | 90 | 90 | 90 | 90 |
| 1-731 | 120 | 90 | 90 | 90 | 90 |
| 1-733 | 120 | 100 | 90 | 70 | 90 |
| 1-735 | 120 | 90 | 90 | 90 | 90 |
| 1-736 | 120 | 90 | 90 | 90 | 90 |
| 1-762 | 120 | 90 | 90 | 90 | 90 |
| 1-763 | 120 | 90 | 90 | 90 | 90 |
| 1-765 | 120 | 90 | 90 | 90 | 90 |
| 1-766 | 120 | 90 | 90 | 90 | 90 |
| 1-781 | 120 | 90 | 90 | 90 | 90 |
| 1-783 (TLC bottom) | 120 | 90 | 90 | 90 | 90 |
| 1-785 | 120 | 90 | 90 | 90 | 90 |
| 1-788 (TLC top) | 120 | 40 | 40 | 40 | 50 |
| 1-789 (TLC bottom) | 120 | 100 | 90 | 60 | 90 |
| 1-790 | 120 | 90 | 90 | 90 | 90 |
| 1-796 | 120 | 90 | 90 | 90 | 90 |
| 1-829 | 120 | 90 | 90 | 90 | 90 |
| 1-874 | 120 | 90 | 90 | 90 | 90 |
| 1-886 | 120 | 90 | 90 | 90 | 90 |
| 1-888 | 120 | 90 | 100 | 80 | 90 |
| 1-889 | 120 | 90 | 90 | 90 | 90 |
| 1-890 | 120 | 90 | 90 | 90 | 90 |
| 1-892 | 120 | 90 | 80 | 80 | 90 |

TABLE 4-continued

| No. | Concentration (g/10a) | Echinochloa crus-galli | Monochoria vaginalis | Lindernia pyxidaria | Scirpus juncoides |
|---|---|---|---|---|---|
| 1-893 | 120 | 90 | 90 | 90 | 90 |
| 1-894 | 120 | 90 | 70 | 70 | 80 |
| 1-895 | 120 | 90 | 80 | 70 | 90 |
| 1-899 | 120 | 90 | 90 | 90 | 90 |
| 1-900 | 120 | 90 | 90 | 90 | 90 |
| 1-906 | 120 | 90 | 100 | 100 | 100 |
| 1-907 | 120 | 90 | 90 | 90 | 90 |
| 1-913 | 120 | 90 | 90 | 90 | 90 |
| 1-915 | 120 | 90 | 90 | 90 | 90 |
| 1-916 | 120 | 90 | 90 | 90 | 90 |
| 1-917 | 120 | 90 | 90 | 90 | 90 |
| 1-960 | 120 | 70 | 70 | 70 | 70 |
| 1-962 | 120 | 90 | 80 | 60 | 80 |
| 1-963 | 120 | 90 | 90 | 90 | 90 |
| 1-964 | 120 | 90 | 90 | 90 | 90 |
| 1-965 | 120 | 100 | 80 | 50 | 80 |
| 1-967 | 120 | 90 | 90 | 100 | 80 |
| 1-968 | 120 | 90 | 90 | 90 | 90 |
| 1-969 | 120 | 100 | 90 | 60 | 90 |
| 1-970 | 120 | 100 | 90 | 70 | 90 |
| 1-971 | 120 | 100 | 90 | 80 | 90 |
| 1-972 | 120 | 100 | 100 | 80 | 90 |
| 1-973 | 120 | 100 | 90 | 60 | 90 |
| 1-974 | 120 | 100 | 90 | 90 | 90 |
| 1-975 | 120 | 100 | 80 | 70 | 80 |
| 1-977 | 120 | 100 | 90 | 80 | 90 |
| 1-978 | 120 | 100 | 60 | 50 | 60 |
| 1-980 | 120 | 100 | 80 | 80 | 80 |
| 1-981 | 120 | 90 | 40 | 50 | 40 |
| 1-983 | 120 | 40 | 80 | 80 | 80 |
| 1-985 | 120 | 90 | 60 | 60 | 60 |
| 1-986 | 120 | 90 | 70 | 40 | 90 |
| 1-988 | 120 | 90 | 100 | 100 | 90 |
| 1-990 | 120 | 100 | 80 | 100 | 80 |
| 1-991 | 120 | 90 | 80 | 70 | 90 |
| 1-992 | 120 | 90 | 90 | 50 | 80 |
| 1-993 | 120 | 90 | 60 | 50 | 90 |
| 1-994 | 120 | 90 | 80 | 60 | 80 |
| 1-996 | 120 | 70 | 80 | 70 | 90 |
| 1-997 | 120 | 90 | 90 | 70 | 90 |
| 1-1000 | 120 | 90 | 70 | 40 | 90 |
| 1-1002 | 120 | 90 | 80 | 60 | 80 |
| 1-1003 | 120 | 100 | 70 | 70 | 90 |
| 1-1005 | 120 | 90 | 90 | 70 | 90 |
| 1-1006 | 120 | 80 | 80 | 60 | 90 |
| 1-1011 | 120 | 40 | 90 | 90 | 90 |
| 1-1012 | 120 | 60 | 80 | 80 | 90 |
| 1-1014 | 120 | 90 | 80 | 80 | 90 |
| 1-1015 | 120 | 70 | 90 | 90 | 90 |
| 1-1016 | 120 | 40 | 80 | 70 | 60 |
| 1-1017 | 120 | 0 | 80 | 80 | 80 |
| 1-1018 | 120 | 40 | 80 | 80 | 80 |
| 1-1019 | 120 | 0 | 40 | 40 | 0 |
| 1-1020 | 120 | 60 | 40 | 40 | 40 |
| 1-1022 | 120 | 70 | 100 | 100 | 90 |
| 1-1023 | 120 | 40 | 40 | 40 | 40 |
| 1-1026 | 120 | 60 | 90 | 100 | 80 |
| 1-1027 | 120 | 40 | 40 | 40 | 40 |
| 1-1028 | 120 | 0 | 40 | 40 | 0 |
| 1-1030 | 120 | 90 | 90 | 90 | 90 |
| 1-1031 | 120 | 90 | 100 | 100 | 100 |
| 1-1032 | 120 | 40 | 40 | 40 | 40 |
| 1-1033 | 120 | 70 | 80 | 80 | 80 |
| 1-1034 | 120 | 90 | 80 | 80 | 90 |
| 1-1036 | 120 | 40 | 60 | 60 | 60 |
| 1-1037 | 120 | 90 | 50 | 60 | 60 |
| 1-1038 | 120 | 90 | 80 | 60 | 90 |
| 1-1039 | 120 | 100 | 80 | 70 | 80 |
| 1-1040 | 120 | 100 | 60 | 60 | 70 |
| 1-1041 | 120 | 90 | 70 | 70 | 70 |
| 1-1042 | 120 | 60 | 60 | 60 | 70 |
| 1-1043 | 120 | 90 | 100 | 100 | 90 |
| 1-1044 | 120 | 70 | 40 | 40 | 70 |
| 1-1045 | 120 | 90 | 90 | 60 | 90 |
| 1-1046 | 120 | 90 | 90 | 60 | 90 |
| 1-1047 | 120 | 80 | 80 | 90 | 80 |
| 1-1048 | 120 | 90 | 60 | 60 | 40 |
| 1-1049 | 120 | 80 | 70 | 60 | 70 |
| 1-1050 | 120 | 90 | 90 | 100 | 90 |
| 1-1051 | 120 | 90 | 80 | 40 | 90 |
| 1-1054 | 120 | 90 | 100 | 100 | 90 |
| 1-1055 | 120 | 80 | 60 | 40 | 80 |
| 1-1057 | 120 | 80 | 80 | 60 | 80 |
| 1-1058 | 120 | 90 | 90 | 80 | 80 |
| 1-1059 | 120 | 90 | 70 | 40 | 70 |
| 1-1064 | 120 | 70 | 80 | 50 | 90 |
| 1-1127 | 120 | 100 | 100 | 100 | 90 |

Test Example 3

Herbicidal Effect Test by Treatment of Dry Field Farming Soil

Pots with a size of 36 cm² were filled with a dry field farming soil (alluvium). The soil of the top layer of 1 cm and seeds of weeds, namely southern crabgrass, *Echinochloa crus-galli*, *Chenopodium album* and *Amaranthus viridis*, 20 seeds each, were evenly mixed, and the top layer was gently pressed. Emulsions prepared using the compounds in Table 5 below according to Formulation Example 5 were diluted with water one day after seeding, and the water-diluted agent solutions were sprayed to the soil surfaces at a ratio of 100 liters per 10 ares. The converted amount of the applied active ingredient corresponded to 120 g per 10 ares. The herbicidal effects were evaluated by the same standard as that in Test Example 1 on 14 days after the treatment with the agents. The results are shown in Table 5. In this regard, a herbicidal rate of 80% or more is the maximum effect, and it has been confirmed that the effect is exhibited also in a test at a low concentration. The compound numbers in Table 5 are the same as those in Table 1 and Table 2 above.

TABLE 5

| No. | Concentration (g/10a) | southern crabgrass | Echinochloa crus-galli | Chenopodium album | Amaranthus viridis |
|---|---|---|---|---|---|
| 1-28 | 120 | 80 | 90 | 100 | 100 |
| 1-29 | 120 | 70 | 70 | 40 | 40 |
| 1-33 | 120 | 70 | 90 | 40 | 0 |
| 1-37 | 120 | 40 | 70 | 40 | 0 |
| 1-41 | 120 | 90 | 90 | 50 | 0 |
| 1-63 | 120 | 90 | 90 | 40 | 40 |
| 1-83 | 120 | 40 | 50 | 40 | 40 |
| 1-97 | 120 | 90 | 90 | 0 | 0 |
| 1-98 | 120 | 90 | 90 | 0 | 0 |
| 1-100 | 120 | 100 | 100 | 100 | 100 |

TABLE 5-continued

| No. | Concentration (g/10a) | southern crabgrass | Echinochloa crus-galli | Chenopodium album | Amaranthus viridis |
|---|---|---|---|---|---|
| 1-101 | 120 | 90 | 90 | 90 | 90 |
| 1-102 | 120 | 90 | 90 | 80 | 80 |
| 1-103 | 120 | 100 | 100 | 100 | 100 |
| 1-105 | 120 | 90 | 60 | 50 | 70 |
| 1-106 | 120 | 90 | 90 | 90 | 90 |
| 1-109 | 120 | 90 | 90 | 60 | 60 |
| 1-110 | 120 | 90 | 90 | 80 | 80 |
| 1-112 | 120 | 90 | 90 | 80 | 60 |
| 1-113 | 120 | 90 | 90 | 100 | 80 |
| 1-115 | 120 | 90 | 90 | 100 | 100 |
| 1-116 | 120 | 90 | 90 | 50 | 80 |
| 1-120 | 120 | 90 | 90 | 50 | 50 |
| 1-124 | 120 | 80 | 100 | 50 | 40 |
| 1-130 | 120 | 70 | 90 | 50 | 40 |
| 1-136 | 120 | 100 | 100 | 60 | 100 |
| 1-137 | 120 | 50 | 70 | 40 | 40 |
| 1-138 | 120 | 90 | 90 | 0 | 0 |
| 1-142 | 120 | 90 | 100 | 90 | 70 |
| 1-143 | 120 | 40 | 50 | 0 | 60 |
| 1-144 | 120 | 80 | 70 | 0 | 0 |
| 1-145 | 120 | 80 | 90 | 40 | 40 |
| 1-146 | 120 | 100 | 100 | 90 | 90 |
| 1-148 | 120 | 100 | 100 | 80 | 80 |
| 1-149 | 120 | 90 | 90 | 40 | 40 |
| 1-156 | 120 | 80 | 80 | 60 | 60 |
| 1-166 | 120 | 90 | 90 | 60 | 60 |
| 1-180 | 120 | 80 | 80 | 30 | 30 |
| 1-183 | 120 | 90 | 90 | 60 | 50 |
| 1-203 | 120 | 90 | 60 | 40 | 40 |
| 1-208 | 120 | 50 | 100 | 40 | 40 |
| 1-211 | 120 | 90 | 90 | 0 | 0 |
| 1-212 | 120 | 90 | 90 | 0 | 0 |
| 1-213 | 120 | 100 | 100 | 100 | 100 |
| 1-214 | 120 | 70 | 80 | 90 | 90 |
| 1-215 | 120 | 50 | 50 | 40 | 40 |
| 1-216 | 120 | 70 | 60 | 0 | 40 |
| 1-218 | 120 | 40 | 80 | 40 | 40 |
| 1-219 | 120 | 80 | 90 | 40 | 90 |
| 1-221 | 120 | 50 | 70 | 40 | 50 |
| 1-222 | 120 | 100 | 100 | 100 | 100 |
| 1-224 | 120 | 100 | 100 | 90 | 100 |
| 1-229 | 120 | 60 | 40 | 40 | 60 |
| 1-230 | 120 | 100 | 100 | 60 | 60 |
| 1-237 | 120 | 50 | 50 | 40 | 80 |
| 1-248 | 120 | 80 | 70 | 60 | 50 |
| 1-251 | 120 | 80 | 100 | 80 | 80 |
| 1-293 | 120 | 90 | 90 | 90 | 90 |
| 1-294 | 120 | 90 | 90 | 90 | 90 |
| 1-295 | 120 | 90 | 90 | 90 | 90 |
| 1-297 | 120 | 90 | 100 | 90 | 90 |
| 1-298 | 120 | 90 | 90 | 90 | 90 |
| 1-299 | 120 | 80 | 90 | 40 | 70 |
| 1-300 | 120 | 100 | 90 | 60 | 80 |
| 1-304 | 120 | 90 | 90 | 90 | 90 |
| 1-305 | 120 | 90 | 90 | 90 | 90 |
| 1-310 | 120 | 90 | 90 | 90 | 90 |
| 1-315 | 120 | 90 | 90 | 90 | 90 |
| 1-316 | 120 | 90 | 90 | 90 | 90 |
| 1-318 | 120 | 90 | 90 | 90 | 90 |
| 1-319 | 120 | 90 | 90 | 90 | 90 |
| 1-320 | 120 | 90 | 90 | 90 | 90 |
| 1-321 | 120 | 90 | 90 | 90 | 90 |
| 1-329 | 120 | 90 | 90 | 90 | 90 |
| 1-330 | 120 | 90 | 90 | 90 | 90 |
| 1-331 | 120 | 90 | 90 | 90 | 90 |
| 1-333 | 120 | 90 | 90 | 90 | 90 |
| 1-334 | 120 | 70 | 90 | 40 | 50 |
| 1-335 | 120 | 90 | 90 | 90 | 90 |
| 1-336 | 120 | 90 | 90 | 90 | 90 |
| 1-337 | 120 | 90 | 90 | 90 | 90 |
| 1-351 | 120 | 90 | 90 | 90 | 90 |
| 1-352 | 120 | 90 | 90 | 90 | 90 |
| 1-353 | 120 | 90 | 90 | 90 | 90 |
| 1-354 | 120 | 80 | 90 | 90 | 90 |
| 1-355 | 120 | 90 | 90 | 90 | 90 |
| 1-356 | 120 | 90 | 90 | 60 | 90 |
| 1-357 | 120 | 90 | 90 | 90 | 90 |

TABLE 5-continued

| No. | Concentration (g/10a) | southern crabgrass | Echinochloa crus-galli | Chenopodium album | Amaranthus viridis |
|---|---|---|---|---|---|
| 1-358 | 120 | 90 | 90 | 90 | 90 |
| 1-359 | 120 | 90 | 90 | 90 | 90 |
| 1-403 | 120 | 90 | 90 | 90 | 90 |
| 1-404 | 120 | 90 | 90 | 90 | 90 |
| 1-405 | 120 | 90 | 90 | 90 | 90 |
| 1-407 | 120 | 90 | 90 | 90 | 90 |
| 1-408 | 120 | 100 | 100 | 60 | 80 |
| 1-412 | 120 | 90 | 90 | 90 | 90 |
| 1-413 | 120 | 90 | 90 | 90 | 90 |
| 1-416 | 120 | 90 | 90 | 90 | 90 |
| 1-431 | 120 | 90 | 90 | 90 | 90 |
| 1-432 | 120 | 90 | 90 | 90 | 90 |
| 1-434 | 120 | 90 | 90 | 90 | 90 |
| 1-444 | 120 | 90 | 90 | 90 | 90 |
| 1-472 | 120 | 70 | 90 | 50 | 0 |
| 1-473 | 120 | 90 | 90 | 90 | 90 |
| 1-474 | 120 | 90 | 90 | 90 | 90 |
| 1-479 | 120 | 90 | 90 | 90 | 90 |
| 1-484 | 120 | 90 | 90 | 90 | 90 |
| 1-494 | 120 | 90 | 90 | 90 | 90 |
| 1-503 | 120 | 90 | 90 | 90 | 90 |
| 1-504 | 120 | 90 | 90 | 90 | 90 |
| 1-506 | 120 | 90 | 90 | 90 | 90 |
| 1-522 | 120 | 90 | 90 | 90 | 90 |
| 1-528 | 120 | 90 | 90 | 90 | 90 |
| 1-575 | 120 | 90 | 90 | 40 | 40 |
| 1-576 | 120 | 90 | 90 | 90 | 90 |
| 1-577 | 120 | 90 | 90 | 90 | 90 |
| 1-580 | 120 | 90 | 90 | 90 | 90 |
| 1-583 | 120 | 90 | 100 | 50 | 60 |
| 1-587 | 120 | 90 | 90 | 90 | 90 |
| 1-592 | 120 | 90 | 90 | 90 | 90 |
| 1-597 | 120 | 90 | 90 | 0 | 0 |
| 1-598 | 120 | 90 | 90 | 90 | 90 |
| 1-604 | 120 | 90 | 90 | 90 | 90 |
| 1-605 | 120 | 90 | 90 | 90 | 90 |
| 1-609 | 120 | 90 | 90 | 90 | 90 |
| 1-611 | 120 | 70 | 70 | 40 | 40 |
| 1-615 | 120 | 90 | 90 | 90 | 90 |
| 1-620 | 120 | 90 | 90 | 90 | 90 |
| 1-626 | 120 | 90 | 90 | 90 | 90 |
| 1-631 | 120 | 90 | 90 | 90 | 90 |
| 1-641 | 120 | 90 | 90 | 90 | 90 |
| 1-642 | 120 | 90 | 90 | 90 | 90 |
| 1-647 | 120 | 90 | 90 | 90 | 90 |
| 1-652 | 120 | 90 | 90 | 90 | 90 |
| 1-653 | 120 | 90 | 90 | 90 | 90 |
| 1-666 | 120 | 100 | 90 | 40 | 0 |
| 1-667 | 120 | 80 | 90 | 90 | 80 |
| 1-668 | 120 | 90 | 90 | 90 | 90 |
| 1-669 | 120 | 90 | 90 | 90 | 90 |
| 1-674 | 120 | 50 | 80 | 40 | 40 |
| 1-675 | 120 | 90 | 90 | 90 | 90 |
| 1-676 | 120 | 90 | 90 | 90 | 90 |
| 1-678 | 120 | 90 | 90 | 90 | 90 |
| 1-706 | 120 | 90 | 90 | 90 | 90 |
| 1-707 | 120 | 90 | 90 | 90 | 90 |
| 1-708 | 120 | 90 | 90 | 90 | 90 |
| 1-709 | 120 | 90 | 90 | 90 | 90 |
| 1-710 | 120 | 90 | 90 | 90 | 90 |
| 1-731 | 120 | 90 | 90 | 90 | 90 |
| 1-733 | 120 | 100 | 100 | 60 | 80 |
| 1-735 | 120 | 90 | 90 | 90 | 90 |
| 1-736 | 120 | 90 | 90 | 90 | 90 |
| 1-762 | 120 | 90 | 90 | 90 | 90 |
| 1-763 | 120 | 90 | 90 | 90 | 90 |
| 1-765 | 120 | 90 | 90 | 90 | 90 |
| 1-766 | 120 | 90 | 90 | 90 | 90 |
| 1-781 | 120 | 90 | 90 | 90 | 90 |
| 1-783 (TLC bottom) | 120 | 90 | 90 | 90 | 90 |
| 1-785 | 120 | 90 | 90 | 90 | 90 |
| 1-789 (TLC bottom) | 120 | 60 | 90 | 80 | 70 |
| 1-790 | 120 | 90 | 90 | 90 | 90 |
| 1-796 | 120 | 90 | 90 | 90 | 90 |
| 1-829 | 120 | 90 | 90 | 90 | 90 |

TABLE 5-continued

| No. | Concentration (g/10a) | southern crabgrass | Echinochloa crus-galli | Chenopodium album | Amaranthus viridis |
|---|---|---|---|---|---|
| 1-874 | 120 | 90 | 90 | 90 | 90 |
| 1-886 | 120 | 90 | 90 | 90 | 90 |
| 1-888 | 120 | 70 | 90 | 60 | 40 |
| 1-889 | 120 | 90 | 90 | 90 | 90 |
| 1-890 | 120 | 90 | 90 | 90 | 90 |
| 1-892 | 120 | 90 | 90 | 80 | 90 |
| 1-893 | 120 | 90 | 90 | 90 | 90 |
| 1-894 | 120 | 90 | 90 | 60 | 70 |
| 1-895 | 120 | 100 | 100 | 50 | 80 |
| 1-899 | 120 | 90 | 90 | 90 | 90 |
| 1-900 | 120 | 90 | 90 | 90 | 90 |
| 1-906 | 120 | 90 | 100 | 70 | 50 |
| 1-907 | 120 | 90 | 90 | 90 | 90 |
| 1-913 | 120 | 90 | 90 | 90 | 90 |
| 1-915 | 120 | 90 | 90 | 90 | 90 |
| 1-916 | 120 | 90 | 90 | 90 | 90 |
| 1-917 | 120 | 90 | 90 | 90 | 90 |
| 1-960 | 120 | 80 | 100 | 0 | 0 |
| 1-962 | 120 | 90 | 90 | 70 | 80 |
| 1-963 | 120 | 90 | 90 | 90 | 90 |
| 1-964 | 120 | 90 | 90 | 90 | 90 |
| 1-965 | 120 | 100 | 100 | 100 | 100 |
| 1-967 | 120 | 90 | 50 | 40 | 80 |
| 1-968 | 120 | 90 | 90 | 90 | 90 |
| 1-969 | 120 | 80 | 90 | 40 | 40 |
| 1-970 | 120 | 90 | 90 | 40 | 60 |
| 1-971 | 120 | 80 | 90 | 60 | 80 |
| 1-972 | 120 | 90 | 90 | 100 | 100 |
| 1-973 | 120 | 100 | 100 | 90 | 90 |
| 1-974 | 120 | 90 | 90 | 100 | 100 |
| 1-975 | 120 | 90 | 80 | 90 | 90 |
| 1-977 | 120 | 80 | 80 | 50 | 70 |
| 1-978 | 120 | 90 | 80 | 90 | 90 |
| 1-980 | 120 | 60 | 40 | 40 | 40 |
| 1-985 | 120 | 70 | 70 | 80 | 80 |
| 1-986 | 120 | 80 | 100 | 60 | 60 |
| 1-990 | 120 | 50 | 50 | 50 | 0 |
| 1-992 | 120 | 90 | 90 | 40 | 40 |
| 1-993 | 120 | 80 | 90 | 40 | 40 |
| 1-997 | 120 | 90 | 90 | 50 | 50 |
| 1-1000 | 120 | 80 | 60 | 40 | 40 |
| 1-1005 | 120 | 40 | 60 | 40 | 40 |
| 1-1006 | 120 | 60 | 80 | 60 | 60 |
| 1-1011 | 120 | 80 | 90 | 40 | 40 |
| 1-1014 | 120 | 70 | 90 | 40 | 40 |
| 1-1038 | 120 | 90 | 90 | 0 | 0 |
| 1-1039 | 120 | 90 | 90 | 0 | 0 |
| 1-1040 | 120 | 100 | 100 | 80 | 100 |
| 1-1041 | 120 | 80 | 70 | 50 | 50 |
| 1-1045 | 120 | 50 | 90 | 40 | 40 |
| 1-1048 | 120 | 0 | 40 | 40 | 40 |
| 1-1049 | 120 | 80 | 90 | 50 | 50 |
| 1-1050 | 120 | 90 | 100 | 90 | 90 |
| 1-1051 | 120 | 80 | 80 | 60 | 80 |
| 1-1064 | 120 | 60 | 100 | 80 | 80 |
| 1-1127 | 120 | 70 | 90 | 60 | 40 |

Test Example 4

Herbicidal Effect Test by Treatment of Leave and Stem in Dry Field Farming

Pots with a size of 36 cm² were filled with a dry field farming soil (alluvium). The soil of the top layer of 1 cm and seeds of weeds, namely southern crabgrass, *Echinochloa crus-galli*, *Chenopodium album* and *Amaranthus viridis*, 20 seeds each, were evenly mixed, and the top layer was gently pressed. Emulsions prepared using the compounds in Table 6 below according to Formulation Example 5 were diluted with water seven days after seeding, and the water-diluted agent solutions were sprayed to the soil surfaces at a ratio of 100 liters per 10 ares. The converted amount of the applied active ingredient corresponded to 120 g per 10 ares. The herbicidal effects were evaluated by the same standard as that in Test Example 1 on 14 days after the treatment with the agents. The results are shown in Table 6. In this regard, a herbicidal rate of 80% or more is the maximum effect, and it has been confirmed that the effect is exhibited also in a test at a low concentration. The compound numbers in Table 6 are the same as those in Table 1 and Table 2 above.

TABLE 6

| No. | Concentration (g/10a) | southern crabgrass | Echinochloa crus-galli | Chenopodium album | Amaranthus viridis |
|---|---|---|---|---|---|
| 1-28 | 120 | 50 | 90 | 40 | 80 |
| 1-29 | 120 | 40 | 60 | 0 | 60 |
| 1-32 | 120 | 40 | 0 | 60 | 40 |
| 1-33 | 120 | 40 | 90 | 40 | 0 |
| 1-37 | 120 | 40 | 90 | 80 | 40 |
| 1-41 | 120 | 90 | 90 | 90 | 60 |
| 1-63 | 120 | 60 | 90 | 60 | 40 |
| 1-81 | 120 | 80 | 90 | 0 | 0 |
| 1-97 | 120 | 90 | 90 | 40 | 40 |
| 1-100 | 120 | 90 | 90 | 90 | 30 |
| 1-101 | 120 | 90 | 90 | 40 | 40 |
| 1-102 | 120 | 80 | 90 | 0 | 40 |
| 1-103 | 120 | 90 | 90 | 40 | 90 |
| 1-105 | 120 | 50 | 90 | 40 | 50 |
| 1-106 | 120 | 90 | 90 | 40 | 40 |
| 1-109 | 120 | 80 | 90 | 50 | 70 |
| 1-110 | 120 | 90 | 90 | 50 | 60 |
| 1-112 | 120 | 50 | 90 | 0 | 40 |
| 1-113 | 120 | 60 | 80 | 40 | 60 |
| 1-115 | 120 | 40 | 60 | 40 | 40 |
| 1-116 | 120 | 40 | 80 | 50 | 60 |
| 1-120 | 120 | 80 | 90 | 50 | 60 |
| 1-124 | 120 | 60 | 70 | 40 | 40 |
| 1-130 | 120 | 60 | 60 | 40 | 50 |
| 1-133 | 120 | 40 | 90 | 40 | 0 |
| 1-134 | 120 | 60 | 90 | 40 | 50 |
| 1-136 | 120 | 70 | 70 | 60 | 60 |
| 1-137 | 120 | 0 | 80 | 0 | 80 |
| 1-138 | 120 | 80 | 80 | 0 | 40 |
| 1-142 | 120 | 80 | 90 | 40 | 60 |
| 1-144 | 120 | 90 | 90 | 0 | 50 |
| 1-145 | 120 | 50 | 90 | 40 | 0 |
| 1-146 | 120 | 40 | 80 | 40 | 50 |
| 1-148 | 120 | 80 | 90 | 40 | 40 |
| 1-149 | 120 | 90 | 90 | 40 | 40 |
| 1-162 | 120 | 60 | 90 | 60 | 50 |
| 1-180 | 120 | 50 | 50 | 40 | 0 |
| 1-183 | 120 | 50 | 90 | 50 | 40 |
| 1-191 | 120 | 40 | 90 | 40 | 80 |
| 1-208 | 120 | 0 | 90 | 40 | 40 |
| 1-211 | 120 | 60 | 90 | 50 | 40 |
| 1-212 | 120 | 90 | 90 | 60 | 80 |
| 1-213 | 120 | 90 | 90 | 50 | 40 |
| 1-214 | 120 | 50 | 60 | 50 | 40 |
| 1-215 | 120 | 50 | 40 | 40 | 50 |
| 1-218 | 120 | 40 | 90 | 40 | 60 |
| 1-219 | 120 | 60 | 90 | 0 | 40 |
| 1-222 | 120 | 80 | 70 | 50 | 40 |
| 1-230 | 120 | 80 | 80 | 40 | 40 |
| 1-248 | 120 | 40 | 80 | 0 | 40 |
| 1-293 | 120 | 90 | 90 | 40 | 40 |
| 1-294 | 120 | 90 | 90 | 40 | 40 |
| 1-295 | 120 | 90 | 90 | 40 | 40 |
| 1-297 | 120 | 60 | 80 | 40 | 40 |
| 1-298 | 120 | 90 | 90 | 40 | 40 |
| 1-299 | 120 | 80 | 90 | 90 | 40 |
| 1-300 | 120 | 90 | 90 | 60 | 70 |
| 1-304 | 120 | 90 | 90 | 40 | 40 |
| 1-305 | 120 | 90 | 90 | 40 | 40 |
| 1-310 | 120 | 90 | 90 | 40 | 40 |
| 1-315 | 120 | 90 | 90 | 40 | 40 |
| 1-316 | 120 | 90 | 90 | 40 | 40 |
| 1-318 | 120 | 90 | 90 | 40 | 40 |
| 1-319 | 120 | 90 | 90 | 40 | 40 |
| 1-320 | 120 | 90 | 90 | 40 | 40 |
| 1-321 | 120 | 90 | 90 | 40 | 40 |
| 1-329 | 120 | 90 | 90 | 40 | 40 |
| 1-330 | 120 | 90 | 90 | 40 | 40 |
| 1-331 | 120 | 90 | 90 | 40 | 40 |
| 1-333 | 120 | 90 | 90 | 40 | 40 |
| 1-334 | 120 | 90 | 90 | 60 | 60 |
| 1-335 | 120 | 90 | 90 | 40 | 40 |
| 1-336 | 120 | 90 | 90 | 40 | 40 |
| 1-337 | 120 | 90 | 90 | 40 | 40 |
| 1-351 | 120 | 90 | 90 | 40 | 40 |
| 1-352 | 120 | 90 | 90 | 40 | 40 |
| 1-353 | 120 | 90 | 90 | 40 | 40 |

TABLE 6-continued

| No. | Concentration (g/10a) | southern crabgrass | Echinochloa crus-galli | Chenopodium album | Amaranthus viridis |
|---|---|---|---|---|---|
| 1-354 | 120 | 60 | 80 | 40 | 40 |
| 1-355 | 120 | 90 | 90 | 40 | 40 |
| 1-356 | 120 | 80 | 90 | 60 | 60 |
| 1-357 | 120 | 90 | 90 | 40 | 40 |
| 1-358 | 120 | 90 | 90 | 40 | 40 |
| 1-359 | 120 | 90 | 90 | 40 | 40 |
| 1-403 | 120 | 90 | 90 | 40 | 40 |
| 1-404 | 120 | 90 | 90 | 40 | 40 |
| 1-405 | 120 | 90 | 90 | 40 | 40 |
| 1-407 | 120 | 90 | 90 | 40 | 40 |
| 1-408 | 120 | 90 | 90 | 70 | 40 |
| 1-412 | 120 | 90 | 90 | 40 | 40 |
| 1-413 | 120 | 90 | 90 | 40 | 40 |
| 1-416 | 120 | 90 | 90 | 40 | 40 |
| 1-431 | 120 | 90 | 90 | 40 | 40 |
| 1-432 | 120 | 90 | 90 | 40 | 40 |
| 1-434 | 120 | 90 | 90 | 40 | 40 |
| 1-444 | 120 | 90 | 90 | 40 | 40 |
| 1-473 | 120 | 90 | 90 | 40 | 40 |
| 1-474 | 120 | 90 | 90 | 40 | 40 |
| 1-479 | 120 | 90 | 90 | 40 | 40 |
| 1-484 | 120 | 90 | 90 | 40 | 40 |
| 1-494 | 120 | 90 | 90 | 40 | 40 |
| 1-503 | 120 | 90 | 90 | 40 | 40 |
| 1-504 | 120 | 90 | 90 | 40 | 40 |
| 1-506 | 120 | 90 | 90 | 40 | 40 |
| 1-522 | 120 | 90 | 90 | 40 | 40 |
| 1-528 | 120 | 90 | 90 | 40 | 40 |
| 1-575 | 120 | 90 | 90 | 90 | 30 |
| 1-576 | 120 | 90 | 90 | 40 | 40 |
| 1-577 | 120 | 90 | 90 | 40 | 40 |
| 1-580 | 120 | 90 | 90 | 40 | 40 |
| 1-583 | 120 | 60 | 80 | 50 | 50 |
| 1-587 | 120 | 90 | 90 | 40 | 40 |
| 1-592 | 120 | 90 | 90 | 40 | 40 |
| 1-597 | 120 | 50 | 40 | 40 | 40 |
| 1-598 | 120 | 90 | 90 | 40 | 40 |
| 1-604 | 120 | 90 | 90 | 40 | 40 |
| 1-605 | 120 | 90 | 90 | 40 | 40 |
| 1-609 | 120 | 90 | 90 | 40 | 40 |
| 1-611 | 120 | 70 | 80 | 50 | 60 |
| 1-615 | 120 | 90 | 90 | 40 | 40 |
| 1-620 | 120 | 90 | 90 | 40 | 40 |
| 1-626 | 120 | 90 | 90 | 40 | 40 |
| 1-632 | 120 | 90 | 90 | 40 | 40 |
| 1-642 | 120 | 90 | 90 | 40 | 40 |
| 1-647 | 120 | 90 | 90 | 40 | 40 |
| 1-652 | 120 | 90 | 90 | 40 | 40 |
| 1-653 | 120 | 90 | 90 | 40 | 40 |
| 1-666 | 120 | 70 | 90 | 50 | 40 |
| 1-668 | 120 | 90 | 90 | 40 | 40 |
| 1-669 | 120 | 90 | 90 | 40 | 40 |
| 1-674 | 120 | 80 | 70 | 50 | 60 |
| 1-675 | 120 | 90 | 90 | 40 | 40 |
| 1-676 | 120 | 90 | 90 | 40 | 40 |
| 1-678 | 120 | 90 | 90 | 40 | 40 |
| 1-706 | 120 | 90 | 90 | 40 | 40 |
| 1-707 | 120 | 90 | 90 | 40 | 40 |
| 1-708 | 120 | 90 | 90 | 40 | 40 |
| 1-709 | 120 | 90 | 90 | 40 | 40 |
| 1-710 | 120 | 90 | 90 | 40 | 40 |
| 1-731 | 120 | 90 | 90 | 40 | 40 |
| 1-733 | 120 | 80 | 90 | 60 | 60 |
| 1-735 | 120 | 90 | 90 | 40 | 40 |
| 1-736 | 120 | 90 | 90 | 40 | 40 |
| 1-762 | 120 | 90 | 90 | 40 | 40 |
| 1-763 | 120 | 90 | 90 | 40 | 40 |
| 1-765 | 120 | 90 | 90 | 40 | 40 |
| 1-766 | 120 | 90 | 90 | 40 | 40 |
| 1-781 | 120 | 90 | 90 | 40 | 40 |
| 1-783 (TLC bottom) | 120 | 90 | 90 | 40 | 40 |
| 1-785 | 120 | 90 | 90 | 40 | 40 |
| 1-789 (TLC bottom) | 120 | 50 | 50 | 40 | 60 |
| 1-790 | 120 | 90 | 90 | 40 | 40 |
| 1-796 | 120 | 90 | 90 | 40 | 40 |

TABLE 6-continued

| No. | Concentration (g/10a) | southern crabgrass | Echinochloa crus-galli | Chenopodium album | Amaranthus viridis |
|---|---|---|---|---|---|
| 1-829 | 120 | 90 | 90 | 40 | 40 |
| 1-874 | 120 | 90 | 90 | 40 | 40 |
| 1-886 | 120 | 90 | 90 | 40 | 40 |
| 1-888 | 120 | 40 | 80 | 40 | 40 |
| 1-889 | 120 | 90 | 90 | 40 | 40 |
| 1-890 | 120 | 90 | 90 | 40 | 40 |
| 1-892 | 120 | 40 | 50 | 40 | 40 |
| 1-893 | 120 | 90 | 90 | 40 | 40 |
| 1-894 | 120 | 90 | 90 | 60 | 60 |
| 1-895 | 120 | 80 | 80 | 60 | 50 |
| 1-899 | 120 | 90 | 90 | 40 | 40 |
| 1-900 | 120 | 90 | 90 | 40 | 40 |
| 1-906 | 120 | 50 | 90 | 50 | 100 |
| 1-907 | 120 | 90 | 90 | 40 | 40 |
| 1-913 | 120 | 90 | 90 | 40 | 40 |
| 1-915 | 120 | 90 | 90 | 40 | 40 |
| 1-916 | 120 | 90 | 90 | 40 | 40 |
| 1-917 | 120 | 90 | 90 | 40 | 40 |
| 1-962 | 120 | 60 | 90 | 50 | 40 |
| 1-963 | 120 | 90 | 90 | 40 | 40 |
| 1-964 | 120 | 60 | 90 | 0 | 40 |
| 1-965 | 120 | 90 | 90 | 40 | 90 |
| 1-967 | 120 | 0 | 60 | 40 | 40 |
| 1-968 | 120 | 90 | 90 | 40 | 40 |
| 1-970 | 120 | 70 | 90 | 40 | 60 |
| 1-971 | 120 | 90 | 90 | 50 | 40 |
| 1-973 | 120 | 80 | 90 | 0 | 40 |
| 1-974 | 120 | 50 | 90 | 40 | 40 |
| 1-975 | 120 | 0 | 50 | 40 | 50 |
| 1-977 | 120 | 80 | 90 | 80 | 60 |
| 1-978 | 120 | 50 | 60 | 40 | 40 |
| 1-980 | 120 | 40 | 60 | 40 | 40 |
| 1-983 | 120 | 40 | 60 | 0 | 40 |
| 1-985 | 120 | 60 | 90 | 60 | 60 |
| 1-986 | 120 | 90 | 90 | 40 | 60 |
| 1-990 | 120 | 0 | 60 | 40 | 50 |
| 1-992 | 120 | 50 | 90 | 40 | 40 |
| 1-993 | 120 | 40 | 60 | 40 | 40 |
| 1-997 | 120 | 40 | 70 | 0 | 40 |
| 1-1000 | 120 | 40 | 60 | 0 | 40 |
| 1-1002 | 120 | 60 | 90 | 70 | 50 |
| 1-1003 | 120 | 40 | 60 | 0 | 40 |
| 1-1005 | 120 | 40 | 60 | 40 | 40 |
| 1-1006 | 120 | 40 | 40 | 40 | 40 |
| 1-1014 | 120 | 40 | 70 | 50 | 40 |
| 1-1030 | 120 | 40 | 90 | 40 | 40 |
| 1-1038 | 120 | 60 | 90 | 40 | 40 |
| 1-1039 | 120 | 90 | 90 | 40 | 40 |
| 1-1040 | 120 | 90 | 90 | 40 | 50 |
| 1-1041 | 120 | 50 | 40 | 40 | 60 |
| 1-1042 | 120 | 50 | 0 | 40 | 40 |
| 1-1045 | 120 | 40 | 90 | 0 | 60 |
| 1-1046 | 120 | 60 | 90 | 0 | 90 |
| 1-1050 | 120 | 40 | 50 | 50 | 40 |
| 1-1127 | 120 | 40 | 90 | 40 | 40 |

INDUSTRIAL APPLICABILITY

According to the invention, novel isoxazolin-5-one derivatives having an excellent herbicidal activity and herbicides containing the isoxazolin-5-one derivatives can be provided.

Although the invention has been explained in detail referring to specific embodiments, it is obvious to one skilled in the art that various changes and modifications can be made without departing from the spirit and the scope of the invention.

The application is based on a Japanese patent application filed on Jan. 20, 2017 (patent application No. 2017-008553), which is hereby incorporated by reference.

The invention claimed is:

1. An isoxazolin-5-one derivative of formula (1):

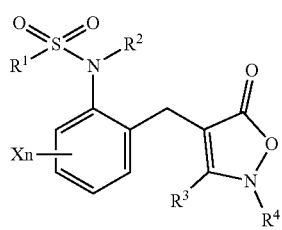

(1)

wherein,

R¹ is a C1-C6 haloalkyl group;

R² is a hydrogen atom,
- a C1-C6 alkyl group,
- a C1-C6 haloalkyl group,
- a C2-C6 alkenyl group,
- a C2-C6 alkynyl group,
- a C1-C6 alkoxy C1-C6 alkyl group,
- a C1-C6 haloalkoxy C1-C6 alkyl group,
- a C1-C6 alkoxy C1-C6 alkoxy C1-C6 alkyl group,
- a C1-C6 alkylthio C1-C6 alkyl group,
- a C1-C6 alkylcarbonyl C1-C6 alkyl group,
- a C7-C11 aralkyl group which may be monosubstituted or polysubstituted with a halogen atom, a C1-C6 alkyl group or a C1-C6 alkoxy group,
- a phenoxy C1-C6 alkyl group,
- a C7-C11 aralkyloxy C1-C6 alkyl group,
- a phenylcarbonyl C1-C6 alkyl group,
- a C1-C6 alkylcarbonyl group,
- a C1-C6 haloalkylcarbonyl group,
- a C2-C6 alkenylcarbonyl group,
- a C2-C6 alkynylcarbonyl group,
- a C3-C6 cycloalkylcarbonyl group,
- a C3-C6 cycloalkyl C1-C6 alkylcarbonyl group,
- a C1-C6 alkoxy C1-C6 alkylcarbonyl group,
- a C1-C6 haloalkoxy C1-C6 alkylcarbonyl group,
- a C1-C6 alkoxy C1-C6 alkoxy C1-C6 alkylcarbonyl group,
- a C1-C6 alkylthio C1-C6 alkylcarbonyl group,
- a C1-C6 haloalkylthio C1-C6 alkylcarbonyl group,
- a benzoyl group which may be monosubstituted or polysubstituted with a halogen atom or a C1-C6 alkyl group,
- a C7-C11 aralkylcarbonyl group which may be monosubstituted or polysubstituted with a halogen atom or a C1-C6 alkyl group,
- a heterocyclic carbonyl group which may be monosubstituted or polysubstituted with a halogen atom or a C1-C6 alkyl group,
- a heterocyclic C1-C6 alkylcarbonyl group which may be monosubstituted or polysubstituted with a halogen atom or a C1-C6 alkyl group,
- a C1-C6 alkoxycarbonyl group,
- a C1-C6 haloalkoxycarbonyl group,
- a C2-C6 alkenyloxycarbonyl group,
- a C2-C6 alkynyloxycarbonyl group,
- a C3-C6 cycloalkyloxycarbonyl group,
- a C3-C6 cycloalkyl C1-C6 alkoxycarbonyl group,
- a C1-C6 alkoxy C1-C6 alkoxycarbonyl group,
- a C1-C6 haloalkoxy C1-C6 alkoxycarbonyl group,
- a C1-C6 alkoxy C1-C6 alkoxy C1-C6 alkoxycarbonyl group,
- a C1-C6 alkylthio C1-C6 alkoxycarbonyl group,
- a C1-C6 haloalkylthio C1-C6 alkoxycarbonyl group,
- a phenoxycarbonyl group which may be monosubstituted or polysubstituted with a halogen atom or a C1-C6 alkyl group,
- a C7-C11 aralkyloxycarbonyl group which may be monosubstituted or polysubstituted with a halogen atom or a C1-C6 alkyl group,
- a phenoxy C1-C6 alkoxycarbonyl group which may be monosubstituted or polysubstituted with a halogen atom or a C1-C6 alkyl group,
- a heterocyclic oxycarbonyl group which may be monosubstituted or polysubstituted with a halogen atom or a C1-C6 alkyl group,
- a heterocyclic C1-C6 alkoxycarbonyl group which may be monosubstituted or polysubstituted with a halogen atom or a C1-C6 alkyl group,
- a C1-C6 alkylthiocarbonyl group,
- a C1-C6 haloalkylthiocarbonyl group,
- a C1-C6 alkylaminocarbonyl group,
- a C1-C6 haloalkylaminocarbonyl group,
- a di-C1-C6 alkylaminocarbonyl group wherein the di-C1-C6 alkyl groups may be same or different,
- a C1-C6 alkylsulfonyl group,
- a C1-C6 haloalkylsulfonyl group,
- a C2-C6 alkenylsulfonyl group,
- a C2-C6 alkynylsulfonyl group,
- a C3-C6 cycloalkylsulfonyl group,
- a C3-C6 cycloalkyl C1-C6 alkylsulfonyl group,
- a C1-C6 alkoxy C1-C6 alkylsulfonyl group,
- a phenylsulfonyl group which may be monosubstituted or polysubstituted with a halogen atom or a C1-C6 alkyl group,
- a C7-C11 aralkylsulfonyl group which may be monosubstituted or polysubstituted with a halogen atom or a C1-C6 alkyl group,
- a C1-C6 alkylaminosulfonyl group,
- or a di-C1-C6 alkylaminosulfonyl group wherein the di-C1-C6 alkyl groups may be same or different;

R³ is a hydrogen atom,
- a halogen atom,
- a C1-C6 alkyl group,
- a C1-C6 haloalkyl group,
- a C3-C6 cycloalkyl group,
- a phenyl group which may be monosubstituted or polysubstituted with a halogen atom or a C1-C6 alkyl group,
- an amino group,
- a C1-C6 alkylamino group,
- or a di-C1-C6 alkylamino group wherein the di-C1-C6 alkyl groups may be same or different;

R⁴ is a hydrogen atom,
- a C1-C15 alkyl group,
- a C1-C15 haloalkyl group,
- a C2-C6 alkenyl group,
- a C2-C6 haloalkenyl group,
- a C2-C6 alkynyl group,
- a C2-C6 haloalkynyl group,
- a C3-C6 cycloalkyl group,
- a C3-C6 cycloalkyl C1-C6 alkyl group,
- a C1-C6 alkoxy C1-C6 alkyl group,
- a C1-C6 haloalkoxy C1-C6 alkyl group,
- a C1-C6 alkoxy C1-C6 alkoxy C1-C6 alkyl group,
- a C1-C6 alkylthio C1-C6 alkyl group,
- a C1-C6 haloalkylthio C1-C6 alkyl group,
- a C1-C6 alkylsulfinyl C1-C6 alkyl group,
- a C1-C6 alkylsulfonyl C1-C6 alkyl group,
- a C1-C6 alkylamino C1-C6 alkyl group,
- a di-C1-C6 alkylamino C1-C6 alkyl group wherein the di-C1-C6 alkyl groups may be same or different,
- a C1-C6 alkylcarbonyl C1-C6 alkyl group,
- a phenyl group which may be monosubstituted or polysubstituted with a halogen atom, a C1-C6 alkyl group or a C1-C6 alkoxy group,
- a C7-C11 aralkyl group which may be monosubstituted or polysubstituted with a halogen atom, cyano, nitro, a C1-C6 alkyl group, a C1-C6 haloalkyl group, a C1-C6 alkoxy group, a C1-C6 haloalkoxy group, a C1-C6 alkylthio group or a C1-C6 haloalkylthio group, an indanyl group which may be monosubstituted or polysubstituted with a halogen atom, a C1-C6 alkyl group or a C1-C6 alkoxy group,
a tetrahydronaphthyl group which may be monosubstituted or polysubstituted with a halogen atom, a C1-C6 alkyl group or a C1-C6 alkoxy group,
a heterocyclic C1-C6 alkyl group which may be monosubstituted or polysubstituted with a halogen atom, a C1-C6 alkyl group or a C1-C6 alkoxy group,
a phenoxy C1-C6 alkyl group which may be monosubstituted or polysubstituted with a halogen atom, a C1-C6 alkyl group or a C1-C6 alkoxy group,
a C7-C11 aralkyloxy C1-C6 alkyl group which may be monosubstituted or polysubstituted with a halogen atom, a C1-C6 alkyl group or a C1-C6 alkoxy group,
a phenylcarbonyl C1-C6 alkyl group which may be monosubstituted or polysubstituted with a halogen atom, a C1-C6 alkyl group or a C1-C6 alkoxy group,
a C1-C6 alkylcarbonyl group; a benzoyl group which may be monosubstituted or polysubstituted with a halogen atom, a C1-C6 alkyl group or a C1-C6 alkoxy group,
a C7-C11 aralkylcarbonyl group which may be monosubstituted or polysubstituted with a halogen atom, a C1-C6 alkyl group or a C1-C6 alkoxy group,
a C1-C6 alkoxycarbonyl group,
a C1-C6 alkylaminocarbonyl group,
a di-C1-C6 alkylaminocarbonyl group wherein the di-C1-C6 alkyl groups may be same or different,
a C1-C6 alkylsulfonyl group,
a C1-C6 haloalkylsulfonyl group,
a phenylsulfonyl group which may be monosubstituted or polysubstituted with a halogen atom, a C1-C6 alkyl group or a C1-C6 alkoxy group,
or a C7-C11 aralkylsulfonyl group which may be monosubstituted or polysubstituted with a halogen atom, a C1-C6 alkyl group or a C1-C6 alkoxy group;
X is a hydrogen atom, a halogen atom, a C1-C6 alkyl group, or a C1-C6 alkoxy group; and
n is an integer of 1 to 4, wherein X's may be different from each other when n represents an integer of 2 to 4.

2. The isoxazolin-5-one derivative according to claim 1, wherein $R^1$ is a C1-C6 fluoroalkyl group.

3. The isoxazolin-5-one derivative according to claim 1, wherein $R^1$ is a trifluoromethyl group.

4. The isoxazolin-5-one derivative according to claim 1, wherein
$R^1$ is a trifluoromethyl group;
$R^2$ is a hydrogen atom,
a C1-C6 alkyl group,
a C1-C6 alkoxy C1-C6 alkyl group,
a C7-C11 aralkyl group which may be monosubstituted or polysubstituted with a halogen atom, a C1-C6 alkyl group or a C1-C6 alkoxy group,
a C1-C6 alkylcarbonyl group,
a C1-C6 haloalkylcarbonyl group,
a C3-C6 cycloalkylcarbonyl group,
a C1-C6 alkoxy C1-C6 alkylcarbonyl group,
a benzoyl group which may be monosubstituted or polysubstituted with a halogen atom or a C1-C6 alkyl group,
a C7-C11 aralkylcarbonyl group which may be monosubstituted or polysubstituted with a halogen atom or a C1-C6 alkyl group,
a heterocyclic carbonyl group which may be monosubstituted or polysubstituted with a halogen atom or a C1-C6 alkyl group,
a heterocyclic C1-C6 alkylcarbonyl group which may be monosubstituted or polysubstituted with a halogen atom or a C1-C6 alkyl group,
a C1-C6 alkoxycarbonyl group,
a C2-C6 alkenyloxycarbonyl group,
a C1-C6 alkoxy C1-C6 alkoxycarbonyl group,
a phenoxycarbonyl group which may be monosubstituted or polysubstituted with a halogen atom or a C1-C6 alkyl group,
a C7-C11 aralkyloxycarbonyl group which may be monosubstituted or polysubstituted with a halogen atom or a C1-C6 alkyl group,
a heterocyclic C1-C6 alkoxycarbonyl group which may be monosubstituted or polysubstituted with a halogen atom or a C1-C6 alkyl group,
a C1-C6 alkylaminocarbonyl group,
a di-C1-C6 alkylaminocarbonyl group wherein the di-C1-C6 alkyl groups may be same or different,
a C1-C6 alkylsulfonyl group,
a C1-C6 haloalkylsulfonyl group,
a C3-C6 cycloalkylsulfonyl group,
a phenylsulfonyl group which may be monosubstituted or polysubstituted with a halogen atom or a C1-C6 alkyl group,
or a C7-C11 aralkylsulfonyl group which may be monosubstituted or polysubstituted with a halogen atom or a C1-C6 alkyl group;
$R^3$ is a hydrogen atom,
a C1-C6 alkyl group which may be substituted with a fluorine atom,
or a C3-C6 cycloalkyl group;
$R^4$ is a hydrogen atom,
a C1-C15 alkyl group,
a C1-C15 haloalkyl group,
a C2-C6 alkenyl group,
a C2-C6 alkynyl group,
a C3-C6 cycloalkyl group,
a C3-C6 cycloalkyl C1-C6 alkyl group,
a C1-C6 alkoxy C1-C6 alkyl group,
a C1-C6 alkylthio C1-C6 alkyl group,
a phenyl group which may be monosubstituted or polysubstituted with a halogen atom, a C1-C6 alkyl group or a C1-C6 alkoxy group,
a C7-C11 aralkyl group which may be monosubstituted or polysubstituted with a halogen atom, cyano, nitro, a C1-C6 alkyl group, a C1-C6 haloalkyl group, a C1-C6 alkoxy group, a C1-C6 haloalkoxy group, a C1-C6 alkylthio group or a C1-C6 haloalkylthio group,
an indanyl group which may be monosubstituted or polysubstituted with a halogen atom, a C1-C6 alkyl group or a C1-C6 alkoxy group,
a tetrahydronaphthyl group which may be monosubstituted or polysubstituted with a halogen atom, a C1-C6 alkyl group or a C1-C6 alkoxy group,
a heterocyclic C1-C6 alkyl group which may be monosubstituted or polysubstituted with a halogen atom, a C1-C6 alkyl group or a C1-C6 alkoxy group,
a phenoxy C1-C6 alkyl group which may be monosubstituted or polysubstituted with a halogen atom, a C1-C6 alkyl group or a C1-C6 alkoxy group,
a C7-C11 aralkyloxy C1-C6 alkyl group which may be monosubstituted or polysubstituted with a halogen atom, a C1-C6 alkyl group or a C1-C6 alkoxy group,
a C1-C6 alkylcarbonyl group,
a di-C1-C6 alkylaminocarbonyl group wherein the di-C1-C6 alkyl groups may be same or different, a C1-C6 alkylsulfonyl group,
or a phenylsulfonyl group which may be monosubstituted or polysubstituted with a halogen atom, a C1-C6 alkyl group or a C1-C6 alkoxy group;
X is a hydrogen atom or a halogen atom; and
n is an integer of 1 to 4 wherein X's may be different from each other when n represents an integer of 2 to 4.

5. A herbicide comprising the isoxazolin-5-one derivative according to claim 1 as an active ingredient.

6. The isoxazolin-5-one derivative according to claim 2, wherein $R^1$ is a trifluoromethyl group.

7. The isoxazolin-5-one derivative according to claim 2, wherein
$R^1$ is a trifluoromethyl group;
$R^2$ is a hydrogen atom,
a C1-C6 alkyl group,
a C1-C6 alkoxy C1-C6 alkyl group,
a C7-C11 aralkyl group which may be monosubstituted or polysubstituted with a halogen atom, a C1-C6 alkyl group or a C1-C6 alkoxy group,
a C1-C6 alkylcarbonyl group,
a C1-C6 haloalkylcarbonyl group,
a C3-C6 cycloalkylcarbonyl group,
a C1-C6 alkoxy C1-C6 alkylcarbonyl group,
a benzoyl group which may be monosubstituted or polysubstituted with a halogen atom or a C1-C6 alkyl group,
a C7-C11 aralkylcarbonyl group which may be monosubstituted or polysubstituted with a halogen atom or a C1-C6 alkyl group,
a heterocyclic carbonyl group which may be monosubstituted or polysubstituted with a halogen atom or a C1-C6 alkyl group,
a heterocyclic C1-C6 alkylcarbonyl group which may be monosubstituted or polysubstituted with a halogen atom or a C1-C6 alkyl group,
a C1-C6 alkoxycarbonyl group,
a C2-C6 alkenyloxycarbonyl group,
a C1-C6 alkoxy C1-C6 alkoxycarbonyl group,
a phenoxycarbonyl group which may be monosubstituted or polysubstituted with a halogen atom or a C1-C6 alkyl group,
a C7-C11 aralkyloxycarbonyl group which may be monosubstituted or polysubstituted with a halogen atom or a C1-C6 alkyl group,
a heterocyclic C1-C6 alkoxycarbonyl group which may be monosubstituted or polysubstituted with a halogen atom or a C1-C6 alkyl group,
a C1-C6 alkylaminocarbonyl group; a di-C1-C6 alkylaminocarbonyl group wherein the di-C1-C6 alkyl groups may be same or different,
a C1-C6 alkylsulfonyl group,
a C1-C6 haloalkylsulfonyl group,
a C3-C6 cycloalkylsulfonyl group,
a phenylsulfonyl group which may be monosubstituted or polysubstituted with a halogen atom or a C1-C6 alkyl group,
or a C7-C11 aralkylsulfonyl group which may be monosubstituted or polysubstituted with a halogen atom or a C1-C6 alkyl group,
$R^3$ is a hydrogen atom,
a C1-C6 alkyl group which may be substituted with a fluorine atom,
or a C3-C6 cycloalkyl group;
$R^4$ is a hydrogen atom,
a C1-C15 alkyl group,
a C1-C15 haloalkyl group,
a C2-C6 alkenyl group,
a C2-C6 alkynyl group,
a C3-C6 cycloalkyl group,
a C3-C6 cycloalkyl C1-C6 alkyl group,
a C1-C6 alkoxy C1-C6 alkyl group,
a C1-C6 alkylthio C1-C6 alkyl group,
a phenyl group which may be monosubstituted or polysubstituted with a halogen atom, a C1-C6 alkyl group or a C1-C6 alkoxy group,
a C7-C11 aralkyl group which may be monosubstituted or polysubstituted with a halogen atom, cyano, nitro, a C1-C6 alkyl group, a C1-C6 haloalkyl group, a C1-C6 alkoxy group, a C1-C6 haloalkoxy group, a C1-C6 alkylthio group or a C1-C6 haloalkylthio group,
an indanyl group which may be monosubstituted or polysubstituted with a halogen atom, a C1-C6 alkyl group or a C1-C6 alkoxy group,
a tetrahydronaphthyl group which may be monosubstituted or polysubstituted with a halogen atom, a C1-C6 alkyl group or a C1-C6 alkoxy group,
a heterocyclic C1-C6 alkyl group which may be monosubstituted or polysubstituted with a halogen atom, a C1-C6 alkyl group or a C1-C6 alkoxy group,
a phenoxy C1-C6 alkyl group which may be monosubstituted or polysubstituted with a halogen atom, a C1-C6 alkyl group or a C1-C6 alkoxy group,
a C7-C11 aralkyloxy C1-C6 alkyl group which may be monosubstituted or polysubstituted with a halogen atom, a C1-C6 alkyl group or a C1-C6 alkoxy group,
a C1-C6 alkylcarbonyl group,
a di-C1-C6 alkylaminocarbonyl group wherein the di-C1-C6 alkyl groups may be same or different,
a C1-C6 alkylsulfonyl group,
or a phenylsulfonyl group which may be monosubstituted or polysubstituted with a halogen atom, a C1-C6 alkyl group or a C1-C6 alkoxy group;
X is a hydrogen atom or a halogen atom; and
n is an integer of 1 to 4 wherein X's may be different from each other when n represents an integer of 2 to 4.

8. The isoxazolin-5-one derivative according to claim 3, wherein in the formula (1),
$R^1$ is a trifluoromethyl group;
$R^2$ is a hydrogen atom,
a C1-C6 alkyl group,
a C1-C6 alkoxy C1-C6 alkyl group,
a C7-C11 aralkyl group which may be monosubstituted or polysubstituted with a halogen atom, a C1-C6 alkyl group or a C1-C6 alkoxy group,
a C1-C6 alkylcarbonyl group,
a C1-C6 haloalkylcarbonyl group,
a C3-C6 cycloalkylcarbonyl group,
a C1-C6 alkoxy C1-C6 alkylcarbonyl group,
a benzoyl group which may be monosubstituted or polysubstituted with a halogen atom or a C1-C6 alkyl group,
a C7-C11 aralkylcarbonyl group which may be monosubstituted or polysubstituted with a halogen atom or a C1-C6 alkyl group,
a heterocyclic carbonyl group which may be monosubstituted or polysubstituted with a halogen atom or a C1-C6 alkyl group,
a heterocyclic C1-C6 alkylcarbonyl group which may be monosubstituted or polysubstituted with a halogen atom or a C1-C6 alkyl group,
a C1-C6 alkoxycarbonyl group,
a C2-C6 alkenyloxycarbonyl group, a C1-C6 alkoxy C1-C6 alkoxycarbonyl group,
a phenoxycarbonyl group which may be monosubstituted or polysubstituted with a halogen atom or a C1-C6 alkyl group,
a C7-C11 aralkyloxycarbonyl group which may be monosubstituted or polysubstituted with a halogen atom or a C1-C6 alkyl group,
a heterocyclic C1-C6 alkoxycarbonyl group which may be monosubstituted or polysubstituted with a halogen atom or a C1-C6 alkyl group,
a C1-C6 alkylaminocarbonyl group,
a di-C1-C6 alkylaminocarbonyl group wherein the di-C1-C6 alkyl groups may be same or different,
a C1-C6 alkylsulfonyl group,
a C1-C6 haloalkylsulfonyl group,
a C3-C6 cycloalkylsulfonyl group,
a phenylsulfonyl group which may be monosubstituted or polysubstituted with a halogen atom or a C1-C6 alkyl group,
or a C7-C11 aralkylsulfonyl group which may be monosubstituted or polysubstituted with a halogen atom or a C1-C6 alkyl group;
$R^3$ is a hydrogen atom,
a C1-C6 alkyl group which may be substituted with a fluorine atom,
or a C3-C6 cycloalkyl group;
$R^4$ is a hydrogen atom,
a C1-C15 alkyl group,
a C1-C15 haloalkyl group,
a C2-C6 alkenyl group,
a C2-C6 alkynyl group,
a C3-C6 cycloalkyl group,
a C3-C6 cycloalkyl C1-C6 alkyl group,
a C1-C6 alkoxy C1-C6 alkyl group,
a C1-C6 alkylthio C1-C6 alkyl group,
a phenyl group which may be monosubstituted or polysubstituted with a halogen atom, a C1-C6 alkyl group or a C1-C6 alkoxy group,
a C7-C11 aralkyl group which may be monosubstituted or polysubstituted with a halogen atom, cyano, nitro, a C1-C6 alkyl group, a C1-C6 haloalkyl group, a C1-C6 alkoxy group, a C1-C6 haloalkoxy group, a C1-C6 alkylthio group or a C1-C6 haloalkylthio group,
an indanyl group which may be monosubstituted or polysubstituted with a halogen atom, a C1-C6 alkyl group or a C1-C6 alkoxy group,
a tetrahydronaphthyl group which may be monosubstituted or polysubstituted with a halogen atom, a C1-C6 alkyl group or a C1-C6 alkoxy group,
a heterocyclic C1-C6 alkyl group which may be monosubstituted or polysubstituted with a halogen atom, a C1-C6 alkyl group or a C1-C6 alkoxy group,
a phenoxy C1-C6 alkyl group which may be monosubstituted or polysubstituted with a halogen atom, a C1-C6 alkyl group or a C1-C6 alkoxy group,
a C7-C11 aralkyloxy C1-C6 alkyl group which may be monosubstituted or polysubstituted with a halogen atom, a C1-C6 alkyl group or a C1-C6 alkoxy group,
a C1-C6 alkylcarbonyl group,
a di-C1-C6 alkylaminocarbonyl group wherein the di-C1-C6 alkyl groups may be same or different,
a C1-C6 alkylsulfonyl group,
or a phenylsulfonyl group which may be monosubstituted or polysubstituted with a halogen atom, a C1-C6 alkyl group or a C1-C6 alkoxy group;
X is a hydrogen atom or a halogen atom; and
n is an integer of 1 to 4 wherein X's may be different from each other when n represents an integer of 2 to 4.

9. A herbicide comprising the isoxazolin-5-one derivative according to claim 2 as an active ingredient.

10. A herbicide comprising the isoxazolin-5-one derivative according to claim 3 as an active ingredient.

11. A herbicide comprising the isoxazolin-5-one derivative according to claim 4 as an active ingredient.

* * * * *